(12) United States Patent
Asberom et al.

(10) Patent No.: US 6,969,719 B2
(45) Date of Patent: Nov. 29, 2005

(54) POLYCYCLIC GUANINE PHOSPHODIESTERASE V INHIBITORS

(75) Inventors: Theodros Asberom, West Orange, NJ (US); Yueqing Hu, Kowloon (HK); Dmitri Pissarnitski, Scotch Plains, NJ (US); Ruo Xu, Watchung, NJ (US); Yuguang Wang, North Brunswick, NJ (US); Samuel Chackalamannil, East Brunswick, NJ (US); John W. Clader, Cranford, NJ (US); Andrew William Stamford, Chatham Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 95 days.

(21) Appl. No.: 10/227,778

(22) Filed: Aug. 26, 2002

(65) Prior Publication Data

US 2003/0153587 A1 Aug. 14, 2003

Related U.S. Application Data

(60) Provisional application No. 60/315,395, filed on Aug. 28, 2001.

(51) Int. Cl.[7] .................. C07D 487/14; C07D 487/20; A61K 31/519; A61K 31/527; A61P 15/10
(52) U.S. Cl. .................. 514/257; 514/267; 544/230; 544/247; 544/251
(58) Field of Search ................. 514/257, 267; 544/247, 251, 230

(56) References Cited

U.S. PATENT DOCUMENTS

| | | | |
|---|---|---|---|
| 5,321,029 A | | 6/1994 | Maschler et al. |
| 5,393,755 A | * | 2/1995 | Neustadt et al. ......... 514/233.2 |
| 5,409,934 A | | 4/1995 | Smith et al. |
| 5,470,579 A | | 11/1995 | Bonte et al. |
| 5,637,593 A | | 6/1997 | Porter et al. |
| 5,824,683 A | | 10/1998 | McKittrick et al. |

(Continued)

FOREIGN PATENT DOCUMENTS

| | | |
|---|---|---|
| DE | P 19 38 016.6 | 1/1971 |
| EP | 0 258 191 A1 | 3/1988 |
| EP | 0 389 282 A2 | 9/1990 |
| EP | 0 463 756 A1 | 1/1992 |
| EP | 0702555 B1 | 11/1998 |
| FR | 2 116 302 | 7/1972 |
| WO | WO 91/07945 | 6/1991 |
| WO | WO 91/07945 A1 | 6/1991 |
| WO | WO91/19717 | 12/1991 |
| WO | WO 91 19717 A | 12/1991 |
| WO | WO 92/05175 | 4/1992 |
| WO | WO 92/05176 | 4/1992 |
| WO | WO 93/23401 | 11/1993 |
| WO | WO 94 19351 | 9/1994 |
| WO | WO 94/28902 | 12/1994 |
| WO | WO 99/24433 | 5/1999 |
| WO | WO 99/54331 A1 | 10/1999 |
| WO | WO 99/54331 | 10/1999 |
| WO | WO 99/62905 | 12/1999 |

OTHER PUBLICATIONS

David J.W. Grant, "University of Minnesota—Twin Cities Campus College of Pharmacy, Annual Report", [online] 1999, [retrieved on Feb. 13, 2003]. Retrieved from the internet, <http://www.msi.umn.edu/general/Reports/ar99/departments/pharmacy.html>.*

(Continued)

Primary Examiner—Thomas C. McKenzie
(74) Attorney, Agent, or Firm—Gerard E. Reinhardt

(57) ABSTRACT

A polycyclic guanine phosphodiesterase V inhibitor having the formula (I.1) or (II.1), with the variables defined herein, which is useful for treating sexual dysfunction and other physiological disorders:

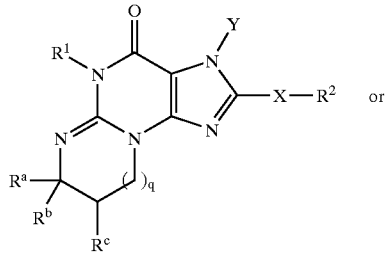

(I.1)

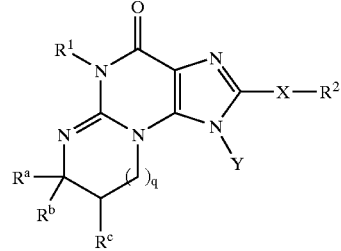

(II.1)

A representative example is:

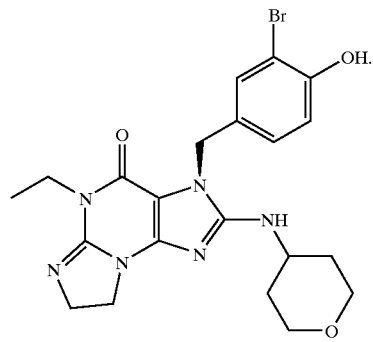

26 Claims, No Drawings

U.S. PATENT DOCUMENTS

| | | | |
|---|---|---|---|
| 5,939,419 A | 8/1999 | Tulshian et al. |
| 5,955,611 A | 9/1999 | Dunn et al. |
| 5,981,563 A | 11/1999 | Lowrey |
| 6,023,640 A | 2/2000 | Ross |
| 6,037,346 A | 3/2000 | Doherty, Jr. et al. |
| 6,051,594 A | 4/2000 | Lowrey |
| 6,066,735 A | 5/2000 | Dunn et al. |
| 6,087,362 A | 7/2000 | El-Rashidy |
| 6,100,270 A | 8/2000 | Campbell |
| 6,140,329 A | 10/2000 | Daugan |
| 6,403,597 B1 | 6/2002 | Wilson et al. |
| 2002/0091129 A1 | 7/2002 | Boolell |

OTHER PUBLICATIONS

Gavazzotti, Angelo, Acc. Chem. Res., 1994, 27, 309–314.*

West, Anthony R., "Solid State Chemistry and its Applications", Wiley, New York, 1988, pp. 358 & 365.*

Perry, M.J. et al, Current Opinion in Chemical Biology, 1998, 2, 472–481.*

Corbin JD, Francis SH., Int J Clin Pract. Jul.–Aug. 2002;56(6):453–9.*

Cremers B, Bohm M., Herz. Jun. 2003;28(4):325–33.*

Bortolotti, M., et al, "Effect of Sildenafil on hypertensive lower oesophageal sphincter", European Journal of Clinical Investigation, vol. 32, pp. 682–685, (2002).

Eherer, A J., et al, "Effect of sildenafil on oesophageal motor function in healthy subjects and patients with oesphageal motor disorders", GUT, vol. 50, pp. 758–764, (2002).

Ghofrani, Hossein A., et al, "Combination Therapy with Oral Sildenafil and Inhaled Iloprost for Severe Pulmonary Hypertension", Annals of Internal Medicine, vol. 136, No. 7, pp. 515–522, (2002).

Ghofrani, Hossein A., et al, "Sildenafil for Long–Term Treatment of Nonoperable Chronic Thromboembolic Pulmonary Hypertension", American Journal of Respiratory and Critical Care Medicine, vol. 167, pp1139–1141, (2003).

Ghofrani, Hossein A., et al, "Sildenafil for treatment of lung fibrosis and pulmonary hypertension: a randomized controlled trial", The Lancet, vol. 360, pp. 895–900, (2002).

Inoha, Satoshi, et al, "Type V phosphodiesterase expression in cerebral arteries with vasospasm after subarachnoid hemorrhage in a canine model", Neurological Research 2002, vol. 24, pp. 607–612, (2002).

Koppiker, Nandan, "Use of Cgmp PDE5 inhibitors in the treatment of neuropathy: A review of the patent literature", Idrugs, vol. 5 (5), pp. 448–453, (2002).

Rotella, D., "Phosphodiesterase 5 Inhibitors: Current Status and Potential Applications", Nature, vol. 1, pp. 674–682, (2002).

Zhang, Ruilan, M.D. et al, "Sildenafil (Viagra) Induces Neurogenesis and Promotes Functional Recovery After Stroke in Rats", Stroke, pp. 2675–2680, (2002).

Ho–Sam Ahn, et al, "Potent Tetracyclic Guanine Inhibitors of PDE1 and PDE5 Cyclic Guanosine Monophosphate Phosphodiesterases with Oral Hypertensive Activity," Journal of Medicinal Chemistry, vol. 40, No. 14, pp. 2196–2210 (1997).

D. Doller, et al, "The Gif System as a Tool in Medicinal Chemistry: The Oxidation of SCH57726 under GOAGG Conditions," Bioorganic and Medicinal Chemistry Letters, vol. 7, No. 11, pp. 1381–1386 (1997).

J. Shimada, et al, "A Convenient Synthesis of Tricyclic Purine Derivatives," Journal of Heterocyclic Chemistry, vol. 30, No. 1, pp. 241–246 (1993).

S. Vemulapalli, et al, "Antiplatelet and Antiproliferative Effects of SCH 51866, a Novel Type 1 and Type 5 Phosphodiesterase Inhibitor," Journal of Cardiovascular Pharmacology, vol. 28, pp. 862–869 (1996).

International Search Report, based on PCT/US 02/27181, Jan. 13, 2003.

Ahn, Ho–Sam, et al, "Potent Tetracyclic Guanine Inhibitors of PDE1 and PDE5 Cyclic Guanosine Monophosphate Phosphodiesterases with Oral Antihypertensive Activity", J. Med. Chem., Vol. 40, No. 14, pp. 2196–2210 (1997).

International Search Report, PCT/US 02/35721, Feb. 13, 2003.

Dukarm R.C., et al., (1999) The cGMP–specific Phosphodiesterase Inhibitor E4021 Dilates the Pulmonary Circulation. American Journal Respir. Crit. Care Med., vol. 160:858–865.

Gaine S.P., et al., (1998) Primary Pulmonary Hypertension. The Lancet, vol. 352:719–725.

Hanasato N., et al., (1999) E–4010, a Selective Phosphodiesterase 5 Inhibitor, Attenuates Hypoxic Pulmonary Hypertension in Rats. American Journal of Physiol., vol. 277 (Lung Cell. Mol. Physiol. 21:L225–L232.

Ohnishi M., et al., (1999) E4021, a Selective Phosphodiesterase 5 Inhibitor, Potentiates the Vasodilator Effect of Inhaled Nitric Oxide in Isolated Perfused Rat Lungs. Journal of Cardiovascular Pharmacology, vol. 33:619–624.

Murray, K.J., Phosphodiesterase V Inhibitors, DN&P 6(3), pp. 150–155, Apr. 1993.

Nantka–Namirski, P. et al., Synteza 7–Podstawionych Pochodnych 8–aminometylo–1,3–Dwumetloksantyny, Acia, Polan, Pharm. XXX1 Nr 1, (1974) [in Polish].

Nantka–Namirski, P. et al., Synthesis of 7–Substituted Deviates of 8–aminomethyl–1,3–dimethylxanthine, Acta. Polon, Pharma. 31(1):5–11 (1974) [English translation].

T. Katsushima et al., Structure–Activity Relationships of 8–Cycloalkyl–1,3–diprophylxanthines as Antagonists of Adenosine Receptors, J. Med. Chem. 1990, 33, pp. 1906–1910.

XP–002188426, Synthesis and biological activity of 3–methyl, 7– or 8–alkyl–, 7,8–dialkyl, heterocyclic, and cyclohexylaminoxanthines, 6001 Chemical Abstracts, Columbus, Ohio, US, No. 106:95577n, (1987).

Yoneda, F. et al., A New Synthesis of Substituted 8–Aminopurine Derivatives, Bulletin of the Chemical Society of Japan, vol. 46, pp. 1836–1839 (1973).

Youssef, S. et al., Purines XIV.[1] Reactivity of 8–Bromo–3–9–dimethylxanthine Towards Some Nucleophilic Reagents, J. Heterocyclic Chem., 35, 949 (1998).

Remingtons's Pharmaceutical Sciences, 18$^{th}$ Ed., Mack Publishing Co., pp. 1288–1300 (1990).

Handbook of Pharmaceutical Excipients, American Pharmaceutical Association & the Pharmaceutical Society of Great Britain, pp. 81–90 (1986).

Physician's Desk Reference, 55$^{th}$ Ed, pp. 2534–2537 (2001).

* cited by examiner

POLYCYCLIC GUANINE PHOSPHODIESTERASE V INHIBITORS

BACKGROUND OF THE INVENTION

1. Field of the Invention

The invention relates to polycyclic nucleotide guanine phosphodiesterase V inhibitors.

2. Description of Related Art

Phosphodiesterase ("PDE") V inhibitor compounds are described by Kenneth J. Murray in *Phosphodiesterase V$_A$ Inhibitors, DN & P* 6(3), pp. 150–156 (April, 1993), which is hereby incorporated herein by reference in its entirety, to have potential therapeutic value for a number of physiological disorders. One compound disclosed in the Murray article is MIMAX, a polycyclic xanthine PDE V inhibitor substituted at its 8-position with a —NHCH$_3$ group. U.S. Pat. No. 5,409,934, U.S. Pat. No. 5,470,579, WO 93/23401, WO 92/05176 and WO 92/05175, each of which is hereby incorporated herein by reference in its entirety, disclose a series of xanthine PDE V inhibitors that are substituted at the 8-position with a number of different functionalities. Other types of heterocyclic PDE V inhibitors useful for treating impotence are disclosed in U.S. Pat. No. 6,140,329, U.S. Pat. No. 6,100,270 and WO 94/28902, all of which are hereby incorporated herein by reference in their entirety.

Specific PDE V inhibitors have been found useful for specific indications. For example, the use of specific PDE V inhibitors for treating impotence has met with commercial success with the introduction of sildenafil citrate, a PDE V inhibitor better known as Viagra® (Pfizer, NY, N.Y.). The chemistry and use of Viagra®, including its mechanism of action in treating erectile dysfunction, are taught in EP 0 702 555 B1. Additional PDE V inhibitors useful for treating erectile dysfunction are disclosed in WO 99/24433.

Erectile dysfunction is a treatable and highly recognized health concern, affecting more than 30 million men in the United States, including one in four over age 65. Erectile dysfunction occurs when a man consistently is unable to sustain an erection sufficient for conducting sexual intercourse. In the past, psychological reasons were the most common explanation for erectile dysfunction or it was considered a natural part of aging. However, researchers today acknowledge that more than 70 percent of instances of erectile dysfunction are due to physical or medical problems. There are several factors that may contribute to erectile dysfunction, including:

Poor blood circulation—atherosclerosis or hardening of the arteries, high blood pressure and high cholesterol.

Neurological disorders—multiple sclerosis, Alzheimer's disease and Parkinson's disease.

Hormone imbalances—diabetes, thyroid disorders and low testosterone levels.

Trauma—spinal cord injury, prostate surgery or other trauma to the pelvic area.

Prescription and over-the-counter medications—blood pressure medications, antidepressants and certain drug combinations.

Lifestyle habits—smoking, alcohol and other drugs.

U.S. Pat. No. 5,939,419 and U.S. Pat. No. 5,393,755, both of which are hereby incorporated herein by reference in their entirety, disclose polycyclic guanine PDE V derivatives that are useful for the treatment of cardiovascular and pulmonary disorders.

As has been shown by the representative art, certain xanthine/guanine PDE V inhibitors have been found to be useful for treating cardiovascular and pulmonary disorders, while others have been found useful for treating impotence.

It is an object of the invention to provide a polycyclic guanine PDE V inhibitor that possesses one or more of the following: beneficial therapeutic properties, useful pharmacological properties and good metabolic stability.

It is another object of the invention to provide a polycyclic guanine PDE V inhibitor that is effective for treating a variety of physiological symptoms and diseases in which PDE V plays a role.

It is still another object of invention to provide a polycyclic guanine PDE V inhibitor that is highly potent and selective over other types of PDEs.

It is also an object of the invention to provide a polycyclic guanine PDE V inhibitor that is especially effective for treating erectile dysfunction with minimal side effects.

These and other objects of the invention will become apparent as the description progresses.

SUMMARY OF THE INVENTION

In one aspect of the invention, a compound is provided having the formula (I.1) or (II.1):

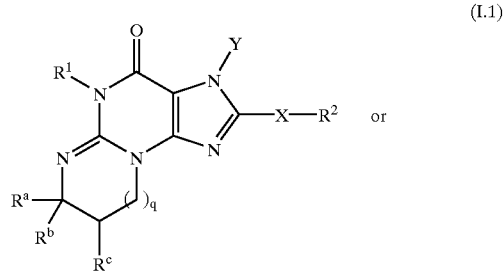

(I.1)

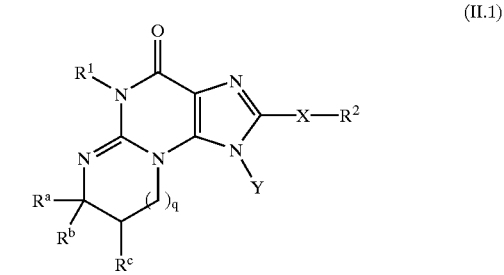

(II.1)

or a pharmaceutically acceptable salt or solvate thereof where, q=0 or 1;

$R^1$ is H, cycloalkyl, alkyl, $R^{23}$-alkyl- or $R^{26}$;

$R^a$, $R^b$ and $R^c$ are, independently of one another, each H, alkyl, cycloalkyl, aryl, $R^{22}$-aryl- or $R^{24}$-alkyl-; or $R^a$ and $R^b$, together with the carbon to which they are both attached, form a 4- to 7-membered ring, and $R^c$ is H or alkyl; or $R^a$ and $R^c$, together with the respective carbons to which they are attached, form a 4- to 7-membered ring, and $R^b$ is H or alkyl;

(i) X is a bond;

Y is H, $R^{26}$, cycloalkyl, alkyl, $R^{25}$-alkyl- or —(CH$_2$)$_t$TCOR$^{100}$, where t is 1 to 6, T is —O— or —NH—, and $R^{100}$ is H, $R^{26}$, alkyl or $R^{26}$-alkyl-; and $R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;

(ii) X is a bond;
  Y is Q-V, where Q is a bond or $C_1$–$C_8$ alkyl, and V is:
    (a) aryl substituted with nitro, aminosulfonyl, cyano, monohaloalkyl, polyhaloalkyl, provided that it is not trifluoromethyl, thiol, alkylthio, cycloalkyl, cycloalkylalkyl, —$OCF_3$ or acyloxy, and optionally further substituted with 1 to 3 additional substituents independently selected from the group consisting of $R^{21}$;
    (b) $R^{22}$-heteroaryl-; or
    (c) aryl or heteroaryl, each of which is independently substituted with 2 substituents on adjacent atoms of the group V, which are joined to form a fused non-aromatic 4- to 8-membered carbocyclic or heterocyclic ring, and optionally further substituted with 1 to 2 additional substituents independently selected from the group consisting of $R^{21}$; and
  $R^2$ is H, halo, —$CONHR^6$, —$CONR^6R^7$, —$CO_2R^6$, monohaloalkyl, polyhaloalkyl, azido, cyano, —C=N—$OR^6$, cycloalkyl, cycloalkylalkyl, $R^{26}$, aminosulfonyl, alkyl or $R^{23}$-alkyl-;
(iii) X is —O— or —S—;
  Y is defined in section (i) above; and
  $R^2$ is $R^{26}$, cycloalkyl, cycloalkylalkyl, heterocycloalkyl, cycloalkenyl or $R^{28}$-alkyl-;
(iv) X is —O— or —S—;
  Y is defined in section (ii) above; and
  $R^2$ is alkyl, $R^{26}$, cycloalkyl, cycloalkylalkyl, heterocycloalkyl, cycloalkenyl or $R^{28}$-alkyl-;
(v) X is —SO— or —$SO_2$—;
  Y is defined in section (i) or (ii) above; and
  $R^2$ is alkyl, $R^{26}$, cycloalkyl, cycloalkylalkyl, heterocycloalkyl, cycloalkenyl or $R^{28}$-alkyl-;
(vi) X is —$NR^8$—;
  Y is defined in section (i) above; and
  $R^2$ is $(R^{29})_p$-alkyl-, cycloalkyl, $(R^{30})_p$-cycloalkyl-, cycloalkenyl, $(R^{30})_p$-cycloalkenyl-, heterocycloalkyl or $(R^{30})_p$-heterocycloalkyl-;
(vii) X is —$NR^8$—;
  Y is defined in section (ii) above; and
  $R^2$ is alkyl, $R^{26}$, cycloalkyl, cycloalkylalkyl, heterocycloalkyl, cycloalkenyl or $R^{31}$-alkyl-; or
(viii) X is —C≡C—;
  Y is defined in section (i) or (ii) above; and
  $R^2$ is alkyl, $R^{26}$, cycloalkyl, cycloalkylalkyl or $R^{23}$-alkyl-;
where,
  $R^6$ is H or $R^7$;
  $R^7$ is alkyl, cycloalkyl or cycloalkylalkyl;
  $R^8$ is heterocycloalkyl or $R^6$;
  $R^{21}$ is 1–6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cycloalkyl, cycloalkylalkyl, amino, alkylamino, acylamino, carboxyl, —$C(O)OR^{34}$, carboxamido, —$OCF_3$ and acyloxy;
  $R^{22}$ is 1–6 substituents each independently selected from the group consisting of alkyl and $R^{21}$;
  $R^{23}$ is cycloalkoxy aryloxy, alkylthio, arylthio, cycloalkyl or $R^{28}$;
  $R^{24}$ is cycloalkyl or $R^{26}$;
  $R^{25}$ is hydroxy, alkoxy, amino, monoalkylamino, dialkylamino or $R^{26}$;
  $R^{26}$ is aryl, $R^{22}$-aryl-, heteroaryl or $R^{22}$-heteroaryl-;
  $R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;
  $R^{28}$ is cycloalkylamino, heterocycloalkylamino or $R^{25}$;
  $R^{29}$ is alkoxy, cycloalkylamino, heterocycloalkylamino or $R^{26}$;
  $R^{30}$ is halo, hydroxy, alkoxy, amino, aminosulfonyl, cyano, monohaloalkyl, polyhaloalkyl, thiol, alkylthio, alkyl, cycloalkyl, cycloalkylalkyl or acyloxy;
  $R^{31}$ is cycloalkyl or $R^{28}$;
  $R^{34}$ is alkyl, aryl, aralkyl and heteroaryl; and
  p is 1 to 4

The invention comprises at least one compound of the formula (I.1) or (II.1), which includes any and all enantiomers, stereoisomers, rotomers, tautomers and pro-drugs of the at least one inventive compound. Compounds of the formula (I.1) or (II.1) also include their corresponding salts, solvates, esters and the like. The invention further comprises pharmaceutically acceptable compositions prepared from an inventive compound or a mixture of inventive compounds, or a salt, solvate or ester thereof. The compounds of formula (I.1) or (II.1) can be useful for treating a variety of diseases, symptoms and physiological disorders, such as sexual dysfunction, especially impotence (e.g., erectile dysfunction).

A further understanding of the invention will be had from the following detailed description of the invention, including its preferred embodiments.

Definitions and Usage of Terms

The following definitions and terms are used herein or are otherwise known to a skilled artisan. Except where stated otherwise, the following definitions apply throughout the specification and claims. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

The term "substituted," as used herein, means the replacement of one or more atoms or radicals, usually hydrogen atoms, in a given structure with an atom(s) or radical(s) selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, alkenyl, cycloalkenyl, alkynyl, arylalkyl, alkylaryl, heterocycloalkyl, aryl and heteroaryl groups, independently of or together with one another, may be substituents on any substituted group, unless otherwise stated, shown or known to be otherwise.

The term "heteroatom," as used herein, means a nitrogen, sulfur, or oxygen atom. Multiple heteroatoms in the same group may be the same or different.

The term "alkyl," as used herein, means an unsubstituted or substituted, straight or branched, hydrocarbon chain having, preferably, from one to twenty-four carbon atoms, more preferably, from one to twelve carbon atoms, even more preferably, from one to eight carbon atoms, and most preferably, from one to six carbon atoms.

The term "cycloalkyl," as used herein, means an unsubstituted or substituted, saturated, stable non-aromatic carbocyclic ring, having, preferably, from three to fifteen carbon atoms, more preferably, from three to eight carbon atoms. The carbon ring radical is saturated and may be fused, for example, benzofused, with one to three cycloalkyl, aromatic, heterocyclic or heteroaromatic rings. The cycloalkyl may be attached at any endocyclic carbon atom that results in a stable structure. Preferred carbocycles have from five to six carbons. Examples of carbocycle radicals include cyclopropyl, cyclobutyl, cyclopentyl, cyclohexyl, cycloheptyl and the like.

The term "alkenyl," as used herein, means an unsubstituted or substituted, unsaturated, straight or branched, hydrocarbon chain having at least one double bond present and, preferably, from two to fifteen carbon atoms, more preferably, from two to twelve carbon atoms.

The term "cycloalkenyl," as used herein, means an unsubstituted or substituted, unsaturated carbocyclic ring having at least one double bond present and, preferably, from three to fifteen carbon atoms, more preferably, from five to eight carbon atoms. A cycloalkenyl goup is an unsaturated carbocyclic group. Examples of cycloalkenyl groups include cyclopentenyl and cyclohexenyl.

The term "alkynyl," as used herein, means an unsubstituted or substituted, unsaturated, straight or branched, hydrocarbon chain having at least one triple bond present and, preferably, from two to twelve carbon atoms, more preferably, two to ten carbon atoms.

The term "bicycloalkyl," as used herein, represents a saturated linearly fused or bridged carbocyclic ring having, preferably, from 5 to 12 carbon atoms.

The term "aryl," as used herein, means a substituted or unsubstituted, aromatic, mono- or bicyclic carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, cumenyl, naphthyl, tetrahydronaphthyl, indanyl, indenyl and the like. If desired, the carbocyclic moiety can be substituted with from one to five, preferably, one to three moieties, such as mono- through pentahalo, alkyl, trifluoromethyl, phenyl, hydroxy, alkoxy, phenoxy, amino, monoalkylamino, dialkylamino and the like.

The term "heteroaryl," as used herein, means a mono- or bicyclic ring system containing one or two aromatic rings and at least one nitrogen, oxygen or sulfur atom in an aromatic ring. Heteroaryl groups (including bicyclic heteroaryl groups) can be unsubstituted or substituted with a plurality of substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino and the like). Typically, a heteroaryl group represents a cyclic group of five or six atoms, or a bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocycloalkyl," as used herein, means an unsubstituted or substituted, saturated cyclic ring system having from three to fifteen members, preferably, from three to eight members, and comprising carbon atoms and at least one heteroatom as part of the ring.

The term "heterocyclic," as used herein, means an unsubstituted or substituted, saturated or unsaturated ring, comprised of carbon atoms and one or more heteroatoms in the ring. Heterocyclic rings may be monocyclic or polycyclic. Monocyclic rings preferably contain from three to eight atoms, most preferably, five to seven atoms. Polycyclic ring systems consisting of two rings preferably contain from six to sixteen atoms, most preferably, ten to twelve atoms. Polycyclic ring systems consisting of three rings contain, preferably, from thirteen to seventeen atoms, most preferably, fourteen to fifteen atoms. Each heterocyclic ring has at least one hetero atom. Unless otherwise stated, the heteroatoms may be independently selected from the following: nitrogen, sulfur and oxygen atoms.

The term "carbocyclic," as used herein, means an unsubstituted or substituted, saturated, unsaturated hydrocarbon ring, unless otherwise specifically identified. Carbocycles may be monocyclic or polycyclic. Monocyclic rings preferably contain from three to eight atoms, most preferably, five to seven atoms. Polycyclic rings having two rings preferably contain from six to sixteen atoms, most preferably, ten to twelve atoms, and those having three rings preferably contain from thirteen to seventeen atoms, most preferably, fourteen to fifteen atoms.

The term "aralkyl" or "arylalkyl," as used herein, means an alkyl moiety substituted with an optionally substituted, aryl group. Representative aralkyl groups include a benzyl group and fused bicyclic systems which contain one aryl group.

The term "alkylaryl," as used herein, means an aryl or heteroaryl moiety substituted with an optionally substituted, alkyl group.

Unless otherwise known, stated or shown to be to the contrary, the point of attachment for a multiple term substituent (multiple terms that are combined to identify a single moiety) to a subject structure is through the last named term of the multiple term. For example, an "aralkyl" substituent attaches to a targeted structure through the "alkyl" portion of the substituent. Conversely, when the substituent is "alkylaryl", it attaches to a targeted structure through the "aryl" portion of the substituent. Similarly, a cycloalkylalkyl substituent attaches to a targeted through the latter "alkyl" portion of the substituent (e.g., Structure-alkyl-cycloalkyl).

The term "alkoxy," as used herein, means an oxygen atom bonded to a hydrocarbon chain, such as an alkyl or alkenyl group (e.g., —O-alkyl or —O-alkenyl). Representative alkoxy groups include methoxy, ethoxy, and isopropoxy groups.

The term "hydroxyalkyl," as used herein, means an alkyl group having at least one hydroxy substituent (e.g., —OH). Representative hydroxyalkyl groups include hydroxymethyl, hydroxyethyl and hydroxypropyl groups.

The term "carboxyalkyl," as used herein, means an alkyl group that has a carboxyl substituent (e.g., —COOH). Representative carboxyalkyl groups include carboxymethyl ($-CH_2CO_2H$) and carboxyethyl ($-CH_2CH_2CO_2H$) groups, and derivatives thereof, such as the corresponding esters.

The term "aminoalkyl," as used herein, means an alkyl group substituted with an amine moiety (e.g., -alkyl$NH_2$), such as aminomethyl.

The term "alkylamino," as used herein, means an amino moiety having from one or two alkyl substituents (e.g., —NH-alkyl), such as dimethylamino.

The term "alkenylamino," as used herein, means an amino moiety having from one or two alkenyl substituents, where the nitrogen atom of the amino group is not attached to the alkene-forming carbon atom (e.g., —NH—CH$_2$-alkenyl), such as dibutenylamino.

The term "arylamino," as used herein, means an amine moiety substituted with an aryl group (e.g., —NH-aryl).

The term "carboxamido," as used herein, means a carbonyl moiety having an amido substituent (e.g., —C(O)NR'R", where, R' and R", independently of one another, are each hydrogen, alkyl, cycloalkyl, alkenyl, cycloalkenyl, alkynyl, arylalkyl, alkylaryl, heterocycloalkyl, aryl or heteroaryl).

The term "alkylimino," as used herein, means an imino moiety having one alkenyl or two alkyl substituents (e.g., —C=N-alkyl).

The term "oximino," as used herein, means compounds containing the —C=N—OR$^{69}$ radical, where R$^{69}$ is hydrogen, alkyl, cycloalkyl, cycloalkylalkyl or aryl.

The term "aroyl," as used herein, means the radical R—C(O)—, where R is an aromatic group. Representative aroyls are benzoyl and naphthoyl.

The term "aryloxy," as used herein, means an oxygen atom having an aryl substituent (e.g., —O-aryl).

The term "acyl" or "carbonyl," as used herein, means a carbon to oxygen double bond, (e.g., R—C(=O)—), which can be a radical of a carboxylic acid having the formula alkyl-CO—, aryl-CO—, arylalkyl-CO—, cycloalkyl-CO—, alkylcycloalkyl-CO— or heteroaryl-CO—. Representative acyl groups include acetyl, propionyl, butanoyl and benzoyl groups.

The term "acyloxy," as used herein, means an oxygen atom having an acyl substituent (e.g., —O-acyl), for example, —O—C(=O)-alkyl.

The term "acylamino," as used herein, means an amino moiety having an acyl substituent (e.g., —NH-acyl), for example, an amide with the formula —NH—(C=O)-alkyl, a urea with the formula —NH—(C=O)—NH-alkyl or a carbamate with the formula —NH—(C=O)—OR, where R is alkyl, cycloalkyl, alkenyl, cycloalkenyl, alkynyl, arylalkyl or heterocycloalkyl.

The term "halo," "halogen" or "halide," as used herein, means a chloro, bromo, fluoro or iodo atom radical. Chlorides, bromides and fluorides are preferred halides.

The term "lower hydrocarbon" (e.g., "lower alkyl"), as used herein, means a hydrocarbon chain comprised of from, unless otherwise stated, one to eight carbon atoms, preferably, one to six carbon atoms, and most preferably, one to four carbon atoms.

The term "polyhalo," as used herein, represents substitution of at least two halo atoms to a group modified by the term "polyhalo."

The term "aminosulfonyl," as used herein, represents a group having the formula —SO$_2$NR$^{79}$R$^{89}$, where R$^{79}$ and R$^{89}$ are, independently of one another, each hydrogen, lower alkyl (e.g., from 1 to 8 carbon atoms) or aryl.

The term "sulfonyl," as used herein, represents a group having the formula —S(O)$_2$—.

When a variable appears more than once in a structural formula, for example, R$^{59}$ for where X is —C(OR$^{59}$)$_2$—, the identity of each variable appearing more than once may be independently selected from the definition for that variable.

The term "prodrug," as used herein, represents a compound that is a drug precursor, which following administration to a patient, releases a drug in vivo via some kind of chemical and/or physiological process (e.g., a prodrug on being brought to a physiological pH and/or through an enzyme action is converted to a desired drug form).

The term "compound of the formula (I.1) or (II.1)", as used herein, represents a compound having a chemical structure encompassed by the formula (I.1) or (II.1), and includes any and all enantiomers, stereoisomers, rotomers, tautomers and prodrugs of the compound. Compounds of the formula (I.1) or (II.1) also include their corresponding pharmaceutically acceptable salts, solvates, esters and derivatives.

The term "pharmaceutical composition," as used herein, means a combination of at least one inventive compound (e.g., PDE V inhibitor) and at least one pharmaceutically acceptable excipient or carrier.

Other than as shown in the operating examples or where is otherwise indicated, all numbers used in the specification and claims expressing quantities of ingredients, reaction conditions, and so forth, are understood as being modified in all instances by the term "about."

DETAILED DESCRIPTION OF THE INVENTION

Referring above to the compounds of formulas (I.1) and/or (II.1) and the definitions of their variables, advantageous embodiments of the invention may include one or more of the following:

1. R$^1$ is aryl, R$^{22}$-aryl-, alkyl or R$^{23}$-alkyl-, where R$^{22}$ and R$^{23}$ are each independently defined in the summary of the invention. Preferably, R$^1$ is ethyl.
2. In sections (i) through (viii) of the summary of the invention, respectively, R$^2$ is (i) R$^{27}$-alkyl-, (ii) R$^{23}$-alkyl-, (iii) R$^{28}$-alkyl-, (iv) alkyl or R$^{28}$-alkyl-, (v) alkyl or R$^{28}$-alkyl-, (vi) (R$^{29}$)$_p$-alkyl-, (vii) alkyl or R$^{31}$-alkyl- or (viii) alkyl or R$^{23}$-alkyl where R$^{23}$, R$^{27}$, R$^{28}$, R$^{29}$, R$^{31}$ and p are each independently defined in the summary of the invention.
3. X is —NH—, and R$^2$ is:

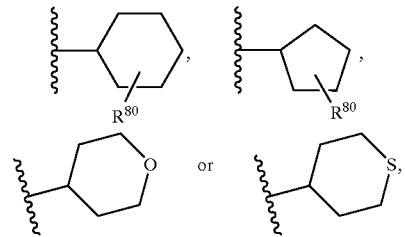

where R$^{80}$ is H or hydroxy.
4. X is —O—, Y is defined in section (ii) of the summary of the invention, and R$^2$ is alkyl or aralkyl.
5. X is —C≡C—, and R$^2$ is alkyl or R$^{26}$, where R$^{26}$ is defined in the summary of the invention.
6. X is a bond, Y is defined in section (ii) of the summary of the invention, and R$^2$ is halo, —CONHR$^6$, —CONR$^6$R$^7$, —CO$_2$R$^6$ or —C=N—OR$^6$, where R$^6$ and R$^7$ are each independently defined in the summary of the invention.

7. X is a bond, and Y is

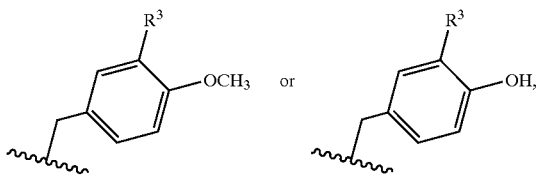

where R³ is H, halo or alkyl.

8. Y is:

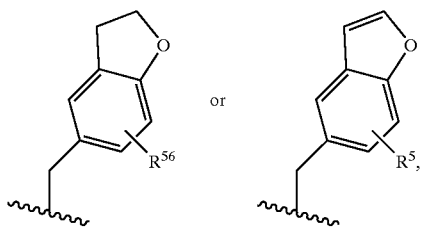

where,
R⁵⁶ is H, halo, alkyl or cyano; and
R⁵ is halo, alkyl or cyano.

9.
(a) R$^a$ is alkyl or R²⁴-alkyl-, and R$^b$ and R$^c$ are each H, where R²⁴ is defined in the summary of the invention; or
(b) R$^a$ and R$^b$, together with the carbon to which they are both attached, form a 5- or 6-membered ring, and R$^c$ is H; or
(c) R$^a$ and R$^c$, together with the respective carbons to which they are attached, form a 5-membered ring, and R$^b$ is H; or
(d) R$^a$, R$^b$ and R$^c$ are each H.

10. R⁸ is alkyl or hydrogen.

11. X is —NR⁸—, Y is defined in section (i) or (ii) of the summary of the invention, and R² is a group defined by the formula (III.1):

(III.1)

where,
R⁸ is H or alkyl;
R⁹, R¹⁰ and R¹¹, independently of one another, are selected from the group consisting of H, cycloalkyl, heterocycloalkyl, carboxyl, carboxamido, alkoxycarbonyl, aryloxycarbonyl, oximino, alkyl, R³²-alkyl- and R²⁶, where
R³² is cycloalkyl, heterocycloalkyl, carboxamido, alkoxycarbonyl, aryloxycarbonyl, hydroxy, alkoxy, amino, monoalkylamino, dialkylamino or R²⁶, and
R²⁶ is defined in the summary of the invention; or
R⁹ and R¹⁰, together with the carbon, carbons and/or heteroatom of the ring to which they are attached, form a linearly-fused or bridged bicyclic ring of 7 to 12 members, and R¹¹ is defined above; or
R¹⁰ and R¹¹ are, independently of one another, selected from the group consisting of hydroxy, alkoxy, aryloxy, acyloxy, —C(O)OR³⁴, where R³⁴ is defined in the summary of the invention, amino, alkylamino, dialkylamino, acylamino and alkylsulfonylamino, and R⁹ is defined above; or
R¹⁰ and R¹¹, together with the carbon, carbons and/or heteroatom of the ring to which they are attached, form a linearly-fused, spiro-fused or bridged bicyclic ring of 7 to 12 members, and R⁹ is defined above;
l and m are, independently of one another, each 1 to 3; and
A is —O—, —S—, —C(R⁴R¹⁶)—, —SO—, —SO₂— or —NR¹²—, where
R⁴ and R¹⁶ are, independently of one another, each selected from the group consisting of H, cycloalkyl, heterocycloalkyl, carboxyl, carboxamido, alkoxycarbonyl, aryloxycarbonyl, oximino, alkyl, R³²-alkyl- and R²⁶, where R³² is defined above and R²⁶ is defined in the summary of the invention; and
R¹² is heterocycloalkyl, R⁷, R²⁶, —COR¹³, —SO₂R¹⁴, —CO₂R¹⁴, —CONR¹³R¹⁵ or —SO₂NR³R¹⁵, where
R⁷ is defined in the summary of the invention;
R¹⁴ is alkyl, alkenyl, cycloalkyl, cycloalkylalkyl, heterocycloalkyl or R²⁶, where R²⁶ is defined in the summary of the invention; and
R¹³ and R¹⁵ are, independently of one another, each selected from the group consisting of H and R¹⁴; or
R¹³ and R¹⁵, together with the nitrogen to which they are both attached, form a 4- to 8-membered ring.

12. Embodiment number 11, where R⁹, R¹⁰ and R¹¹ are each H.

13. R² is cyclopropylamino or cyclopropylamino substituted with R⁹, R¹⁰ and R¹¹ substituents, each of which is independently defined the same as above in embodiment number 11 for the larger 4- to 8-membered carbocycles.

14.

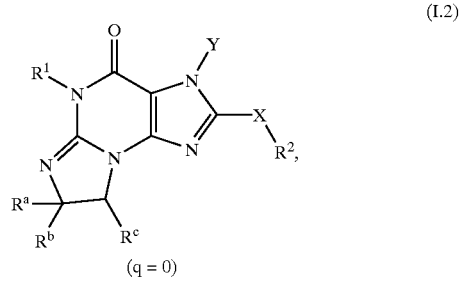

(I.2)

(q = 0)

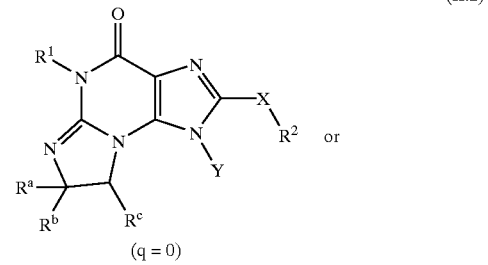

(II.2)

(q = 0)

(I.3)

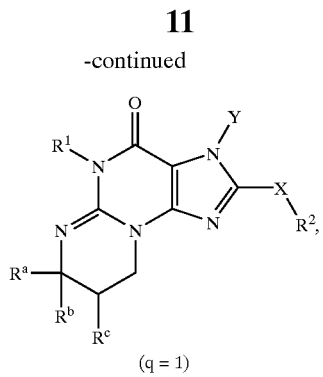

(q = 1)

where,
R$^a$, R$^b$, R$^c$, R$^1$, R$^2$, X and Y are each independently defined in the summary of the invention. Preferably, the inventive compound has the chemical structure (I.2) or (I.3).

15. Y is -Q-V, where Q and V are each independently defined in the summary of the invention.

16. Y is aralkyl substituted with at least one of nitro, aminosulfonyl, cyano, monohaloalkyl, polyhaloalkyl, other than trifluoromethyl, thiol, alkylthio, cycloalkyl, cycloalkylalkyl, —OCF$_3$ or acyloxy (e.g., —OC(O)CH$_2$CH$_3$ and —OC(O)CH(CH$_3$)$_2$.

17. Y is represented by the following structure:

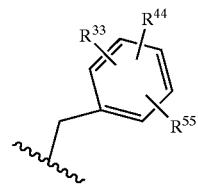

where,
at least one of R$^{33}$, R$^{44}$ and R$^{55}$, independently of one another, is nitro, aminosulfonyl, cyano, monohaloalkyl, polyhaloalkyl, other than trifluoromethyl, thiol, alkylthio, cycloalkyl, cycloalkylalkyl, —OCF$_3$ or acyloxy; and
the remainder of R$^{33}$, R$^{44}$ and R$^{55}$, independently of one another, are each hydrogen or halogen, or one of the groups defined above for the at least one of R$^{33}$, R$^{44}$ and R$^{55}$; or
two of R$^{33}$, R$^{44}$ and R$^{55}$ join together with each other to form a 4- to 7-membered aromatic or non-aromatic ring comprising at least one heteroatom, (e.g., oxygen, sulfur or nitrogen).

18. Y is represented by one of the following structures:

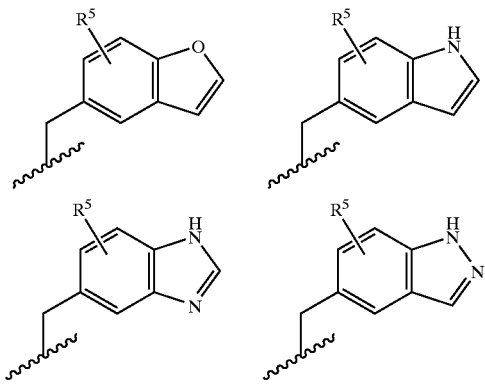

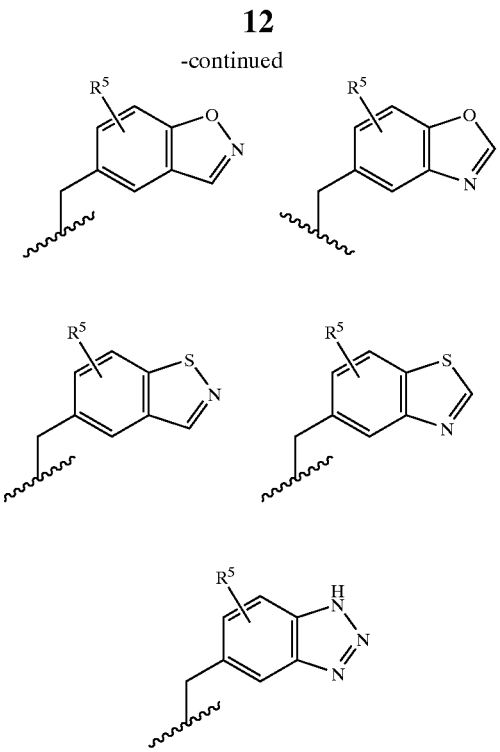

where,
R$^5$ is halogen, hydroxy, alkoxy, nitro, aminosulfonyl, cyano, monohaloalkyl, polyhaloalkyl (e.g., trihalomethyl), thiol, alkylthio, alkyl, cycloalkyl, cycloalkylalkyl, —OCF$_3$, acyloxy (e.g., —OC(O)CH$_2$CH$_2$CH$_3$) or carboxyl.

19. Y is represented by one of the following structures:

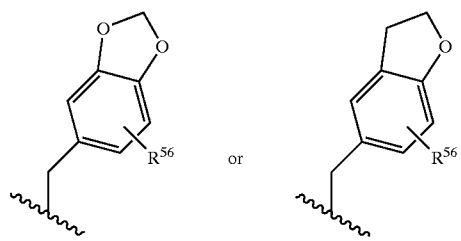

where,
R$^{56}$ is hydrogen or one of the groups defined in embodiment 18 above for R$^5$.

20. Embodiments 15, 16, 17, 18 or 19, where X is a bond.
21. X is a bond, and Y and R$^2$ are each independently defined in section (i) of the summary of the invention.
22. A compound having the formula (I.1):

(I.1)

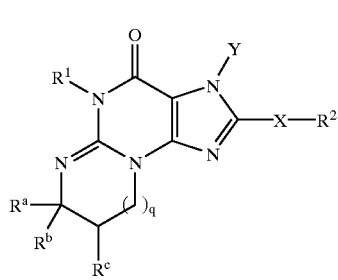

where,
q is 0 or 1;
$R^1$ is —$CH_2CH_3$;
$R^a$, $R^b$ and $R^c$ are each H; or
$R^b$ and $R^c$ are each H, and $R^a$ is

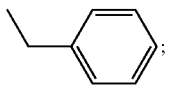

or
$R^b$ is H, and $R^a$ and $R^c$, together with the respective carbons to which they are attached, form a 5-membered ring; or
$R^c$ is H, and $R^a$ and $R^b$, together with the carbon to which they are both attached, form a 5-membered ring;
X is —NH—, and $R^2$ is

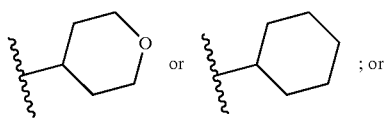

X is —C≡C—, and $R^2$ is <img phenyl> ; or

X is a bond, and $R^2$ is —C(=O)NH_2 ; and

Y is 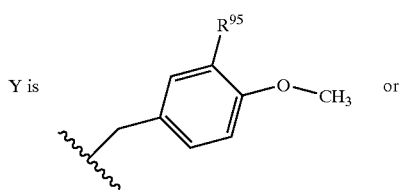

where,
$R^{95}$ is Cl or Br.

It is understood that specific substituents can be employed for purposes other than to affect the PDE V potency and/or selectivity of the inventive compound.

The compounds of formulas (I.1) and (II.1) are useful for treating urogenital diseases, such as male and female sexual dysfunction, particularly, erectile dysfunction. The inventive polycyclic guanines exhibited unexpectedly favorable properties with respect to PDE V isoenzyme activity and selectivity.

The following compounds listed in Tables I, II and III are illustrative of the invention:

TABLE I

| Compound Number | Structure |
|---|---|
| 1 | (structure with Br, OH, ethyl, tetrahydropyran-NH) |
| 2 | (structure with Cl, OH, ethyl, tetrahydropyran-NH) |
| 3 | (structure with Br on benzofuran, ethyl, Br, benzyl) |

TABLE I-continued
| Compound Number | Structure |
|---|---|
| 4 | 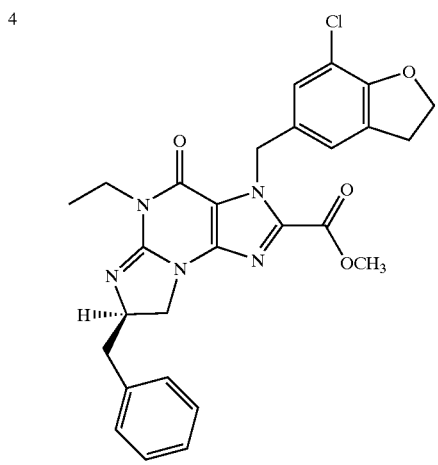 |
| 5 | 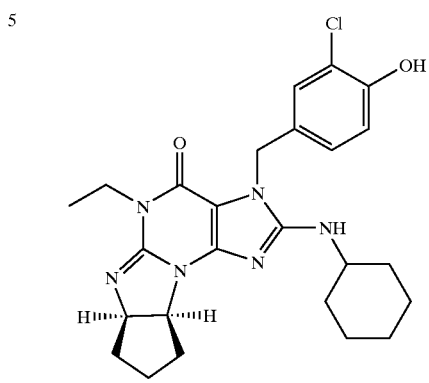 |
| 6 | 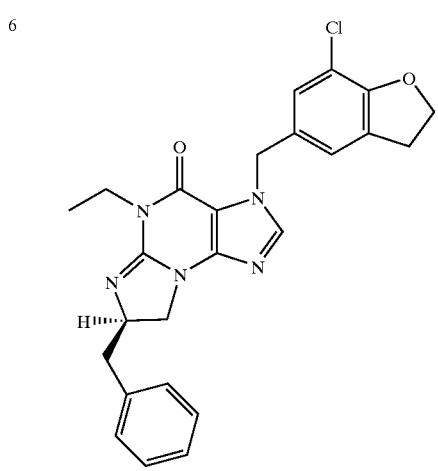 |
| 7 | 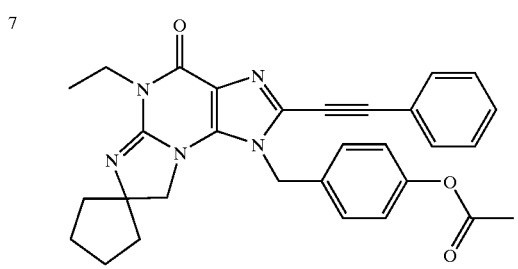 |
| 8 | 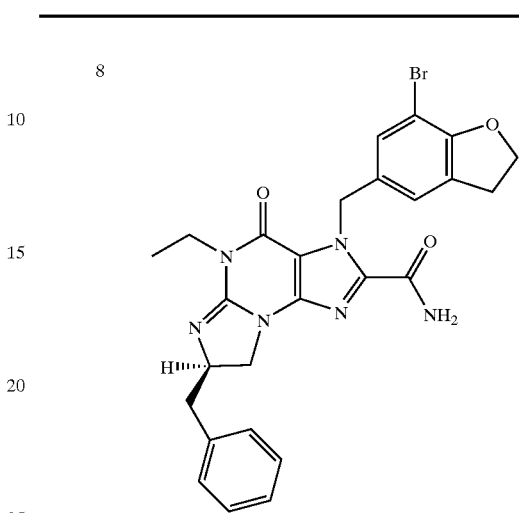 |
| 9 | 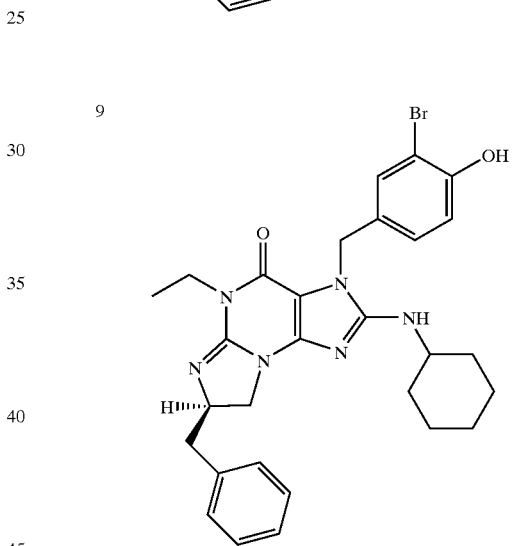 |
| 10 | 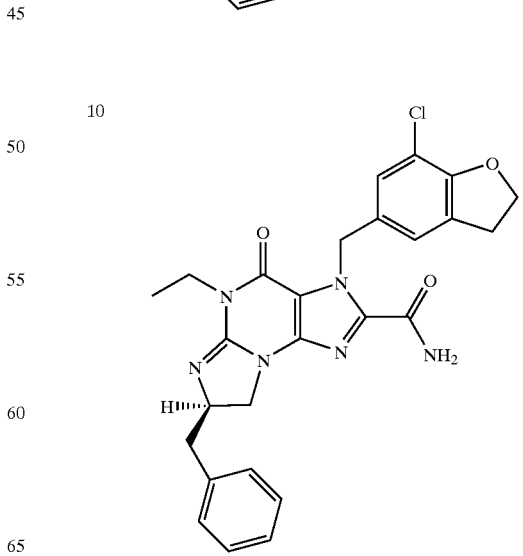 |

TABLE I-continued
| Compound Number | Structure |
|---|---|
| 11 | 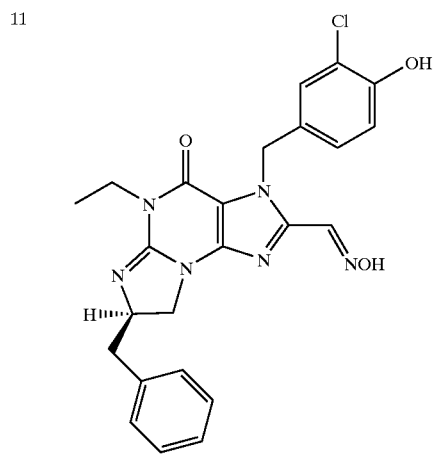 |
| 12 | 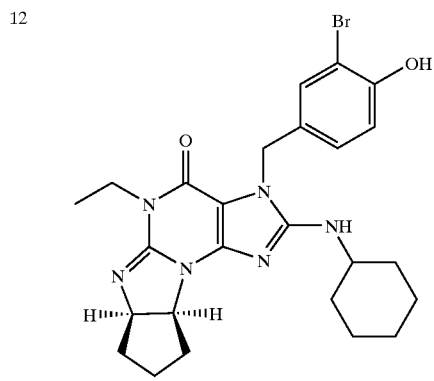 |
| 13 | 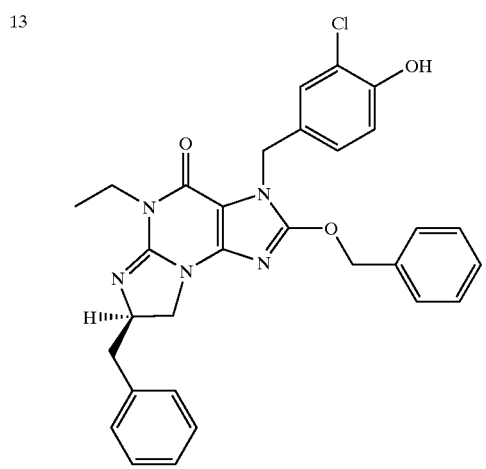 |
| 14 | 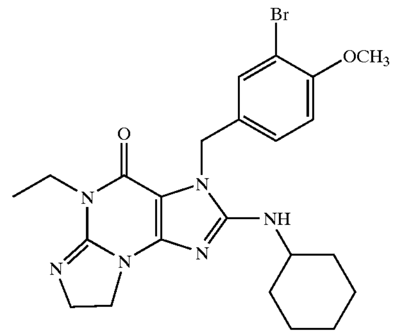 |
| 15 | 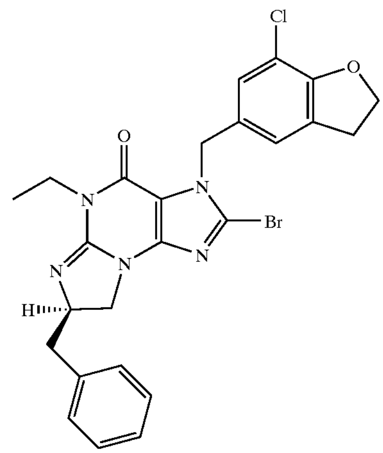 |
| 16 | 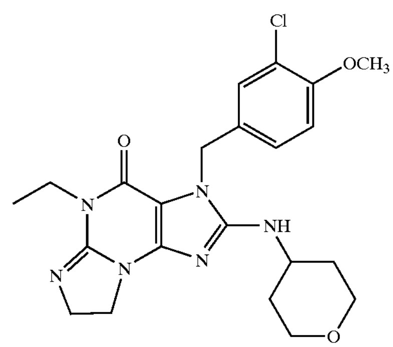 |
| 17 | 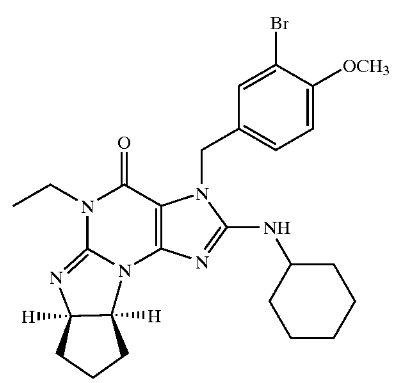 |
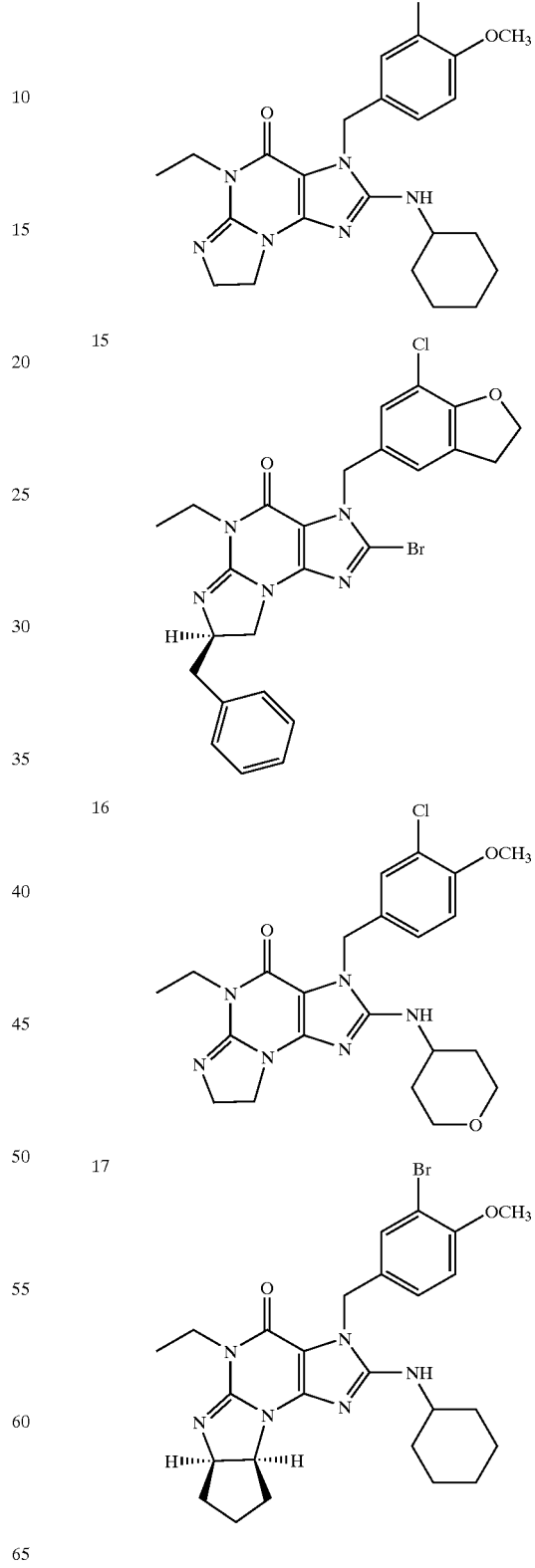

TABLE I-continued
| Compound Number | Structure |
|---|---|
| 18 | 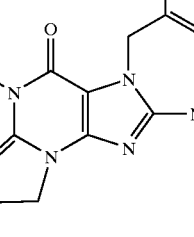 |
| 19 | 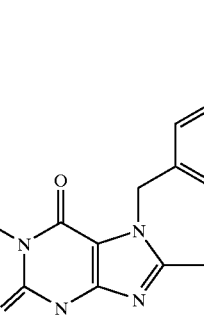 |
| 20 | 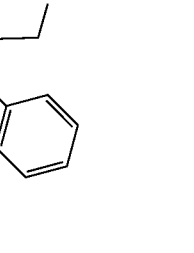 |
| 21 | 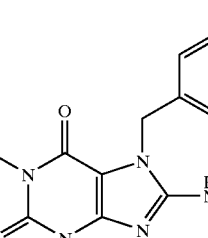 |
| 22 | 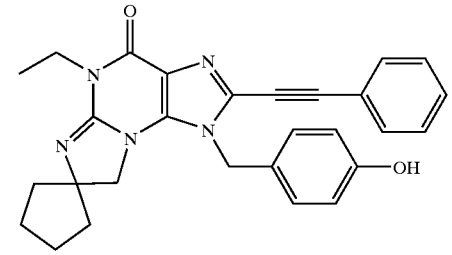 |
TABLE II
| Compound Number | Structure |
|---|---|
| 23 | 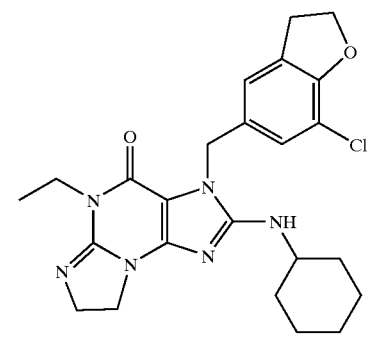 |
| 24 | 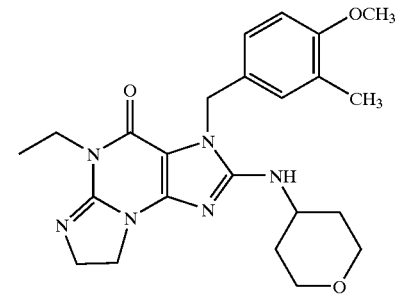 |
| 25 | 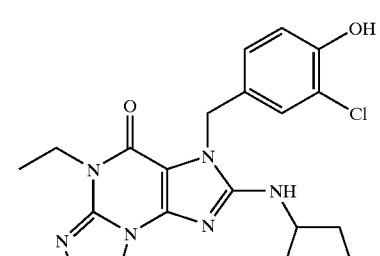 |

TABLE II-continued
| Compound Number | Structure |
|---|---|
| 26 | 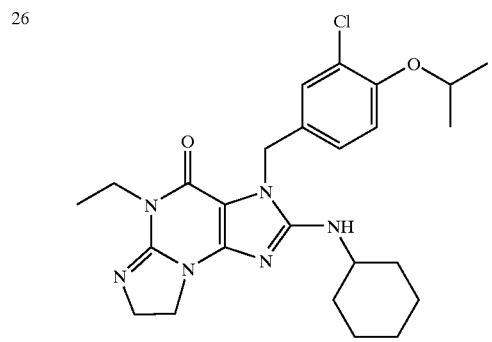 |
| 27 | 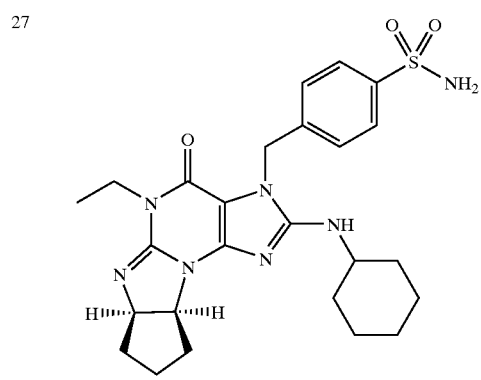 |
| 28 | 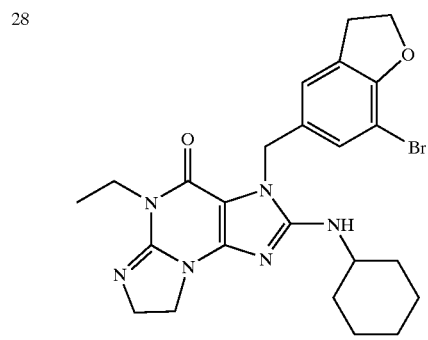 |
| 29 | 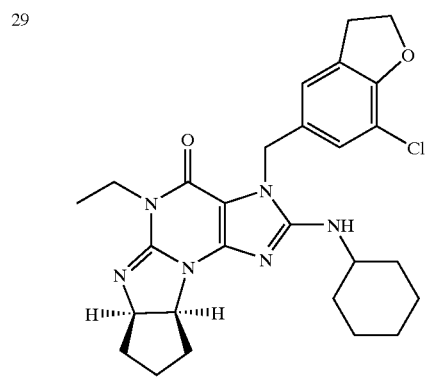 |
| 30 | |
| 31 | |
| 32 | |
| 33 | |
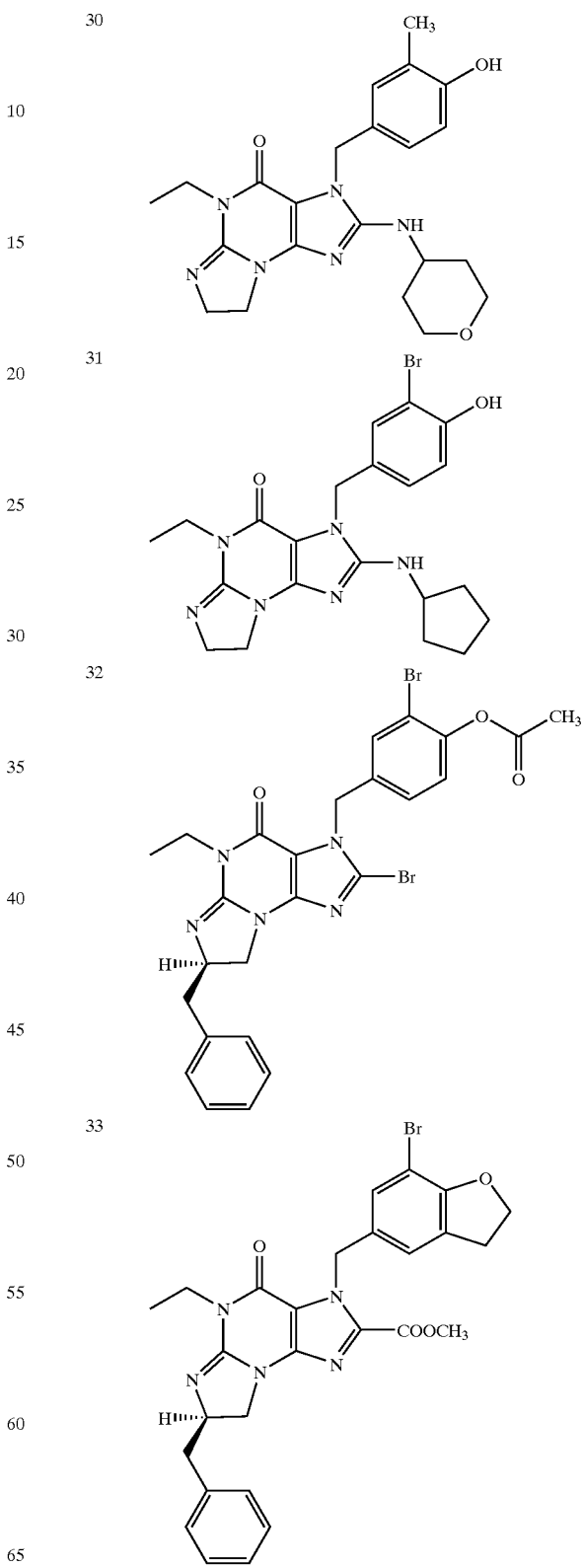

TABLE II-continued

| Compound Number | Structure |
|---|---|
| 34 | 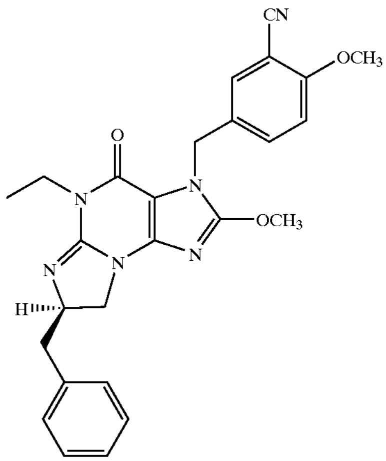 |
| 35 | 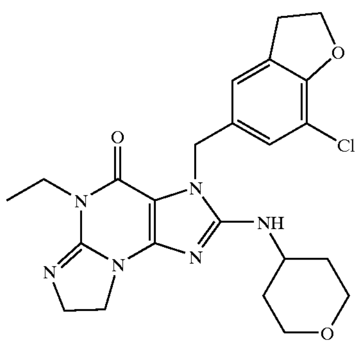 |
| 36 | 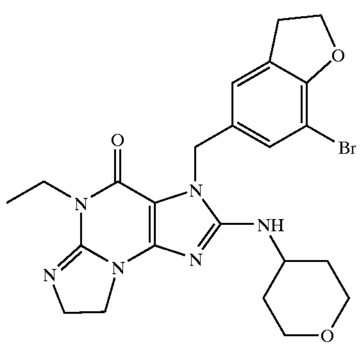 |
| 37 | 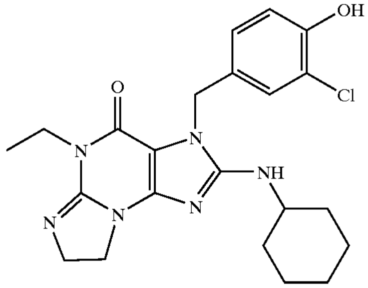 |
| 38 | |
| 39 | |
| 40 | |
| 41 | |

TABLE III
| Compound Number | Structure |
|---|---|
| 42 | 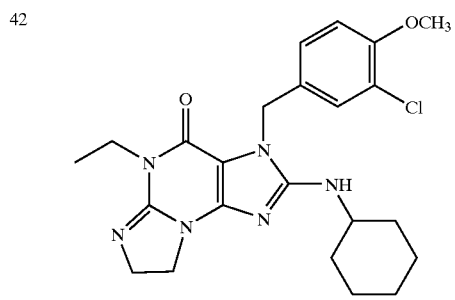 |
| 43 | 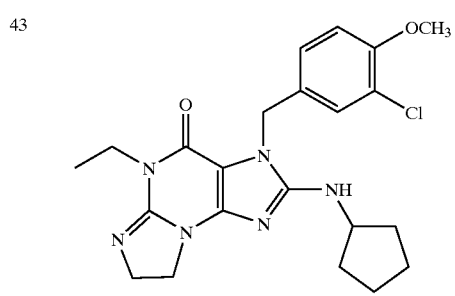 |
| 44 | 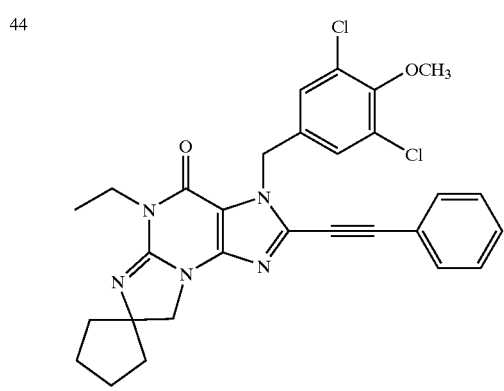 |
| 45 | 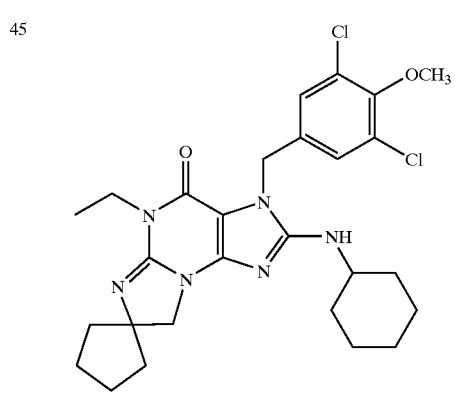 |
TABLE III-continued
| Compound Number | Structure |
|---|---|
| 46 | 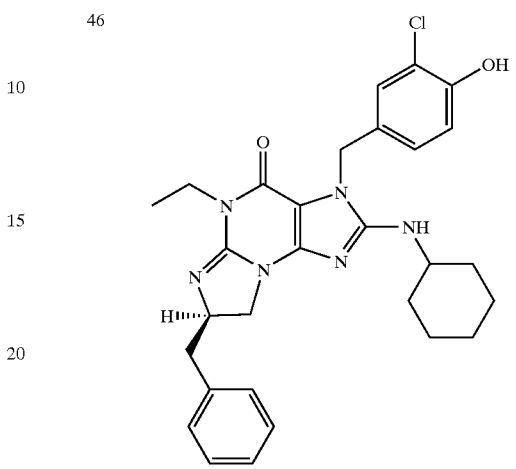 |
| 47 | 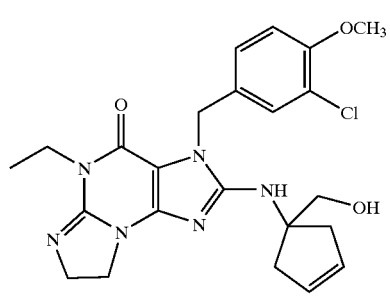 |
| 48 | 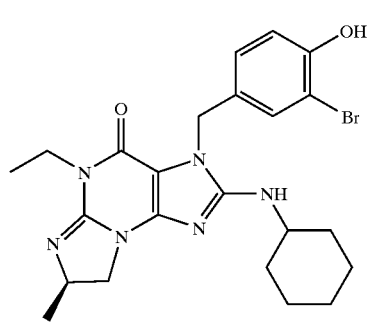 |
| 49 | 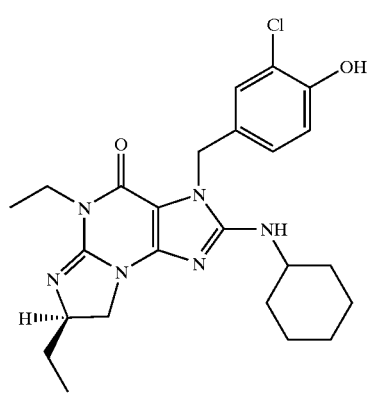 |

TABLE III-continued
| Compound Number | Structure |
|---|---|
| 50 | 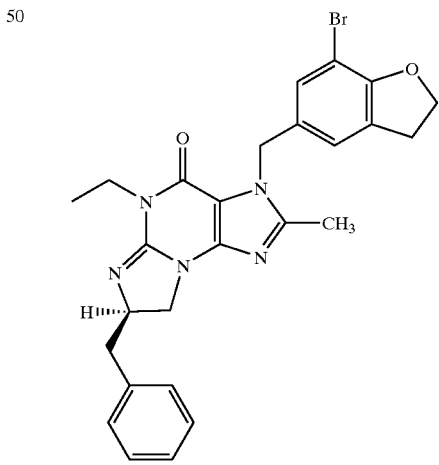 |
| 51 | 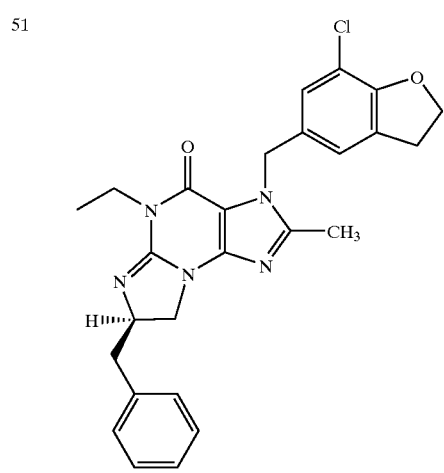 |
| 52 | 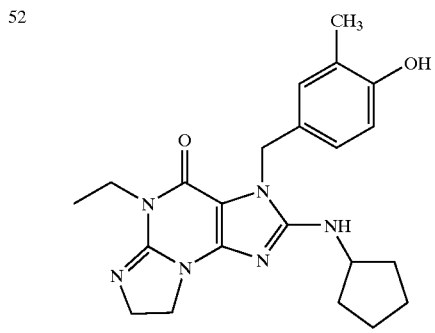 |
| 53 | 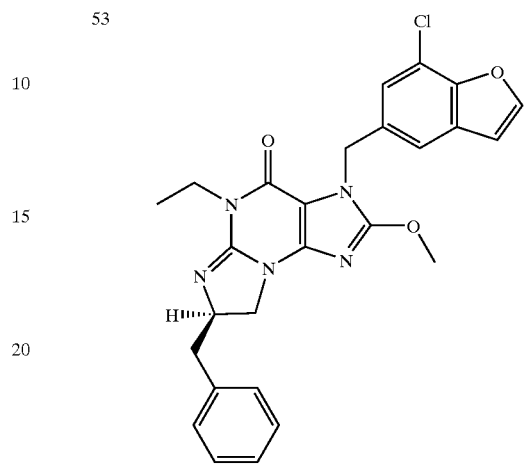 |
| 54 | 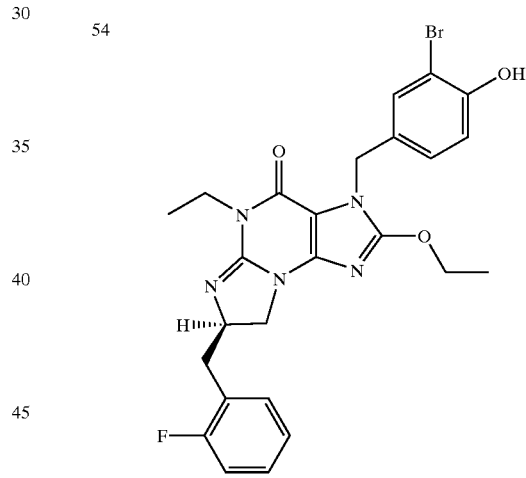 |
| 55 | 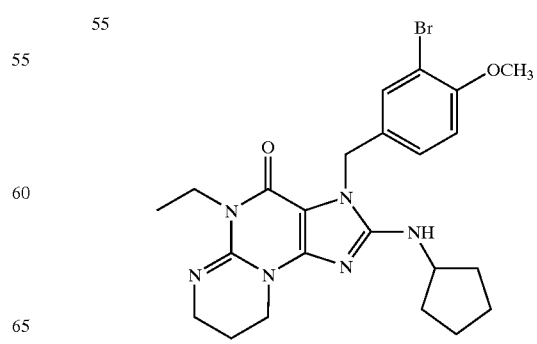 |

TABLE III-continued

| Compound Number | Structure |
|---|---|
| 56 | (structure) |
| 57 | (structure) |
| 58 | (structure) |
| 59 | (structure) |
| 60 | (structure) |
| 61 | (structure) |
| 62 | (structure) |

The compounds of the invention can be useful for inhibiting PDE V isoenzymes. Isoenzyme activities and isoenzyme selectivities for particular compounds can be evaluated in a number of ways. For instance, enzyme activity can be measured by the PDE V $IC_{50}$ value, which is the concentration (in nM) of the compound required to provide 50% inhibition of PDE V. The lower the value of $IC_{50}$, the more active is the compound.

Compounds 1–22 (Table I) had a PDE V $IC_{50}$ of <10 nM and a ratio of PDE VI $IC_{50}$/PDE V $IC_{50}$ of >150. Compounds 23–41 (Table II) had a PDE V $IC_{50}$ of between about 10 and 60 nM, and a ratio of PDE VI $IC_{50}$/PDE V $IC_{50}$ of >150. Compounds 42–61 (Table II) had a PDE V $IC_{50}$ of between about 1 and 100 nM and a ratio of PDE VI $IC_{50}$/PDE V $IC_{50}$ of between about 80 and 150 nM. Measurements on the compounds in Tables I, II and III generated data which can be grouped as follows:

Tables I, II and III

1. [PDE V $IC_{50}$]:
   A. all compounds had a PDE V $IC_{50}$ of <100 nM;
   B. compound nos. 1–22, 34, 42–44, 54 and 56–59 had a PDE V $IC_{50}$ of $\leq$10 nM; and
   C. compound nos. 6–20, 22, 42–44, 54, 56 and 58 had a PDE V $IC_{50}$ of $\leq$5 nM;
2. [PDE VI $IC_{50}$]:
   D. all compounds had a PDE VI $IC_{50}$ within the range of from $\geq$170 nM to 10,000 nM;
   E. compound nos. 7–19, 22, 42–44, 54 and 56–59 had a PDE VI $IC_{50}$ within the range of from $\geq$170 nM to $\leq$1,000 nM; and F. compound nos. 1–6, 20, 21, 23–41, 45–53, 55 and 60–62 had a PDE VI $IC_{50}$ within the range of from >1,000 nM to >10,000 nM.

Once the PDE V $IC_{50}$ and PDE VI $IC_{50}$ values have been measured, one can calculate the ratio of PDE VI $IC_{50}$/PDE V $IC_{50}$, which is an indicator of enzyme selectivity—the higher the ratio, the more selective is the compound to inhibiting PDE V enzyme relative to PDE VI enzyme. Calculating the ratios for the compounds in Tables I, II and III gave the following results:

3. [PDE VI $IC_{50}$/PDEV $IC_{50}$]:
   G. all compounds had a PDE VI $IC_{50}$/PDE V $IC_{50}$ ratio of $\geq 75$;
   H. compound nos. 42–44, 46, 47, 51–53, 56, 59 and 61 had a PDE VI $IC_{50}$/PDE V $IC_{50}$ ratio within the range of from $\geq 75$ to 100;
   I. compound nos. 3, 7, 9, 11, 13, 14, 19, 23–29, 38, 40, 41, 45, 48–50, 54, 55, 57, 58 & 60 had a PDE VI $IC_{50}$/PDE V $IC_{50}$ ratio within the range of from >100 to 200;
   J. compound nos. 5, 6, 8, 16, 17, 21, 31–33 and 39 had a PDE VI $IC_{50}$/PDE V $IC_{50}$ ratio within the range of from >200 to 300;
   K. compound nos. 4, 10, 15, 18 and 20 had a PDE VI $IC_{50}$/PDE V $IC_{50}$ ratio within the range of from >300 to 400;
   L. compound nos. 1, 12, 22 and 37 had a PDE VI $IC_{50}$/PDE V $IC_{50}$ ratio within the range of from >400 to 500;
   M. compound no. 34 had a PDE VI $IC_{50}$/PDE V $IC_{50}$ ratio within the range of from >500 to 600; and
   N. compound no. 2 had a PDE VI $IC_{50}$ /PDE V $IC_{50}$ ratio of >600.

4. [PDE V $IC_{50}$ and PDE VI $IC_{50}$/PDE V $IC_{50}$]
   O. compound nos. 1–22, 34, 42–44, 54 and 56–59 had a PDE V $IC_{50}$ of <100 nM and a PDE VI $IC_{50}$/PDE V $IC_{50}$ ratio of $\leq 90$;
   P. compounds nos. 1–41 had a PDE V $IC_{50}$ of <100 nM and a PDE VI $IC_{50}$/PDE V $IC_{50}$ ratio of >140;
   Q. compounds nos. 1–22 had a PDE V $IC_{50}$ of $\leq 8$ nM and a PDE VI $IC_{50}$/PDE V $IC_{50}$ ratio of >140;
   R. compound nos. 6–20 and 22 had a PDE V $IC_{50}$ of $\leq 5$ nM and a PDE VI $IC_{50}$/PDE V $IC_{50}$ ratio of >140;
   S. compound nos. 5, 6, 8, 16 and 17 had a PDE V $IC_{50}$ of $\leq 6$ nM and a PDE VI $IC_{50}$/PDE V $IC_{50}$ ratio of from >200 to 300;
   T. compound nos. 4, 10, 15, 18 and 20 had a PDE V $IC_{50}$ of $\leq 6$ nM and a PDE VI $IC_{50}$/PDEV $IC_{50}$ ratio of from >300 to 400;
   U. compound nos. 1, 12 and 22 had a PDE V $IC_{50}$ of $\leq 8$ nM and a PDE VI $IC_{50}$/PDE V $IC_{50}$ ratio of from >400 to 500;
   V. compound no. 34 had a PDE V $IC_{50}$ of about 10 nM and a PDE VI $IC_{50}$/PDE V $IC_{50}$ ratio of from >500 to 600;
   W. compound no. 2 had a PDE V $IC_{50}$ of <8 nM and a PDE VI $IC_{50}$/PDE V $IC_{50}$ ratio of >600;
   X. compound no. 30 had a PDE V $IC_{50}$ of about 52 nM, a PDE VI $IC_{50}$ of >10,000 nM and a PDE VI $IC_{50}$/PDE V $IC_{50}$ ratio of >190; and
   Y. compound nos. 35 and 36 had a PDE V $IC_{50}$ of about 18 nM, a PDE VI $IC_{50}$ of >10,000 nM and a PDE VI $IC_{50}$/PDE V $IC_{50}$ ratio of >500.

As can be seen from the data, compounds having the formula (I.1) or (II.1) are potent (as measured by PDE V $IC_{50}$) and selective (as measured by PDE VI $IC_{50}$/PDE V $IC_{50}$) PDE V inhibitors. The most potent compounds of the invention, as measured by a PDE V $IC_{50}$ of about $\leq 10$ nM are those found in Table I (compounds 1–22). Preferably, the compounds have a PDE V $IC_{50}$ of between >0 nM and about 5 nM. Preferred selective compounds have a PDE VI $IC_{50}$/PDE V $IC_{50}$ ratio of $\geq$ about 140. More preferred compounds of the invention have a PDE V $IC_{50}$ of between >0 nM and about 5 nM and a PDE VI $IC_{50}$/PDE V $IC_{50}$ ratio of $\geq$ about 140. For example, compound number 16 has a PDE V $IC_{50}$ of about 1.5 nM and a PDE VI $IC_{50}$/PDE V $IC_{50}$ ratio of about 250. A skilled worker in the art would find the biological data significant, and along with the pharmaceutical properties of compositions comprising the inventive compounds, would find therapeutic uses for the inventive compounds in a number of applications, some of which are specified herein.

In one embodiment, preferred compounds of the invention include compounds nos. 1–22, 24, 25, 31–36, 40, 42–44, 48, 49 and 53–59. More preferred compounds of the invention include nos. 1–22, 34, 42–44, 49, 54 and 56–59. Yet, even more preferred compounds of the invention include compound nos. 1–22, 54, 57 and 58. The most preferred compounds of the invention include compound nos. 1, 4–20 and 22, especially, compound nos. 1, 4–6, 8, 10, 12, 15–18 and 20–22, more especially, compound nos. 10, 12, 15–18, 20 and 22, most especially, compound nos. 16–18, 20 and 22.

In one embodiment of the invention, preferred compounds of the invention can be represented by formula (I.1) under the following parameters:

(I.1)

where,
q = 0 or 1;
$R^1$ = —$CH_2CH_3$;
Y = where,
$R^{190}$ = —Br or —Cl; and
$R^{191}$ = —$OCH_3$ or —OH;
X is absent, and $R^2$ = —H, —Br or —C(O)$NH_2$; or
X is present and is a —NH— group, and
$R^2$ = and
$R^a$ = $R^b$ = $R^c$ = —H; or
$R^a$ = —H, and $R^b$ and $R^c$, together with the respective carbons to which they are attached, form a 5-membered ring; or
$R^a$ = $R^c$ = —H, and $R^b$ =

In one embodiment of the invention, preferred compounds of the invention include the following structures, which can be named as follows:

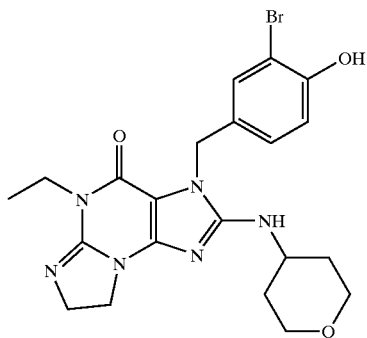

3-[(3-BROMO-4-HYDROXYPHENYL)METHYL]-5-ETHYL-7,8-
DIHYDRO-2-[(TETRAHYDRO-2H-PYRAN-4-YL)AMINO]-3H-
IMIDAZO[2,1-b]PURIN-4(5H)-ONE

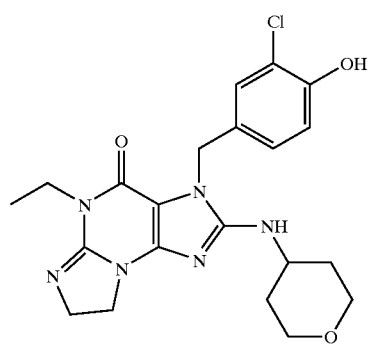

3-[(3-CHLORO-4-HYDROXYPHENYL)METHYL]-5-ETHYL-7,8-
DIHYDRO-2-[(TETRAHYDRO-2H-PYRAN-4-YL)AMINO]-3H-
IMIDAZO[2,1-b]PURIN-4(5H)-ONE

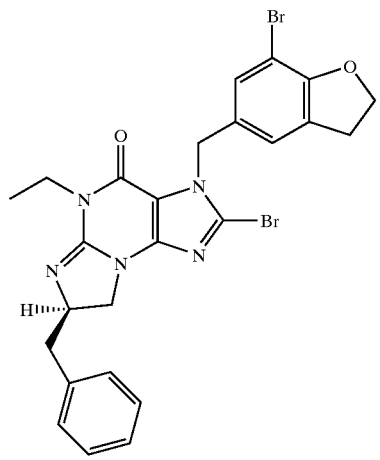

2-BROMO-3-[(7-BROMO-2,3-DIHYDRO-5-
BENZOFURANYL)METHYL]-5-ETHYL-7,8-DIHYDRO-7(R)-
(PHENYLMETHYL)-3H-IMIDAZO[2,1-b]PURIN-4(5H)-ONE

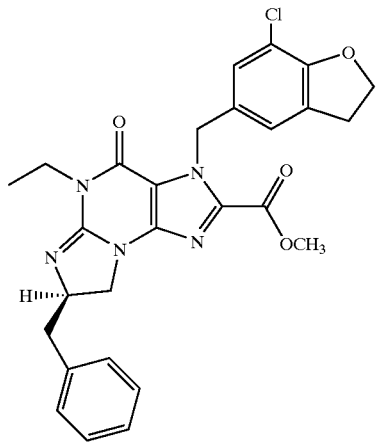

METHYL 3-[(7-CHLORO-2,3-DIHYDRO-5-
BENZOFURANYL)METHYL]-5-ETHYL-4,5,7,8-
TETRAHYDRO-4-OXO-7(R)-(PHENYLMETHYL)-3H-
IMIDAZO[2,1-b]PURINE-2-CARBOXYLATE

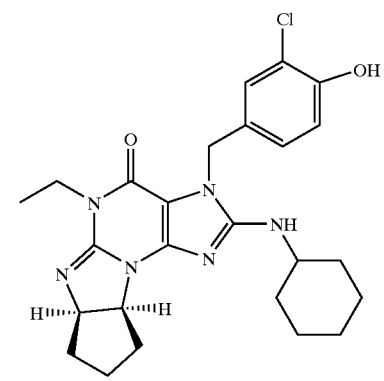

3-[(3-CHLORO-4-HYDROXYPHENYL)METHYL]-2-
(CYCLOHEXYLAMINO)-5-ETHYL-5,6a(R),7,8,9,9a(S)-
HEXAHYDROCYCLOPENT[4,5]IMIDAZO[2,1-b]PURIN-4(3H)-ONE

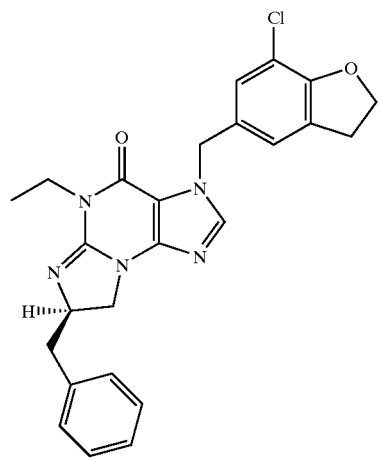

3-[(7-CHLORO-2,3-DIHYDRO-5-BENZOFURANYL)METHYL]-5-
ETHYL-7,8-DIHYDRO-7(R)-(PHENYLMETHYL)-3H-IMIDAZO[2,1-
b]PURIN-4(5H)-ONE

-continued

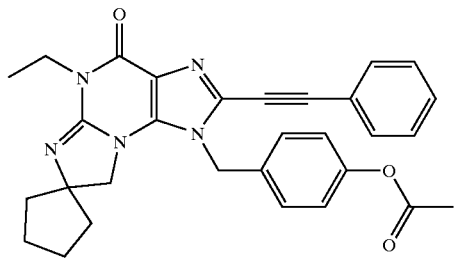

1'-[[4-(ACETYLOXY)PHENYL]METHYL]-5'-ETHYL-2'-
(PHENYLETHYNL)-SPIRO[CYCLOPENTANE-1,7'(8'H)-
[1H]IMIDAZO[2,1-b]PURIN]-4'(5'H)-ONE

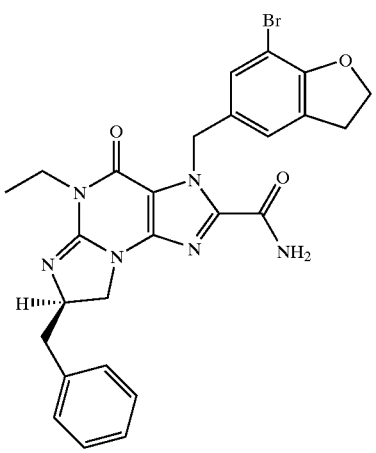

3-[(7-BROMO-2,3-DIHYDRO-5-BENZOFURANYL)
METHYL]-5-ETHYL-4,5,7,8-TETRAHYDRO-4-OXO-7(R)-
(PHENYLMETHYL)-3H-IMIDAZO[2,1-b]PURINE
-2-CARBOXAMIDE

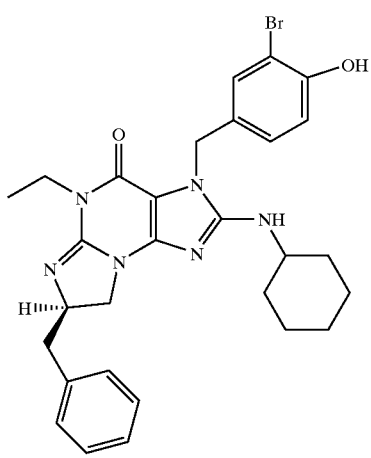

3-[(3-BROMO-4-HYDROXYPHENYL)METHYL]-2-
(CYCLOHEXYLAMINO)-5-ETHYL-7,8-DIHYDRO-7(R)-
(PHENYLMETHYL)-3H-IMIDAZO[2,1-b]PURIN-4(5H)-ONE

-continued

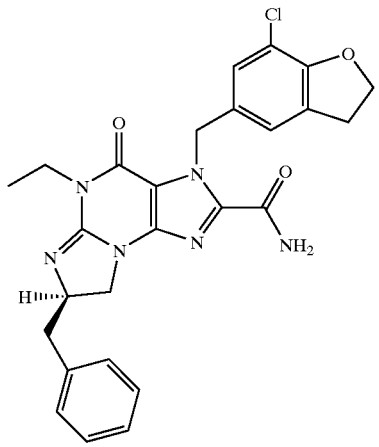

3-[(7-CHLORO-2,3-DIHYDRO-5-BENZOFURANYL)
METHYL]-5-ETHYL-4,5,7,8-TETRAHYDRO-4-OXO-7(R)-
(PHENYLMETHYL)-3H-IMIDAZO[2,1-b]PURINE-2-
CARBOXAMIDE

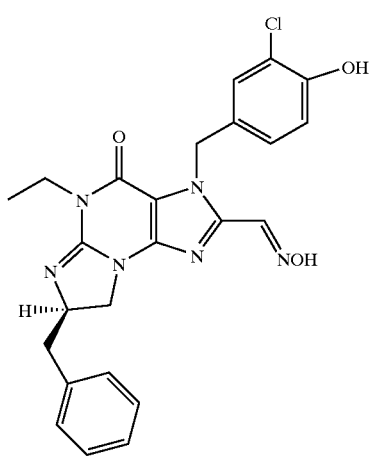

(E)-3-[(3-CHLORO-4-HYDROPHENYL)METHYL]-5-
ETHYL-4,5,7,8-TETRAHYDRO-4-OXO-7(R)-(PHENYLMETHYL)
-3H-IMIDAZO[2,1-b]PURINE-2-CARBOXALDEHYDEOXIME

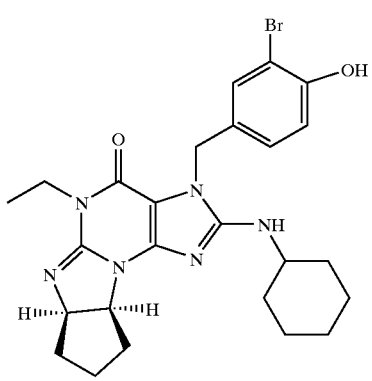

3-[(3-BROMO-4-HYDROXYPHENYL)METHYL]-2-
(CYCLOHEXYLAMINO)-5-ETHYL-5,6a(R),7,8,9,9a(S)-
HEXAHYDROCYCLOPENT[4,5]IMIDAZO[2,1-b]PURIN
-4(3H)-ONE

13

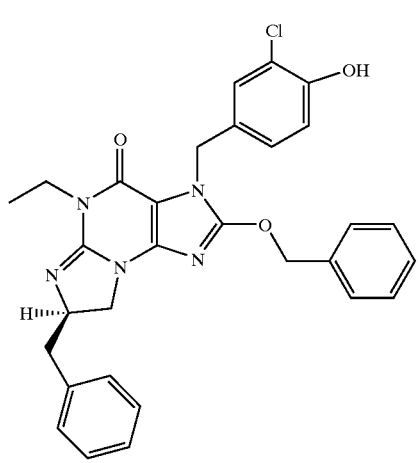

3-[(3-CHLORO-4-HYDROXYPHENYL)METHYL]-5-ETHYL-7,8-
DIHYDRO-2-(PHENYLMETHOXY)-7(R)-(PHENYLMETHYL)-3H-
IMIDAZO[2,1-b]PURIN-4(5H)-ONE

14

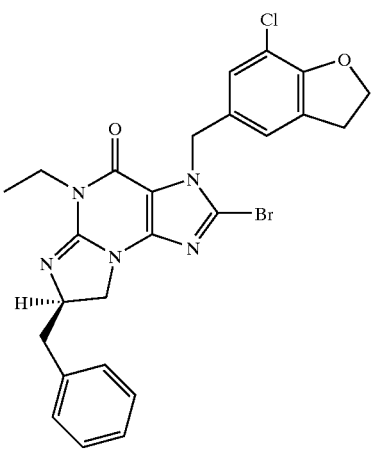

3-[(3-BROMO-4-METHOXYPHENYL)METHYL]-2-
(CYCLOHEXYLAMINO)-5-ETHYL-7,8-DIHYDRO-3H-IMIDAZO[2,1-
b]PURIN-4(5H)-ONE

15

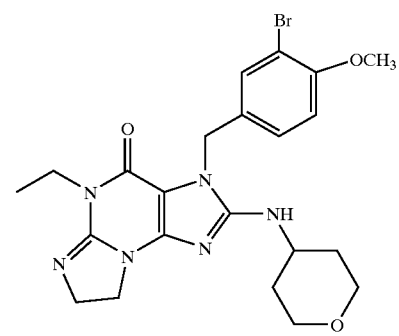

2-BROMO-3-[(7-CHLORO-2,3-DIHYDRO-5-
BENZOFURANYL)METHYL]-5-
ETHYL-7,8-DIHYDRO-7(R)-(PHENYLMETHYL)-3H-
IMIDAZO[2,1-b]PURIN-4(5H)-ONE

16

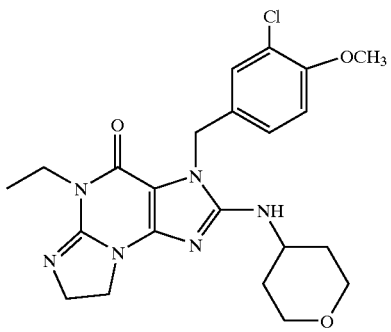

3-[(3-CHLORO-4-METHOXYPHENYL)METHYL]-5-ETHYL-7,8-
DIHYDRO-2-[(TETRAHYDRO-2H-PYRAN-4-YL)AMINO]-3H-
IMIDAZO[2,1-b]PURIN-4(5H)-ONE

17

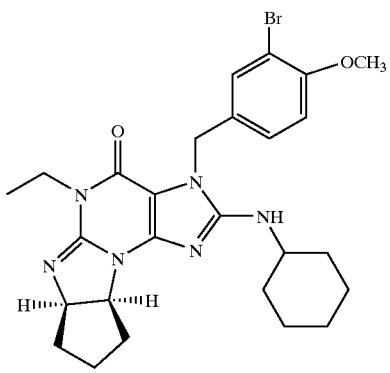

3-[(3-BROMO-4-METHOXYPHENYL)METHYL]-2-
(CYCLOHEXYLAMINO)-5-ETHYL-5,6a(R),7,8,9,9a(S)-
HEXAHYDROCYCLOPENT[4,5]IMIDAZO[2,1-b]PURIN
-4(3H)-ONE

18

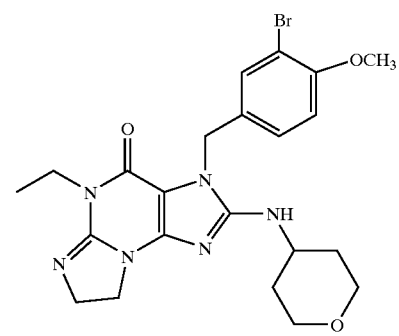

3-[(3-BROMO-4-METHOXYPHENYL)METHYL]-5-ETHYL-7,8-
DIHYDRO-2-[(TETRAHYDRO-2H-PYRAN-4-YL)AMINO]-3H-
IMIDAZO[2,1-b]PURIN-4(5H)-ONE

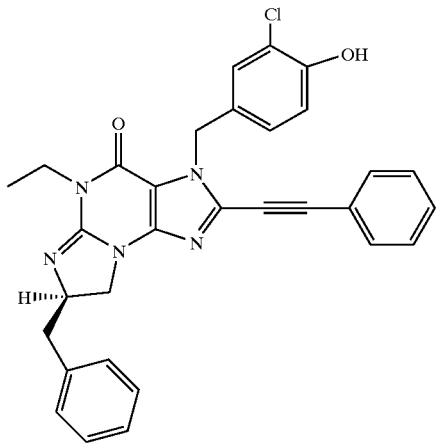

3-[(3-CHLORO-4-HYDROXYPHENYL)METHYL]-5-
ETHYL-7,8-DIHYDRO-2-(PHENYLETHYNYL)-7(R)-
(PHENYLMETHYL)-3H-IMIDAZO[2,1-b]PURIN-4(5H)-ONE

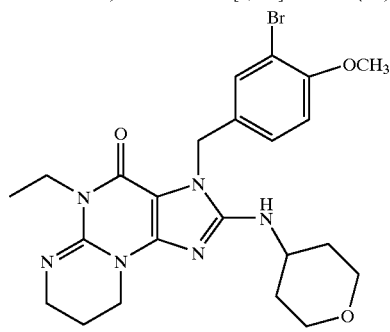

3-[(3-BROMO-4-METHOXYPHENYL)METHYL]-5-
ETHYL-5,7,8,9-TETRAHYDRO-2-[(TETRAHYDRO-2H-
PYRAN-4-YL)AMINO]PYRIMIDO[2,1-b]PURIN-4(3H)-ONE

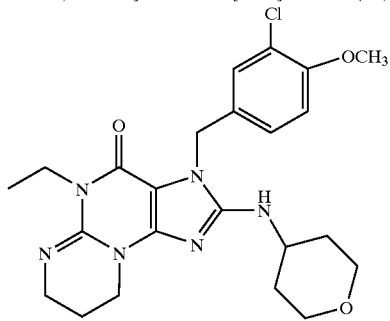

3-[(3-CHLORO-4-METHOXYPHENYL)METHYL]-5-
ETHYL-5,7,8,9-TETRAHYDRO-2-[(TETRAHYDRO-2H-
PYRAN-4-YL)AMINO]PYRIMIDO[2,1-b]PURIN-4(3H)-ONE

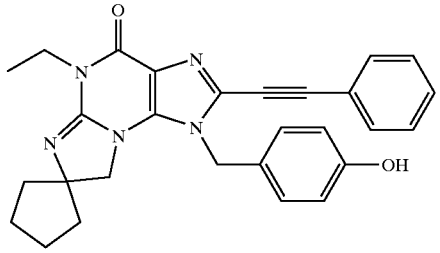

5'-ETHYL-1'-[(4-HYDROXYPHENYL)METHYL]-2'-
(PHENYLETHYNYL)-SPIRO[CYCLOPENTANE-1,7'(8'H)-
[1H]IMIDAZO[2,1-b]-PURIN]-4'(5'H)–ONE

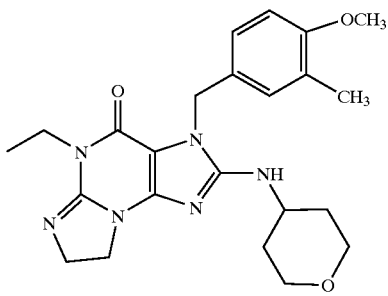

5-ETHYL-7,8-DIHYDRO-3-[(4-METHOXY-3-
METHYLPHENYL)METHYL]-2-[(TETRAHYDRO-2H-PYRAN-4-
YL)AMINO]-3H-IMIDAZO[2,1-b]PURIN-4(5H)-ONE

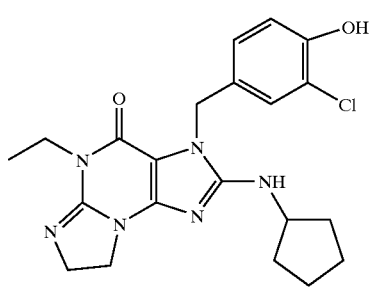

3-[(3-CHLORO-4-HYDROXYPHENYL)METHYL]-2-
(CYCLOPENTYLAMINO)-5-ETHYL-7,8-DIHYDRO-3H-IMIDAZO
[2,1-b]PURIN-4(5H)-ONE

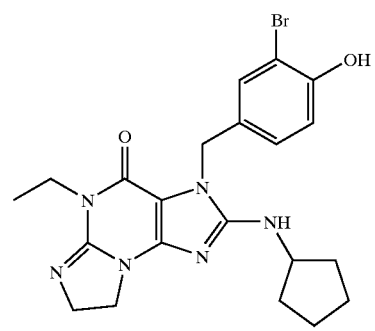

3-[(3-BROMO-4-HYDROXYPHENYL)METHYL]-2-
(CYCLOPENTYLAMINO)-5-ETHYL-7,8-DIHYDRO-3H-IMIDAZO
[2,1-b]PURIN-4(5H)-ONE

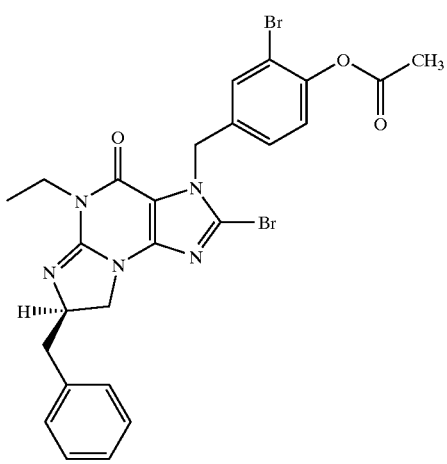

3-[[4-ACETYLOXY)-3-BROMOPHENYL]METHYL]-2-BROMO-5-ETHYL-7,8-DIHYDRO-7(R)-(PHENYLMETHYL)-3H-IMIDAZO[2,1-b]PURIN-4(5H)-ONE

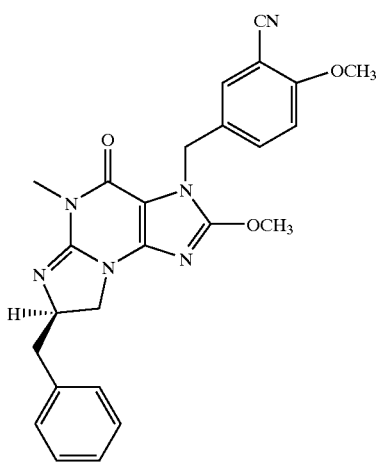

METHYL 3-[(7-BROMO-2,3-DIHYDRO-5-BENZOFURANYL)METHYL]-5-ETHYL-4,5,7,8-TETRAHYDRO-4-OXO-7(R)-(PHENYLMETHYL)-3H-IMIDAZO[2,1-b]PURINE-2-CARBOXYLATE

5-[[5-ETHYL-4,5,7,8-TETRAHYDRO-2-METHOXY-4-OXO-7(R)-(PHENYLMETHYL)-3H-IMIDAZO[2,1-b]PURIN-3-YL]METHYL]-2-METHOXYBENZONITRILE

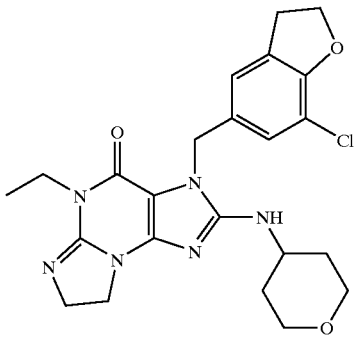

3-[(7-CHLORO-2,3-DIHYDRO-5-BENZOFURANYL)METHYL]-5-ETHYL-7,8-DIHYDRO-2-[(TETRAHYDRO-2H-PYRAN-4-YL)AMINO]-3H-IMIDAZO[2,1-b]PURIN-4(5H)-ONE

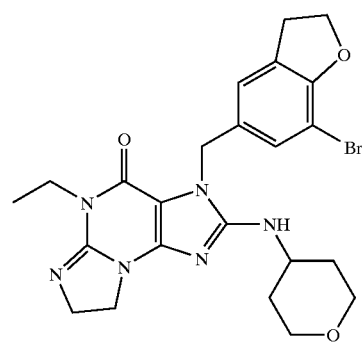

3-[(7-BROMO-2,3-DIHYDRO-5-BENZOFURANYL)METHYL]-5-ETHYL-7,8-DIHYDRO-2-[(TETRAHYDRO-2H-PYRAN-4-YL)AMINO]-3H-IMIDAZO[2,1-b]PURIN-4(5H)-ONE

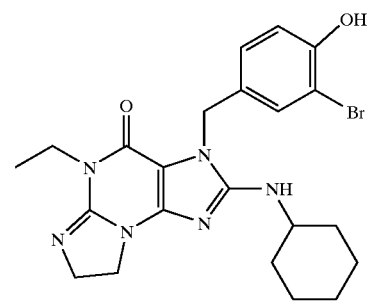

3-[(3-BROMO-4-HYDROXYPHENYL)METHYL]-2-(CYCLOHEXYLAMINO)-5-ETHYL-7,8-DIHYDRO-3H-IMIDAZO[2,1-b]PURIN-4(5H)-ONE

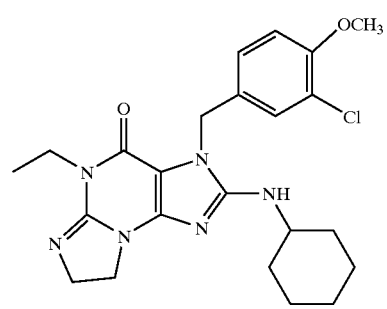

3-[(3-CHLORO-4-METHYOXYPHENYL)METHYL]-2-(CYCLOHEXYLAMINO)-5-ETHYL-7,8-DIHYDRO-3H-IMIDAZO[2,1-b]PURIN-4(5H)-ONE

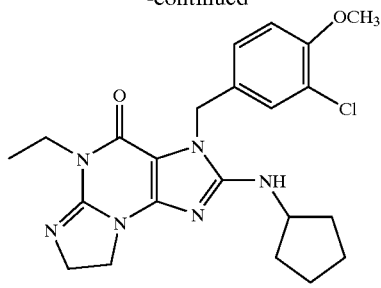

3-[(3-CHLORO-4-METHYOXYPHENYL)METHYL]-2-(CYCLOPENTYLAMINO)-5-ETHYL-7,8-DIHYDRO-3H-IMIDAZO[2,1-b]PURIN-4(5H)-ONE

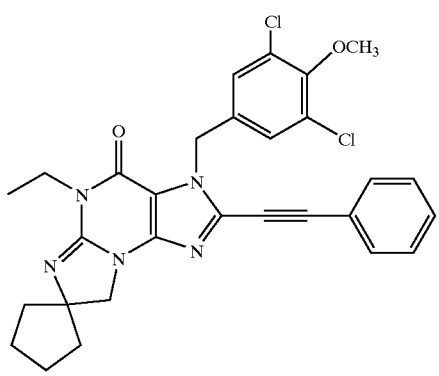

3-[(3,5-DICHLORO-4-METHYOXYPHENYL)METHYL]-5-ETHYL-2-(PHENYLETHYNYL)-SPIRO[CYCLOPENTANE]-1,7(8H)-[3H]IMIDAZO[2,1-b]-PURIN-4(5H)-ONE

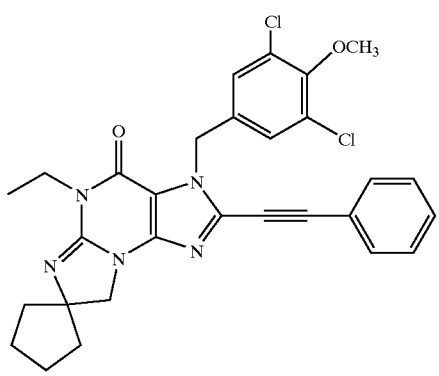

3-[(3-BROMO-4-HYDROXYPHENYL)METHYL]-2-(CYCLOPENTYLAMINO)-5-ETHYL-7,8-DIHYDRO-7(R)-METHYL-3H-IMIDAZO[2,1-b]PURIN-4(5H)-ONE

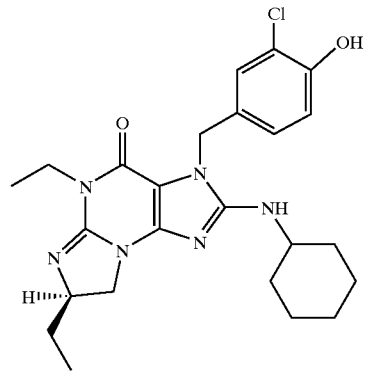

3-[(3-CHLORO-4-HYDROXYPHENYL)METHYL]-2-(CYCLOHEXYLAMINO)-5,7(R)-DIETHYL-7,8-DIHYDRO-3H-IMIDAZO[2,1-b]PURIN-4(5H)-ONE

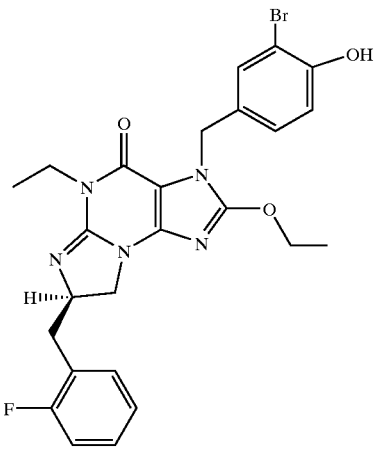

3-[(3-BROMO-4-HYDROXYPHENYL)METHYL]-2-ETHOXY-5-ETHYL-(7)R-[(2-FLUOROPHENYL)METHYL]-7,8-DIHYDRO-3H-IMIDAZO[2,1-b]PURIN-4(5H)-ONE

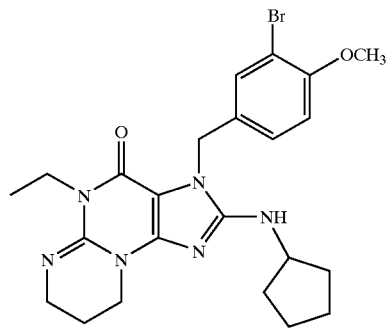

3-[(3-BROMO-4-METHOXYPHENYL)METHYL]-2-(CYCLOPENTYLAMINO)-5-ETHYL-5,7,8,9-TETRAHYDROPYRIMIDO[2,1-b]PURIN-4(3H)-ONE

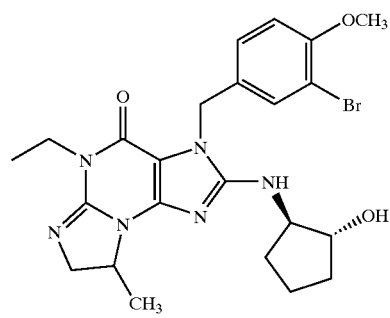

3-[(3-BROMO-4-METHOXYPHENYL)METHYL]-5-ETHYL-7,8-DIHYDRO-2-[(2(R)-HYDROXY-1(R)-(CYCLOPENTYL)AMINO]-8-METHYL-3(H)-IMIDAZO[2,1-b]PURIN-4(5H)-ONE

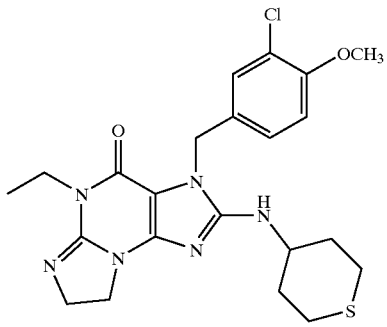

3-[(3-CHLORO-4-METHOXYPHENYL)METHYL]-5-
ETHYL-7,8-DIHYDRO-2-[(TETRAHYDRO-2H-THIOPYRAN-4-
YL)AMINO]-3H-IMIDAZO[2,1-b]PURIN-4(5H)-ONE

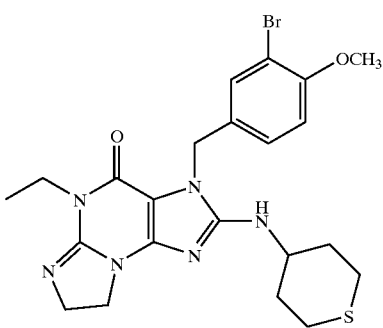

3-[(3-BROMO-4-METHOXYPHENYL)METHYL]-5-
ETHYL-7,8-DIHYDRO-2-[(TETRAHYDRO-2H-THIOPYRAN-4-
YL)AMINO]-3H-IMIDAZO[2,1-b]PURIN-4(5H)-ONE

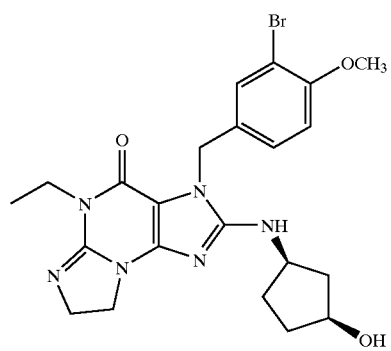

3-[(3-BROMO-4-METHOXYPHENYL)METHYL]-5-
ETHYL-7,8-DIHYDRO-2-[(3(S)-HYDROXY-1(R)-
CYCLOPENTYL)AMINO]-3H-IMIDAZO[2,1-b]PURIN-4(5H)-ONE

In one embodiment of the invention, especially preferred compounds include compound numbers 6, 8, 10, 14, 16, 18, 20, 21, 42, 57 and 58.

Specific and general procedures for producing the compounds of the invention follow below. Obvious modifications to these procedures may be undertaken by one of ordinary skill in the art. Other compounds of the invention may be produced along the same lines.

Compounds having the formula (I.1) can be prepared according to the following general schemes (Schemes 1–4):

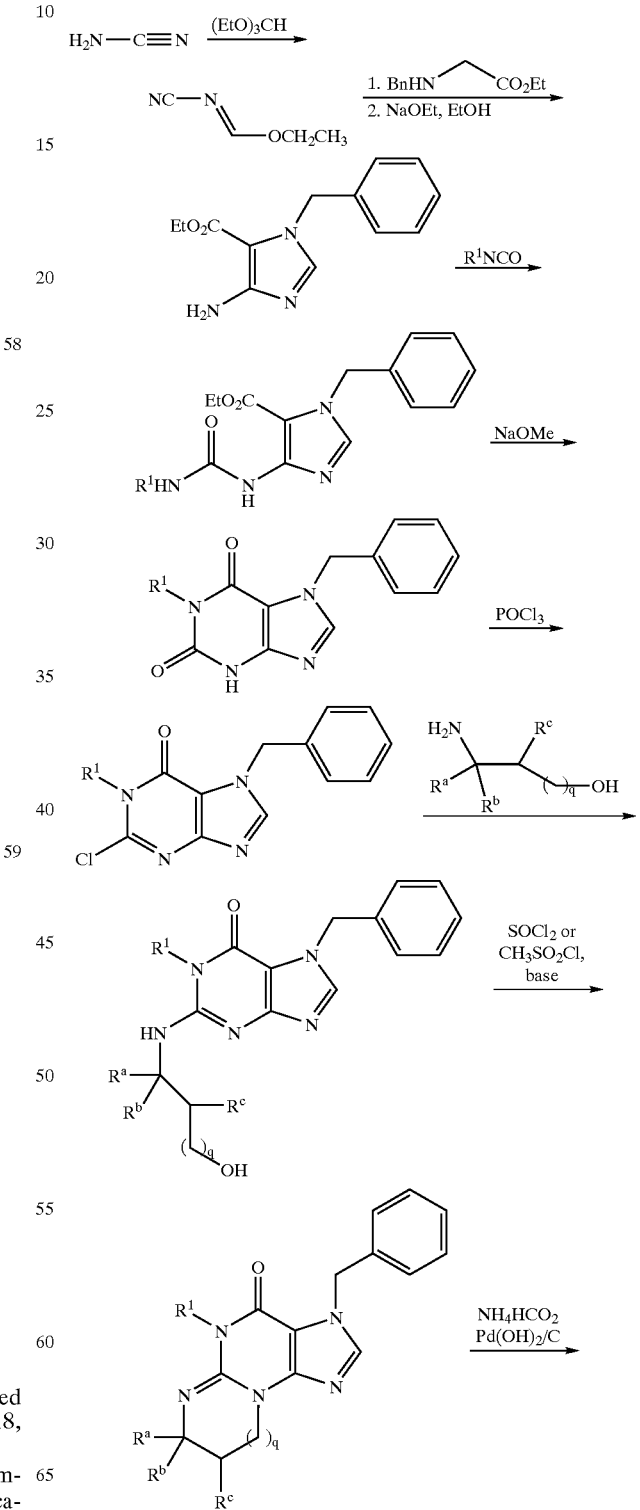

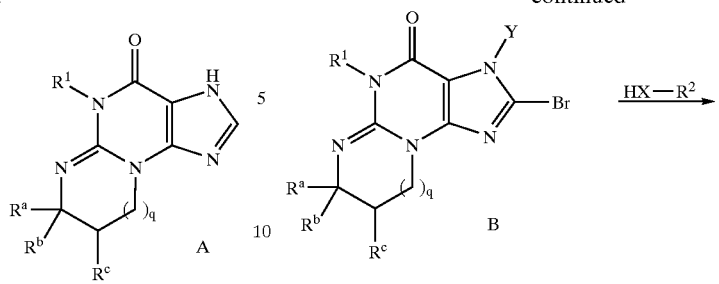
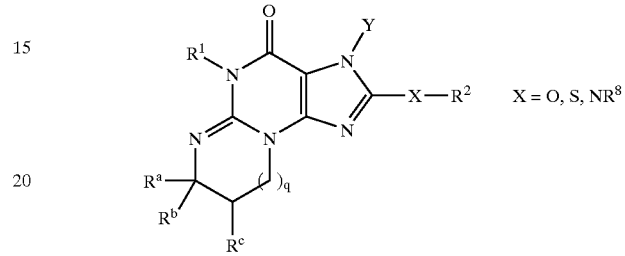
Scheme 2
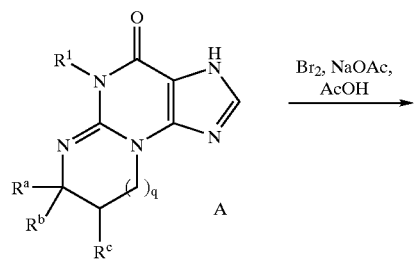
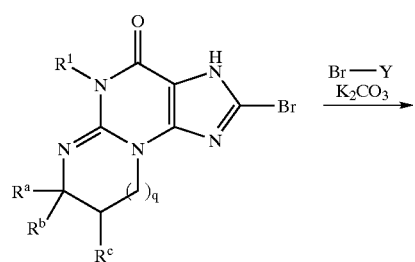
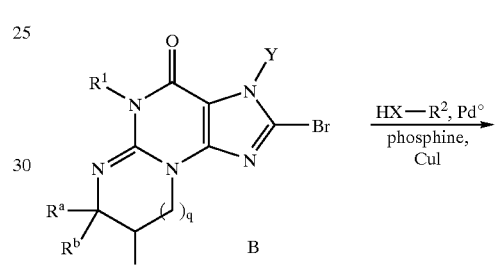
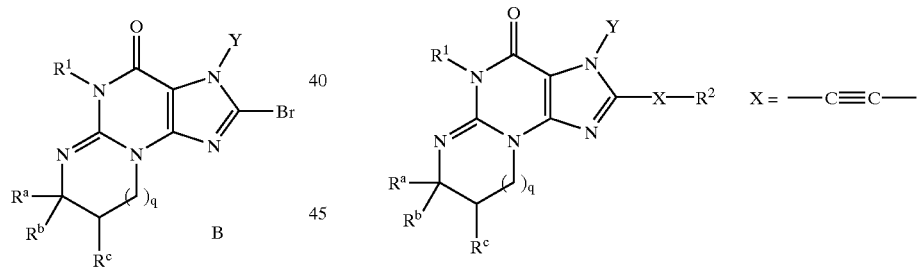
Scheme 3
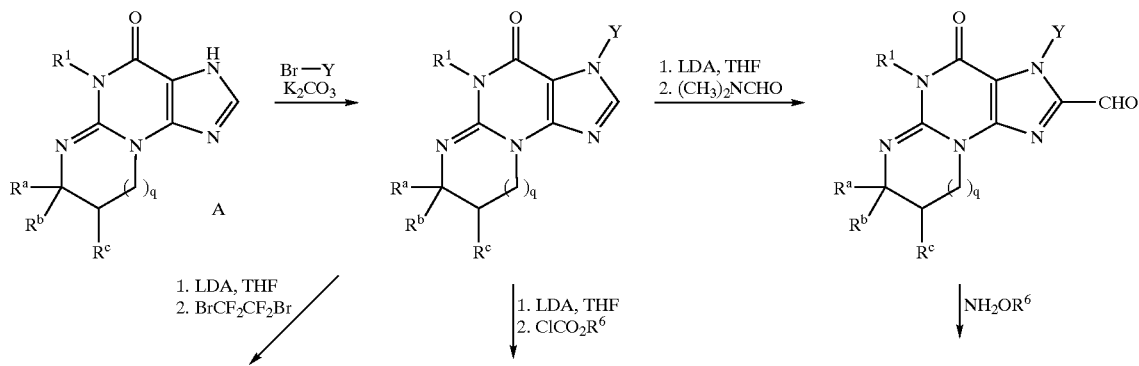

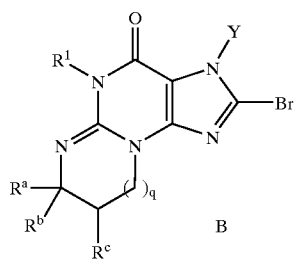
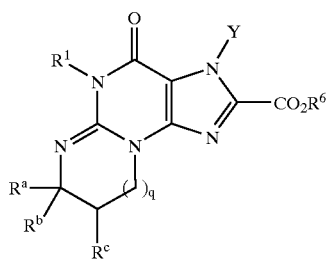
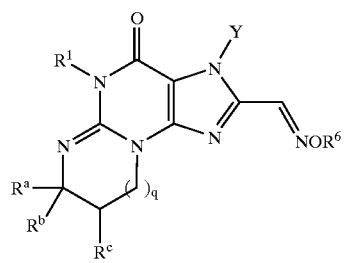
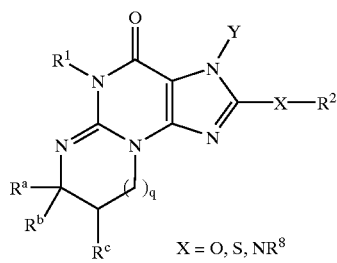
X = O, S, NR[8]
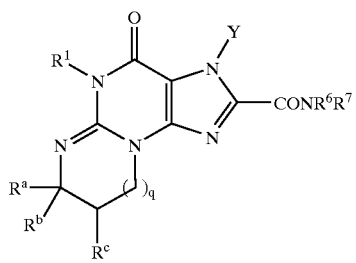
Compounds having the formula (II.1) can be prepared according to the following general scheme (Scheme 5):
Scheme 4
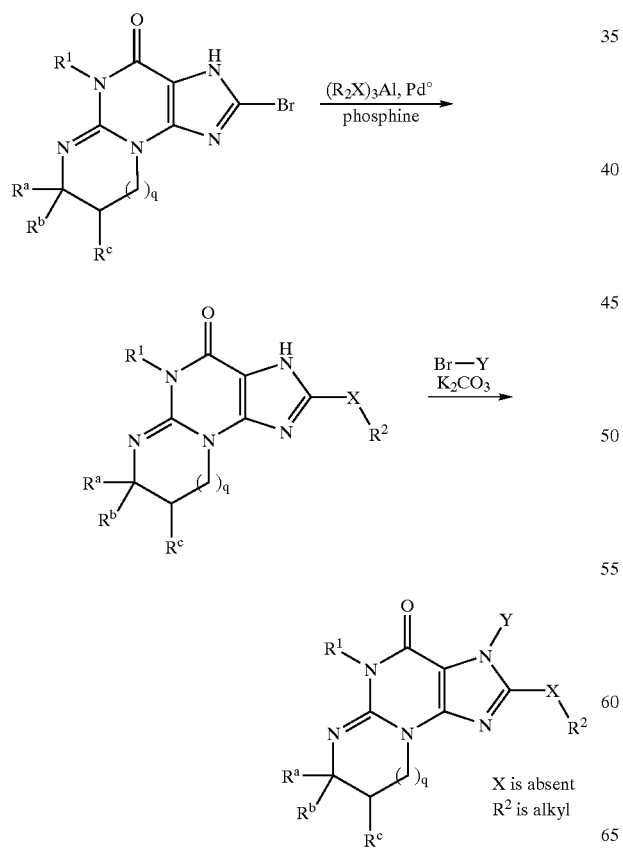
Scheme 5
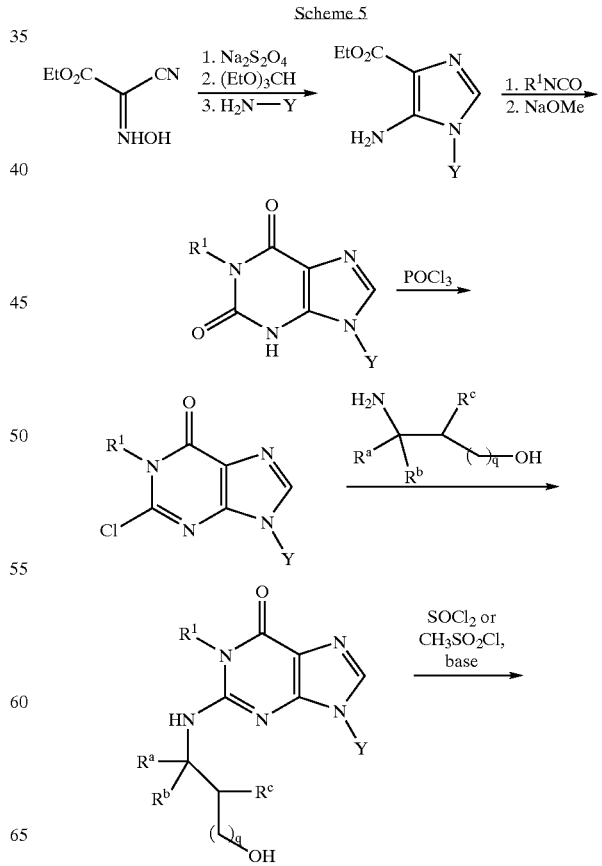

-continued

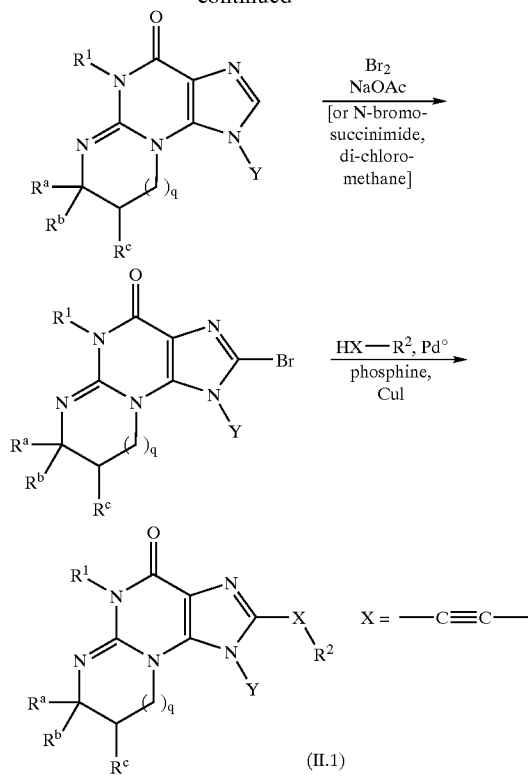

In the working examples, MeOH is methanol, EtOH is ethanol and Et$_2$O is diethyl ether.

PREPARATION OF EXAMPLES

Intermediate 1

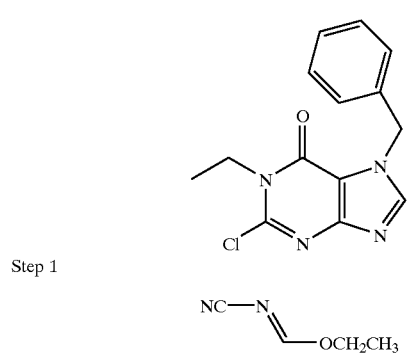

Step 1

A mixture of cyanamide (320 g, 7.62 mol) and triethyl orthoformate (2.2 L) was refluxed under N$_2$ for 3 h. The reaction mixture was allowed to cool, and ethanol was removed by distillation. Fractional distillation of the residue (0.5 mmHg, 50–60° C.) afforded the product (656 g, 88%). $^1$H NMR (300 MHz, CDCl$_3$) δ 8.40 (1H, s), 4.39 (2H, q, J=7 Hz), 1.39 (3H, t, J=7 Hz).

Step 2

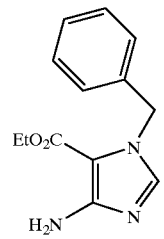

To a solution of the product of Step 1 (704 g, 7.2 mol) in Et$_2$O (600 ml) was added N-benzylglycine ethyl ester (1,300 g, 6.73 mol) over 0.5 h. The reaction mixture was stirred for 2 h, then concentrated. EtOH (500 ml) was added, and the mixture was evaporated to dryness. The residue was dissolved in EtOH (2.5 L), cooled in an ice bath, and 20% sodium ethoxide in EtOH (2.3 L) was added over 40 min. After the addition was complete the reaction mixture was stirred at RT for 1 h, then stored overnight in a refrigerator. The solid was collected, washed with cold EtOH, and dried at 55° C. in vacuo to give the product (1,219 g, 70%). $^1$H NMR (300 MHz, CDCl$_3$) δ 7.38–7.20 (4H, m), 7.17–7.12 (2H, m), 5.38 (2H, s), 4.8 (2H, b), 4.23 (2H, q, J=7 Hz), 1.23 (3H, t, J=7 Hz).

Step 3

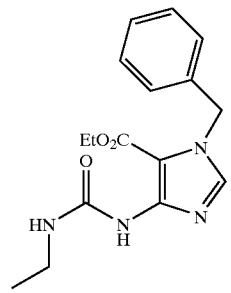

A mixture of the product of Step 2 (1,219 g, 4.97 mol), o-xylene (7.5 L), and ethyl isocyanate (425 g, 5.98 mol) was refluxed for 16 h. The reaction mixture was allowed to cool and the solvent was removed by distillation. The residue was triturated with Et$_2$O (1 L), and the solid was collected and dried in vacuo (50° C.) to give the product (1,310 g, 84%). $^1$H NMR (300 MHz, CDCl$_3$) δ 8.60 (1H, b), 7.90 (1H, b), 7.40–7.23 (4H, m), 7.16 (2H, m), 5.41 (2H, s), 4.23 (2H, q, J=7 Hz), 3.39 (2H, q, J=7 Hz), 1.30 (3H, t, J=7 Hz), 1.25 (3H, t, J=7 Hz).

Step 4

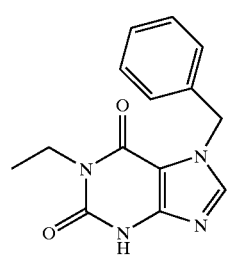

To a suspension of the product of Step 3 (1,310 g, 4.15 mol) in MeOH (5 L) was added sodium methoxide (500 g, 9.25 mol) in portions. The reaction mixture was refluxed for 4 h, then approximately 4 L of MeOH was distilled from the reaction mixture. The residue was poured into ice-water (5 L) and conc. HCl (1.8 L) was added. The white precipitate was collected, washed with water, and dried in vacuo (60° C.) to give the product (1,053 g, 94%). $^1$H NMR (DMSO-d6) δ 8.18 (1H, s), 7.38–7.25 (5H, m), 5.43 (2H, s), 3.81 (2H, q, J=7 Hz), 1.05 (3H, t, J=7 Hz).

Step 5

A suspension of the product of Step 4 (523 g, 1.93 mol) in $POCl_3$ (6 L) was refluxed under $N_2$ for 16 h, then approximately 4.5 L $POCl_3$ was distilled from the reaction mixture. The residue was poured onto ice and 50% NaOH was slowly added, along with the addition of ice to maintain the temperature at 0° C., until pH 6–7. The whole was extracted with $CH_2Cl_2$ (24 L) and the organic layer was dried ($MgSO_4$), filtered and concentrated. The residue was subjected to flash chromatography (EtOAc) to give the product 1 (351.1 g, 63%). $^1$H NMR (300 MHz, $CDCl_3$) δ 7.82 (1H, s), 7.40–7.30 (5H, m), 5.28 (2H, s), 4.37 (2H, q, J=7 Hz), 1.39 (3H, t, J=7 Hz).

Preparation 1

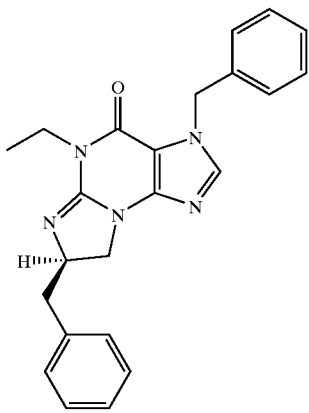

Step 1

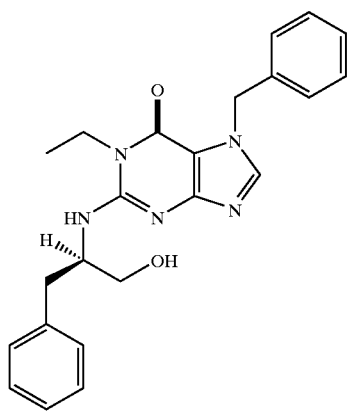

A mixture of the product of intermediate 1 (75 g, 0.26 mol), (R)-2-amino-3-phenyl-1-propanol (59 g, 0.39 mol), $iPr_2NEt$ (186 ml, 1.1 mol) and 1-methyl-2-pyrrolidinone (370 ml) was heated at 130° C. for 12 h. The reaction mixture was allowed to cool, then poured into 8 L of water and extracted with $CH_2Cl_2$ (2×8 L). The combined organic layers are concentrated, and the residue was subjected to vacuum distillation (18 mmHg) to remove 1-methyl-2-pyrrolidinone. The residue was triturated with ice-water to afford a semi-solid that was dissolved in MeOH, and the resultant solution was evaporated to dryness to give the product as a foam (94.5 g, 90%). $^1$H NMR (300 MHz, $CDCl_3$) δ 7.63 (1H, s), 7.40–7.20 (10H, m), 5.45 (2H, s), 4.65 (1H, m), 4.45 (1H, m), 3.96 (1H, m), 3.91 (1H, m), 3.80 (1H, m), 3.76 (1H, m), 3.09 (1H, m), 2.95 (1H, m), 1.02 (3H, t, J=7 Hz).

Step 2

To an ice-cold solution of the product of Step 1 (94.5 g, 0.24 mol) and $Et_3N$ (100 ml, 0.72 mol) in $CH_2Cl_2$ (1 L) was added methanesulfonyl chloride (41.2 g, 0.36 mol) dropwise over 0.5 h. After 0.5 h, the reaction mixture was refluxed for 2 h, then diluted with $CH_2Cl_2$ (2 L) and washed with sat'd $NaHCO_3$. The organic layer was dried ($MgSO_4$), filtered and evaporated. The residue was subjected to flash chromatography (EtOAc) to give the product (58 g, 63%). $^1$H NMR (300 MHz, $CDCl_3$) δ 7.40–7.20 (11H, m), 5.41 (2H, s), 4.50 (1H, m), 4.09 (2H, m), 3.95 (1H, m), 3.95 (1H, m), 3.81 (1H, m), 3.22 (1H, m), 2.72 (1H, m), 1.30 (3H, t, J=7 Hz).

Preparation 2

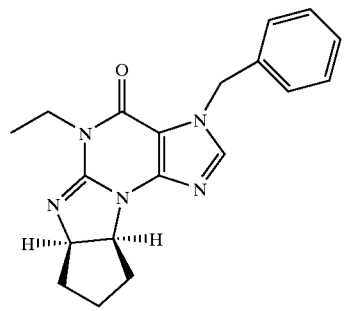

Reaction of intermediate 1 with (1R,2R)-2-aminocyclopentanol according to essentially the same procedure as outlined in Preparation 1, Step 1, and subjection of the product to methanesulfonyl chloride by essentially the same procedure described in Preparation 1, Step 2 afforded the product. HRMS Calcd for $C_{19}H_{21}N_5O$: 336.1824, Found: 336.1833.

Preparation 3

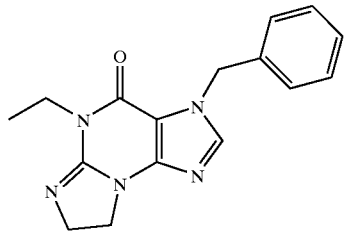

Step 1

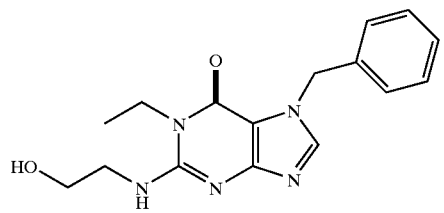

A mixture of the product of intermediate 1 (15 g, 52 mmol) and 2-aminoethanol (7.9 ml), in 1-methyl-2-pyrrolidinone (70 ml) was heated at 160° C. for 16 h. The reaction mixture was concentrated to low volume and the residue was taken up in $CH_2Cl_2$ (1 L) and washed with sat'd $NaHCO_3$. The aqueous layer was back-extracted with $CH_2Cl_2$ (×3), and the combined organic layers were dried (NaHCO$_3$), filtered and evaporated to give a solid (13.8 g, 85%). $^1$H NMR (400 MHz, CDCl$_3$) δ 7.63 (1H, s) 7.32 (5H, m), 5.49 (2H, s), 4.06 (2H, q, J=7.2 Hz), 3.88 (2H, m), 3.71 (2H, m), 1.31 (3H, t, J=7.2 Hz).

Step 2

To a solution of the product of Step 1 (12.4 g, 39.6 mmol) in CH$_2$Cl$_2$ (180 ml) was added thionyl chloride (3.5 ml, 47 mmol) dropwise under N$_2$. The reaction mixture was stirred overnight, diluted with CH$_2$Cl$_2$, and washed with 1 N NaOH. The organic layer was dried (NaHCO$_3$), filtered and concentrated to give the product (11.6 g, 99%). $^1$H NMR (400 MHz, CDCl$_3$) δ 7.41 (1H, s) 7.33 (5H, m), 5.43 (2H, s), 4.08 (2H, q, J=6.9 Hz), 4.02 (4H, m), 1.27 (3H, t, J=6.9 Hz).

Preparation 4

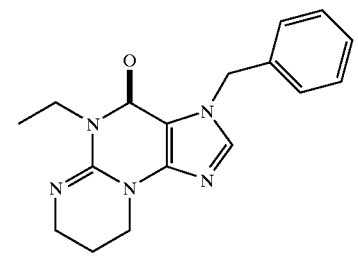

Step 1

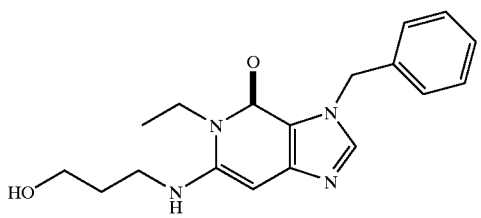

A mixture of intermediate 1 (10.0 g, 34.6 mmol), 3-amino-1-propanol (4.0 ml, 52 mmol) and diisopropylethylamine (15.4 mL, 86.6 mmol) in NMP (35 ml) was heated in a sealed tube at 120° C. overnight. The reaction mixture was cooled to RT and the solvent was removed by distillation to give a brown solid (12.2 g). MS (ES) m/e 328.1 (M+H)$^+$.

Step 2

The product of Step 1 (12.2 g) was dissolved in CH$_2$Cl$_2$ (115 ml) and SOCl$_2$ (7.6 mL, 104 mmol) was added dropwise. The reaction was stirred at room temperature under N$_2$ overnight and quenched with saturated NaHCO$_3$. The whole was extracted with CH$_2$Cl$_2$ (×3), and the combined organic layers were dried (Na$_2$SO$_4$), filtered and concentrated. The residue was dissolved in CH$_2$Cl$_2$ (100 ml). Triethylamine (2 ml) was added and the solution was heated to reflux for 3 h. After the reaction mixture was allowed to cool, sat'd NaHCO$_3$ was added and the whole was extracted with CH$_2$Cl$_2$ (×3). The combined aqueous layers were dried (Na$_2$SO$_4$), filtered and concentrated. Purification of the residue by flash chromatography (5:95 MeOH/CH$_2$Cl$_2$) gave the product (10.2 g, 95%) as a solid. $^1$H NMR (300 MHz, CDCl$_3$) δ 7.42 (1H, s) 7.33 (5H, m), 5.46 (2H, s), 4.09 (2H, q, J=6.9 Hz), 3.60 (2H, m), 3.40 (2H, m), 1.94 (2H, m), 1.21 (3H, t, J=6.9 Hz). MS (ES) m/e 310.1 (M+H)$^+$.

Preparation 5

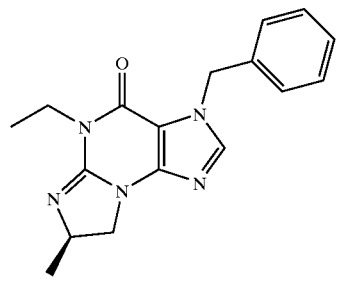

Reaction of intermediate 1 with (R)-2-amino-1-propanol according to essentially the same procedure as described in Preparation 1, Step 1, and reaction of the product with thionyl chloride by essentially the same sequence described in Preparation 4, Step 2 afforded the product. MS(ES) m/e 310.1 (M+H)$^+$ Preparation 6

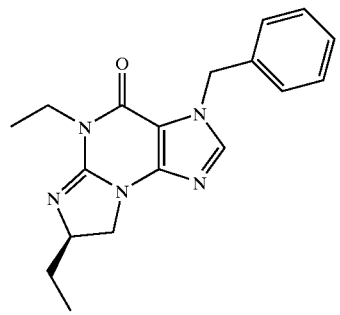

Reaction of intermediate 1 with (R)-2-amino-1-butanol according to essentially the same procedure as described in Preparation 1, Step 1, and reaction of the product with thionyl chloride by essentially the same sequence described in Preparation 4, Step 2 afforded the product. MS (ES) m/e 324.1 (M+H)$^+$.

Preparation 7

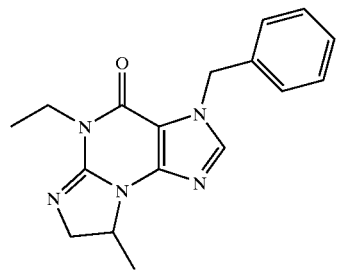

Reaction of intermediate 1 with 3-amino-2-propanol according to essentially the same procedure as described in Preparation 1, Step 1, and reaction of the product with thionyl chloride by essentially the same sequence described in Preparation 4, Step 2 afforded the product. $^1$H NMR (300 MHz, CDCl$_3$) δ 7.40 (1H, s), 7.32 (5H, m), 5.41 (2H, m), 4.56 (2H, m), 4.10 (1H, dd, J=13.2, 9.6 Hz) 3.99 (2H, m), 3.52 (1H, dd, J=13.2, 6.3 Hz), 1.50 (2H, d, J=6.3 Hz), 1.25 (3H, t, J=7.1 Hz). MS (ES) m/e 310.1 (M+H)$^+$

Preparation 8

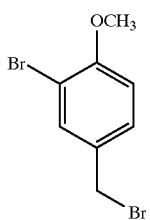

To a solution of 3-bromo-4-methoxytoluene (11 g, 54.7 mmol) in $CH_2Cl_2$ (100 ml) under $N_2$, was added N-bromosuccinimide (10.7 g, 60.2 mmol) and AIBN (82 mg, 0.5 mmol). The resulting mixture was refluxed overnight then cooled in an ice-water bath. The solid that precipitated was removed by filtration. The filtrate was washed with water (×2), brine (×1), dried ($Na_2SO_4$), filtered and concentrated. After drying under vacuum, the product (16.4 g, 100%) was obtained as a white solid that was used without further purification. $^1$H NMR (300 MHz, $CDCl_3$) δ 7.58 (1H, d, J=2.1 Hz), 7.29 (1H, dd, J=8.1, 2.1 Hz), 6.84 (1H, d, J=8.1 Hz), 4.43 (2H, s), 3.88 (3H, s).

Preparation 9

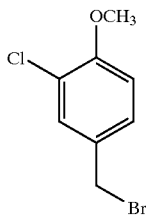

Reaction of 3-chloro-4-methoxytoluene, N-bromosuccinimide and AIBN by essentially the same procedure described for preparation 8 gave the product. $^1$H NMR (300 MHz, $CDCl_3$) δ 7.42 (1H, d, J=2.4 Hz), 7.26 (1H, dd, J=8.4, 2.4 Hz), 6.84 (1H, d, J=8.4 Hz), 4.44 (2H, s), 3.91 (2H, s).

Preparation 10

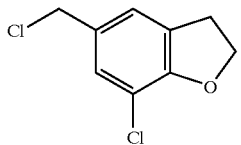

Step 1

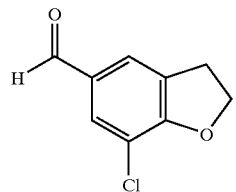

A mixture of 2,3-dihydrobenzofuran-5-carboxaldehyde (5.0 g, 33.8 mmol) and sulfuryl chloride (40 ml) was stirred at room temperature for 5 h. Excess sulfuryl chloride was removed and residue was partitioned between ethyl acetate (200 ml) and water (200 ml). The organic layer was washed with water, dried ($Na_2SO_4$), filtered and concentrated. The residue was subjected to column chromatography to give the product (3.5 g, 57%). $^1$H NMR (300 MHz, $CDCl_3$) δ 9.80 (1H, s), 7.69 (1H, s), 7.65 (1H, s), 4.81 (2H, m), 3.37 (2H, m).

Step 2

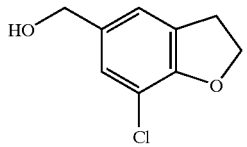

The product of Step 1 (3.5 g, 19.3 mmol) was dissolved in THF (50 ml) and sodium borohydride (1.5 g, 40 mmol) was added. The reaction mixture was refluxed for one hour. Ethyl acetate (100 ml) was added and organic layer was washed with water (3×100 ml), dried ($Na_2SO_4$), and filtered. After evaporation of solvent, the residual product (2.9 g, 83%) was used in the next step without further purification. $^1$H NMR (300 MHz, $CDCl_3$) δ 7.13 (1H, s), 7.11 (1H, s), 4.69 (2H, m), 4.58 (2H, s), 3.30 (2H, m).

Step 3

The product of Step 2 (2.9 g, 16 mmol) was dissolved in $CH_2Cl_2$ (50 ml) and thionyl chloride (2 ml) was added. The reaction mixture was stirred at room temperature for one hour. Saturated $NaHCO_3$ solution (50 ml) was added and the whole was extracted with $CH_2Cl_2$. The organic layer was dried ($Na_2SO_4$), filtered and concentrated. Subjection of the residue to column chromatography (hexane) gave the product (2.4 g, 74%). $^1$H NMR (300 MHz, $CDCl_3$) δ 7.16 (1H, s), 7.13 (1H, s), 4.70 (2H, m), 4.51 (2H, s), 3.30 (2H, m).

Preparation 11

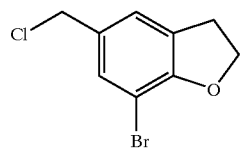

Step 1

To a stirred suspension of 2,3-dihydrobenzo[b]furan-5-carboxylic acid (3.0 g, 18 mmol) in ACOH (40 ml) was added $Br_2$ (5 g, 31 mmol). After 16 h, the whole was evaporated to dryness and the residue was triturated with ether. The solid was collected and dried to afford the product (3.7 g, 84%). $^1$H NMR (300 MHz, $CDCl_3$) δ 7.94 (1H, s), 7.72 (1H, s), 4.66 (2H, m), 3.27 (2H, m).

Step 2

To a suspension of the product of step 1 (3.7 g, 15 mmol) in THF (100 ml) was added lithium aluminum hydride (0.56 g, 15 mmol), and the mixture was refluxed for 3 h. The reaction mixture was allowed to cool, then water was added. The whole was extracted with EtOAc and the organic layer was dried ($Na_2SO_4$), filtered and evaporated. The residue (2.7 g) was dissolved in $CH_2Cl_2$ (25 ml), and $SOCl_2$ (2.4 g, 20 mmol) was added. The reaction mixture was stirred for 2 h, then diluted with $CH_2Cl_2$ (25 ml), and the whole was washed with water (3×50 ml). The organic layer was dried ($Na_2SO_4$), filtered and concentrated. The residue was subjected to flash chromatography (5:95 EtOAc/hexanes), followed by vacuum distillation (150° C., 0.5 mmHg) to give the product (1.6 g, 43%). $^1$H NMR (300 MHz, $CDCl_3$) δ 7.30 (1H, s), 7.16 (1H, s), 4.68 (2H, m), 4.50 (2H, s), 3.31 (2H, m).

Preparation 12

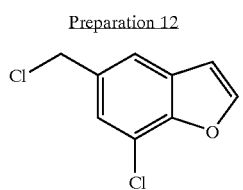

Preparation 10 (1.2 g, 5.9 mmol) was dissolved in toluene (50 ml) and DDQ (3 g) was added. The reaction mixture was stirred at RT overnight. Additional DDQ (3 g) was added and the reaction mixture was refluxed for five hours. The solvent was removed and to the residue was added ether (100 ml). The precipitate was filtered, the filtrate was concentrated, and the residue was subjected to column chromatography (hexane) to give the product. $^1$H NMR (300 MHz, CDCl$_3$) δ 7.71 (1H, m), 7.53 (1H, s), 7.37 (1H, s), 7.81 (1H, m), 4.67 (2H, s).

Preparation 13

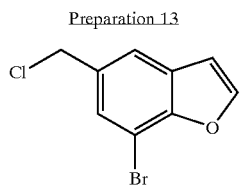

Reaction of preparation 11 with DDQ by essentially the procedure described for preparation 12 afforded the product. $^1$H NMR (300 MHz, CDCl$_3$) δ 7.72 (1H, m), 7.58 (1H, s), 7.53 (1H, s), 6.84 (1H, m), 4.67 (2H, s).

Preparation 14

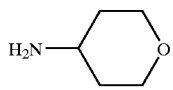

To a stirred mixture of tetrahydro-4H-pyran-4-one (22.5 g, 225 mmol) and benzylamine (32.7 ml, 300 mmol) in 1,2-dichloroethane (400 ml), was added Na(Oac)$_3$BH (107 g, 500 mmol). The reaction mixture was stirred for 2 days, diluted with CH$_2$Cl$_2$ and washed with 1 N NaOH. The organic layer was dried (NaHCO$_3$), filtered and evaporated. Chromatography of the residue over silica (gradient 1:99 MeOH/CH$_2$Cl$_2$, then 2:98 MeOH/CH$_2$Cl$_2$, then 5:95 MeOH/CH$_2$Cl$_2$) gave 4-benzylaminotetrahydro-2H-pyran. This product was dissolved in MeOH (350 ml), and to the solution was added ammonium formate (46 g, 730 mmol) and 10% Pd(OH)$_2$-on-carbon (23 g). The reaction mixture was refluxed for 3 hours, then filtered and concentrated to give the product (19 g) that was used without further purification. $^1$H NMR (300 MHz, CDCl$_3$) δ 3.96 (2H, m), 3.38 (2H, m), 2.88 (1H, m), 2.00 (2H, b), 1.78 (2H, m), 1.44 (2H, m).

The numbers for the following examples do not correspond to the numbers recited for the compounds listed in Tables I, II and III above.

Example 1

Step 1

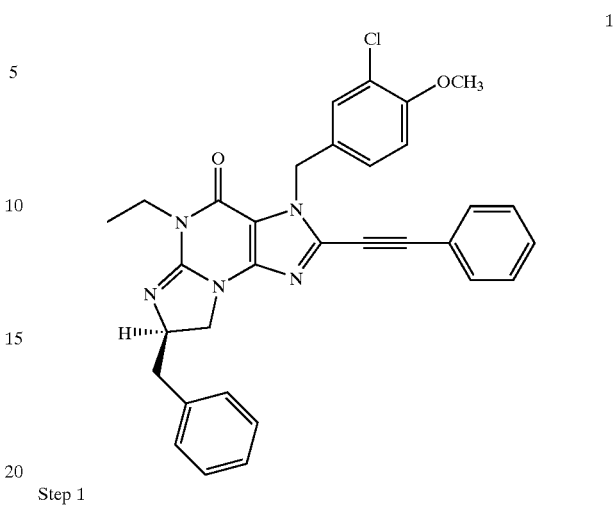

A mixture of Preparation 1 (58 g, 0.15 mol), ammonium formate (350 g, 5.5 mol) and 20% Pd(OH)$_2$/C (25 g) in MeOH (1.3 L) was refluxed for 3 h. The reaction mixture was allowed to cool, additional ammonium formate (100 g, 1.6 mol) and 20% Pd(OH)$_2$/C (25 g) was added, and the mixture was refluxed for 2 h. The reaction mixture was filtered and the filtrate was concentrated. The residue was dissolved in CH$_2$Cl$_2$ (3 L), washed with sat'd NaHCO$_3$, dried (MgSO$_4$), filtered and evaporated to give the product (37 g, 84%). $^1$H NMR (300 MHz, CDCl$_3$) δ 7.62 (1H, s), 7.35–7.18 (5H, m), 4.55 (1H, m), 4.19–3.95 (3H, m), 3.90 (1H, m), 3.21 (1H, m), 2.78 (1H, m), 1.35 (3H, t, J=7 Hz).

Step 2

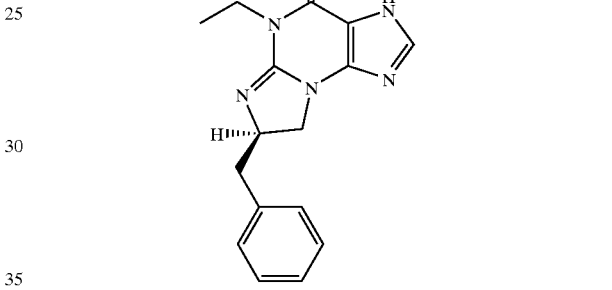

To a solution of the product of Step 1 (17 g, 58 mmol) in AcOH (700 ml) was added sodium acetate (10 g, 0.12 mol) and Br$_2$ (12.5 g, 78 mmol), and the reaction mixture was stirred at 50° C. for 12 h. After the reaction mixture had cooled to RT, sodium bisulfite (40 g) was added and the whole was concentrated. The residue was taken up in CH$_2$Cl$_2$, washed with sat'd NaHCO$_3$, dried (MgSO$_4$), filtered and evaporated to give the product (17 g, 80%). $^1$H NMR (300 MHz, CDCl$_3$) δ 7.32–7.15 (5H, m), 4.88 (1H, m), 4.37 (1H, m), 4.17 (3H, m), 3.26 (1H, m), 3.02 (1H, m), 1.25 (3H, t, J=7 Hz).

Step 3

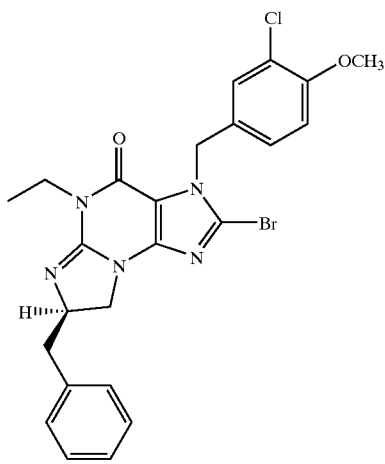

1.3.1

To a suspension of the product of Step 2 (500 mg, 1.34 mmol) and K$_2$CO$_3$ (0.55 g, 4.0 mmol) in DMF (6 ml) was added 3-chloro-4-methoxybenzyl bromide (Preparation 9; 0.94 g, 4.0 mmol) and the reaction mixture was stirred overnight. Water (30 ml) was added and the whole was extracted with EtOAc (3×20 ml). The combined organic layers were washed with water, dried (MgSO$_4$), filtered and evaporated. The residue was subjected to PTLC (3:97 MeOH/CH$_2$Cl$_2$) to give the product (0.38 g, 54%). $^1$H NMR (300 MHz, CDCl$_3$) δ 7.40–7.19 (7H, m), 6.86 (1H, d, J=11.6 Hz), 5.37 (2H, s), 4.44 (1H, m), 4.00 (2H, m), 3.88–3.75 (2H, m), 3.86 (3H, s), 3.18 (1H, dd, J=18.0, 6.0 Hz), 2.69 (1H, dd, J=18.0, 12.4 Hz), 1.29 (3H, t, J=9.2 Hz). Similarly prepared was the following compound:

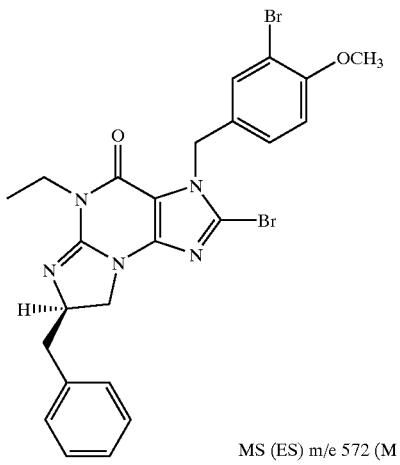

1.3.2

MS (ES) m/e 572 (M + H)$^+$.

Step 4
To a solution of the product of Step 3 (1.3.1) (180 mg, 0.35 mmol) in DMF (3.5 ml) was successively added (PPh$_3$)$_2$PdCl$_2$ (98 mg, 0.14 mmol), CuI (14 mg, 0.07 mmol) and triethylamine (0.1 ml, 0.7 mmol). The reaction mixture was stirred at room temperature for 15 minutes, and then phenylacetylene (142 mg, 1.4 mmol) was added. The reaction mixture was stirred at room temperature for 16 h, poured into a large volume of CH$_2$Cl$_2$ and NH$_4$OH, and the organic layer was washed water, dried (Na$_2$SO$_4$), filtered and concentrated. Subjection of the residue to PTLC (95:5 CH$_2$Cl$_2$/MeOH) afforded the product (130 mg, 68%). $^1$H NMR (300 MHz, CDCl$_3$) δ 7.75–7.16 (12H, m), 6.92–6.84, (1H, d), 5.51 (2H, s), 4.57–4.43 1H, m), 4.20–3.80 (4H, m), 3.87 (3H, s), 3.28–3.17 (1H, m), 2.80–2.67 (1H, m), 1.37–1.28 (3H, m). MS (ES) m/e 550 (M+H)$^+$.

Example 2

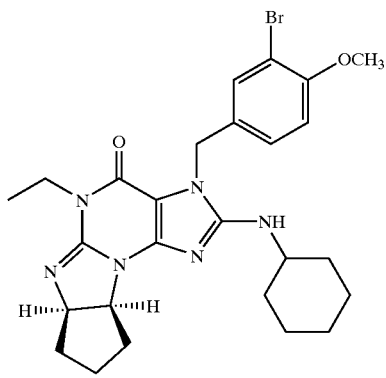

2

Step 1

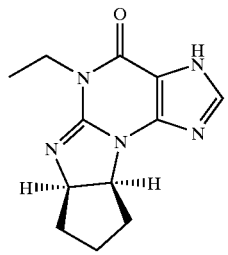

2.1.1

Reaction of Preparation 2 with Pd(OH)$_2$/C and ammonium formate in MeOH by essentially the procedure described in Example 1, Step 1 gave the product. $^1$H NMR (300 MHz, CDCl$_3$) δ 7.81 (s, 1H), 6.1 (br, 1H), 5.03 (1H, t, J=7.2 Hz), 4.86 (1H, t, J=7.2 Hz), 4.05 (2H, m), 2.35 (1H, m), 2.15 (1H, m), 2.00–1.80 (3H, m), 1.62 (1H, m), 1.24 (3H, t, J=7.2 Hz). MS (ES) m/e 246 (M+H)$^+$.

Step 2

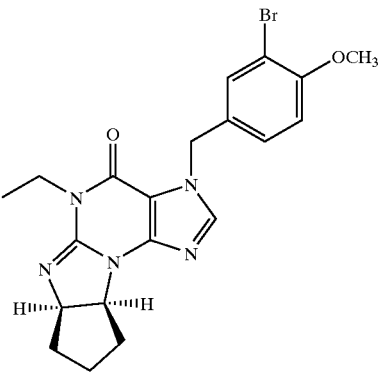

2.2.1

A mixture of the product of Step 1 (2.1.1) (2.10 g, 8.5 mmol), 3-bromo-4-methoxybenzylbromide (Preparation 8; 3.60 g, 12.9 mmol), and K$_2$CO$_3$ (3.55 g, 25.7 mmol) was stirred overnight, diluted with dichloromethane, washed with water, dried (Na$_2$SO$_4$), filtered, and concentrated. The residue was purified by flash chromatography (gradient 99:1-97:3 CH$_2$Cl$_2$/MeOH) to give the product (3.02 g, 79%). MS (ES) m/e 444 (M+H)$^+$.

Reaction of the product of Step 1 (2.1.1) with 3-chloro-4-methoxybenzylbromide (Preparation 9) by essentially the same procedure afforded the following product.

2.2.2

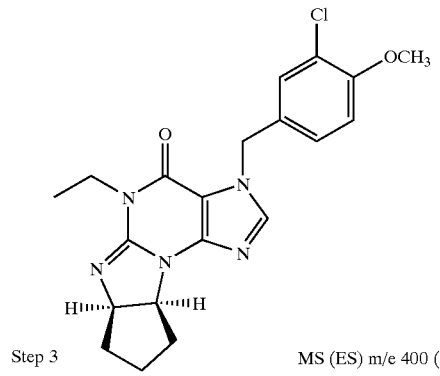

Step 3                    MS (ES) m/e 400 (M + H)$^+$.

2.3.1

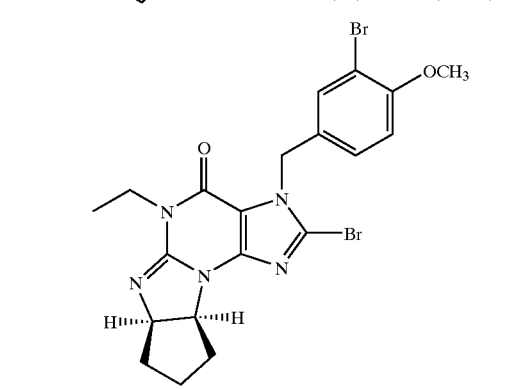

To a solution of the product of Step 2 (2.2.1) (300 mg, 0.675 mmol) in THF at −78° C. was added dropwise of 2M solution of LDA in THF (0.51 ml). The mixture was stirred in the cold for 25 min followed by the addition of 1,2-dibromotetrafluoroethane (349 mg, 1.35 mmol). The mixture was stirred for 1 h at −78° C., quenched with sat'd NaHCO$_3$, extracted with CH$_2$Cl$_2$, dried (Na$_2$SO$_4$), filtered and concentrated. Subjection of the residue to PTLC gave the product (266 mg, 75%). MS (ES) m/e 522 (M+H)$^+$.

Use of the appropriate starting material and essentially the same procedure afforded the following product.

2.3.2

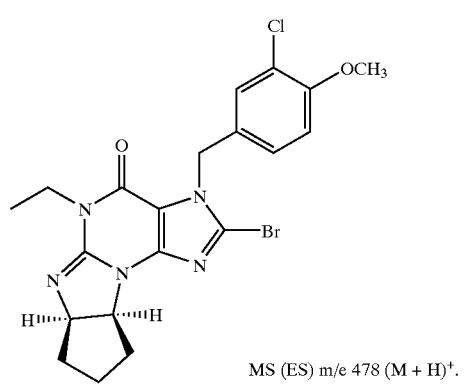

MS (ES) m/e 478 (M + H)$^+$.

Step 4

A mixture of the product of Step 3 (2.3.1) (60 mg) and cyclohexylamine (4 ml) was heated in a sealed tube at 110° C. for 12 h. The reaction mixture was diluted with CH$_2$Cl$_2$, washed with sat'd NaHCO$_3$, dried (Na$_2$SO$_4$), filtered, and the volatiles were evaporated. The residue was purified by PTLC (1:9 MeOH/CH$_2$Cl$_2$) to afford the product (41 mg). $^1$H NMR (300 MHz, CDCl$_3$) δ 7.46 (1H, d, J=2.2 Hz), 7.2 (1H, dd, J=2.2, 8.5 Hz), 6.87 (1H, d, J=8.5 Hz), 5.19 (2H, AB), 4.77 (1H, t, J=7.3 Hz), 4.67 (1H, t, J=7.3 Hz), 3.97 (2H, m), 3.89 (3H, s), 3.73 (1H, m), 2.24 (1H, dd, J=5.5, 12.6 Hz), 2.0–1.0 (15H, m), 1.25 (3H, t, J=7 Hz). MS (ES) m/e 541 (M+H)$^+$.

Use of 2.3.2 as starting material and essentially the same procedure afforded the following product.

2A

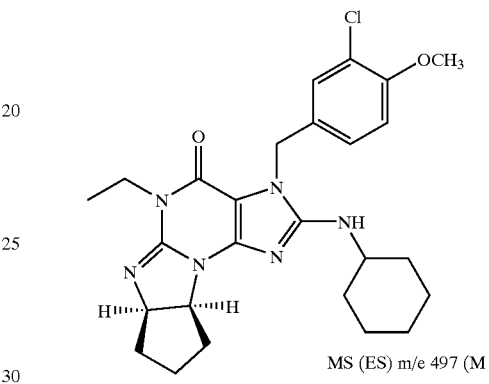

MS (ES) m/e 497 (M + H)$^+$.

Example 3

3

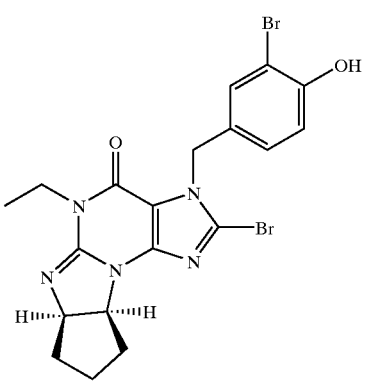

To a mixture of the product of Example 2, Step 3 (2.3.1) (20 mg, 0.038 mmol) and CH$_2$Cl$_2$ (1 ml) was added 1M solution of BBr$_3$ in CH$_2$Cl$_2$ (0.2 ml, 0.19 mmol). The mixture was stirred for 30 min, quenched with aq. NH$_3$, extracted with CH$_2$Cl$_2$, dried (Na$_2$SO$_4$), filtered and evaporated to afford the product (15 mg, 76%). $^1$H NMR (300 MHz, CDCl$_3$) δ 7.58 (1H, d, J=1.7 Hz), 7.31 (1H, dd, J=1.7, 8.2 Hz), 6.97 (1H, d, J=8.2 Hz), 5.34 (2H, s), 4.79 (1H, t, J=7.0 Hz), 4.71 (1H, t, J=7.0 Hz), 4.0 (2H, q, J=7.0 Hz), 2.21 (1H, dd, J=6.0, 13 Hz), 1.95 (1H, m), 1.78 (3H, m), 1.54 (1H, m), 1.25, (3H, t, J=7.0 Hz). MS (ES) m/e 508 (M+H)$^+$.

Example 4

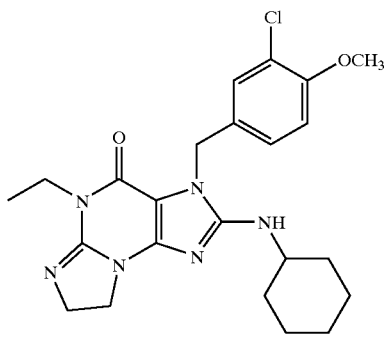

Step 1

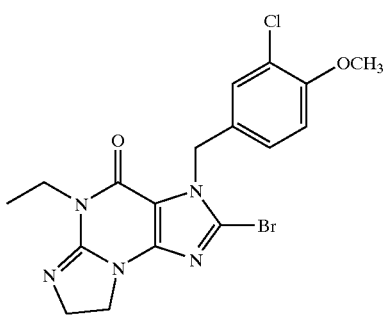

Subjection of Preparation 3 to essentially the same sequence of reactions described in Example 1, Steps 1–3 gave the product. $^1$H NMR (400 MHz, CDCl$_3$) δ 7.41 (1H, d, J=2.4 Hz), 7.30 (1H, dd, J=8.4, 2.0 Hz), 6.89 (1H, d, J=8.4 Hz), 5.40 (2H, s), 4.07–4.00 (6H, m), 3.88 (3H, s), 1.27 (3H, t, J=6.8 Hz).

Step 2

Reaction of the product of Step 1 (4.1.1) with cyclohexylamine by essentially the procedure of Example 2, Step 4 gave the product. $^1$H NMR (CDCl$_3$, 400 MHz) δ 7.24 (1H, s), 7.12 (1H, d, J=8 Hz), 6.89 (1H, d, J=8 Hz), 5.18 (2H, s), 4.04–3.87 (7H, m), 3.87 (3H, s), 3.71 (1H, m), 1.92 (2H, m), 1.57 (2H, m), 1.37 (2H, m), 1.25 (3H, m), 1.10 (4H, m). HRMS: Calcd for C$_{23}$H$_{30}$ClN$_6$O$_2$: 457.2119, Found: 457.2121.

Reaction of the product of Step 1 with the appropriate amine using essentially the same procedure afforded the following examples:

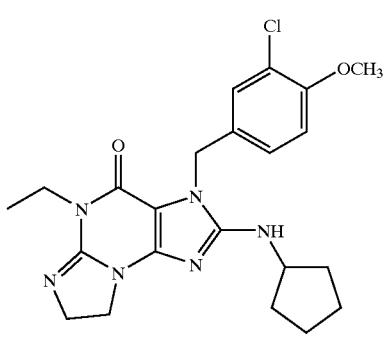

$^1$H NMR (CDCl$_3$, 400 MHz) δ 7.23 (1H, s), 7.12 (1H, d, J=8 Hz), 6.89 (1H, d, J=8 Hz), 5.18 (2H, s), 4.13 (1H, m), 4.05–3.90 (7H, m), 3.87 (3H, s), 1.95 (2H, m), 1.55 (4H, m), 1.31 (2H, m), 1.25 (3H, m). HRMS: Calcd for C$_{22}$H$_{28}$ClN$_6$O$_2$: 443.1962, Found: 443.1957.

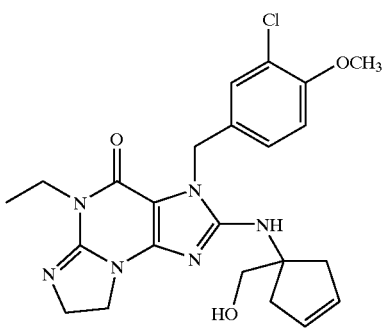

$^1$H NMR (CDCl$_3$, 400 MHz) δ 7.23 (s, 1H), 7.13 (1H, d, J=8 Hz), 6.89 (1H, d, J=8 Hz), 5.60 (2H, s), 5.19 (2H, s), 3.99 (7H, m), 3.75 (3H, s), 2.67 (2H, d, J=15 Hz), 2.30 (2H, d, J=15 Hz), 1.26 (3H, m). HRMS: Calcd: for C$_{23}$H$_{28}$ClN$_6$O$_3$: 471.1911, Found: 471.1905.

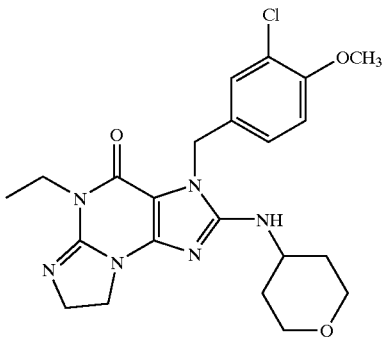

$^1$H NMR (CDCl$_3$, 400 MHz) δ 7.22 (1H, s), 7.10 (1H, d, J=8 Hz), 6.88 (1H, d, J=8 Hz), 5.19 (2H, s), 4.03–3.95 (10H, m), 3.87 (3H, s), 3.49 (2H, m), 1.95 (2H, m), 1.35 (2H, m), 1.24 (3H, m). HRMS: Calcd for C$_{22}$H$_{28}$ClN$_6$O$_3$: 459.1911, Found: 459.1903.

Example 5

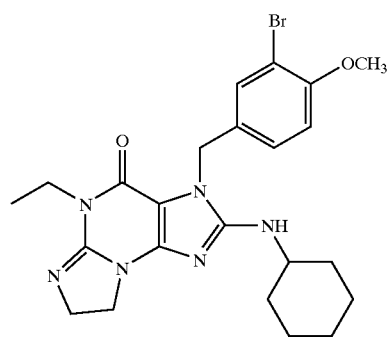

Step 1

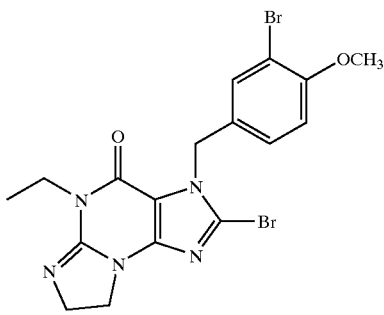
5.1.1

Subjection of Preparation 3 to essentially the same sequence of reactions described in Example 1, Steps 1–3, except that 3-bromo-4-methoxybenzyl bromide (Preparation 8) was used as alkylating agent in Step 3, gave the product. $^1$H NMR (400 MHz, CDCl$_3$) δ 7.59 (1H, d, J=2.0 Hz), 7.36 (1H, dd, J=8.4, 2.0 Hz), 6.85 (1H, d, J=8.4 Hz), 5.41 (2H, s), 4.08–4.01 (6H, m), 3.88 (3H, s), 1.28 (3H, t, J=6.8 Hz).

Step 2

Reaction of the product of Step 1 (5.1.1) with cyclohexylamine by essentially the procedure of Example 2, Step 4 gave the product. $^1$H NMR (400 MHz, CDCl$_3$) δ 7.42 (1H, s), 7.18 (1H, d, J=8 Hz), 6.87 (1H, d, J=8 Hz), 5.21 (2H, s), 4.13–3.97 (7H, m), 3.88 (3H, s), 3.73 (1H, m), 1.89 (2H, m), 1.58 (2H, m), 1.35 (2H, m), 1.28 (3H, s), 1.11 (4H, m). HRMS: Calcd for C$_{23}$H$_{30}$BrN$_6$O$_2$: 501.1614, Found: 501.1620.

Reaction of the product of Step 1 (5.1.1) with an appropriate amine using essentially the same procedure afforded the following examples:

5A

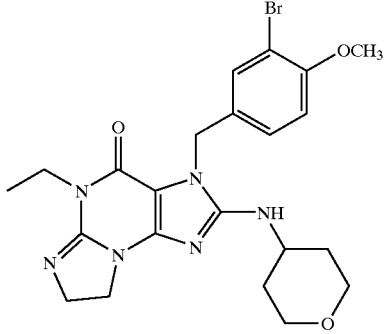

$^1$H NMR (400 MHz, CDCl$_3$) δ 7.39 (1H, s), 7.15 (1H, d, J=8 Hz), 6.85 (1H, d, J=8 Hz), 5.19 (2H, s), 4.05–3.89 (10H, m), 3.86 (3H, s), 3.46 (2H, m), 1.92 (2H, m), 1.36 (2H, m), 1.24 (3H, m). HRMS: Calcd for C$_{22}$H$_{28}$BrN$_6$O$_3$: 503.1406, Found: 503.1400.

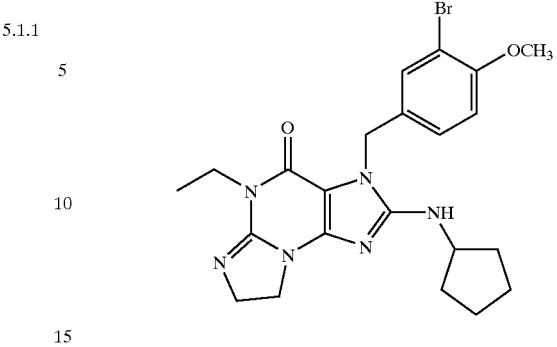
5B $^1$H NMR (400 MHz, CDCl$_3$) δ 7.40 (1H, s), 7.15 (1H, d, J=8 Hz), 6.85 (1H, d, J=8 Hz), 5.17 (s, 2H), 4.16 (1H, m), 4.04–3.95 (7H, m), 3.86 (3H, s), 1.95 (2H, m), 1.55 (4H, m), 1.31 (2H, m), 1.24 (3H, m). HRMS: Calcd for C$_{22}$H$_{28}$BrN$_6$O$_2$: 487.1457, Found: 487.1461.

Example 6

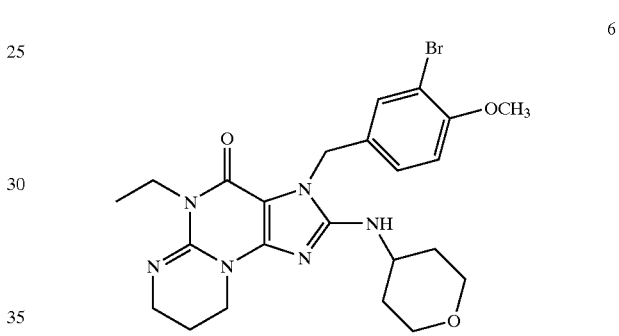
6

Step 1

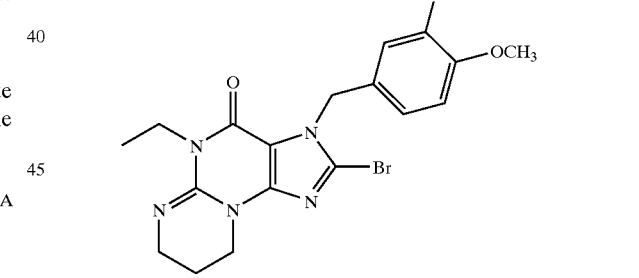
6.1.1

Subjection of Preparation 4 to essentially the same sequence of reactions described in Example 1, Steps 1–3, except that 3-bromo-4-methoxybenzyl bromide (Preparation 8) was used as alkylating agent in Step 3, gave the product. $^1$H NMR (300 MHz, CDCl$_3$) δ 7.57 (1H, s), 7.33 (1H, d, J=8.4 Hz), 6.81 (1H, d, J=8.4 Hz), 5.38 (2H, s), 4.03 (2H, q, J=6.9 Hz), 3.91 (2H, m), 3.83 (3H, s), 3.54 (2H, m), 1.88 (2H, m), 1.17 (3H, t, J=6.9 Hz). MS (ES) m/e 498.1 (M+H)$^+$.

Step 2

A solution of the product of Step 1 (6.1.1) (66 mg, 0.13 mmol), 4-aminotetrahydropyran (67 mg, 0.66 mmol) (Preparation 13) and diisopropylethylamine (0.070 ml, 0.30 mmol) in NMP (0.3 ml) was heated at 130° C. in a sealed tube for 18 h. After the reaction mixture had cooled to room temperature, cold water (5 ml) was added and a brown solid precipitated. The resultant solid was collected, and dried and subjected to PTLC (10:90 MeOH/CH$_2$Cl$_2$) to give the product (28.2 mg, 41%) as a white solid. $^1$H NMR (300 MHz, CDCl$_3$) δ 7.44 (1H, d, J=2.1 Hz) 7.23 (1H, dd, J=8.4, 2.1 Hz), 6.85 (1H, d, J=8.4 Hz), 5.30 (2H, s), 4.16 (2H, q, J=6.9 Hz), 4.05 (2H, m), 3.91 (3H, m), 3.86 (3H, s), 3.66 (2H, m), 3.48 (2H, m), 1.99 (4H, m), 1.48 (2H, m), 1.24 (3H, t, J=6.9 Hz). MS (ES) m/e 519.1 (M+H)$^+$.

Reaction of the product of Step 1 (6.1.1) with an appropriate amine using essentially the same procedure afforded the following examples:

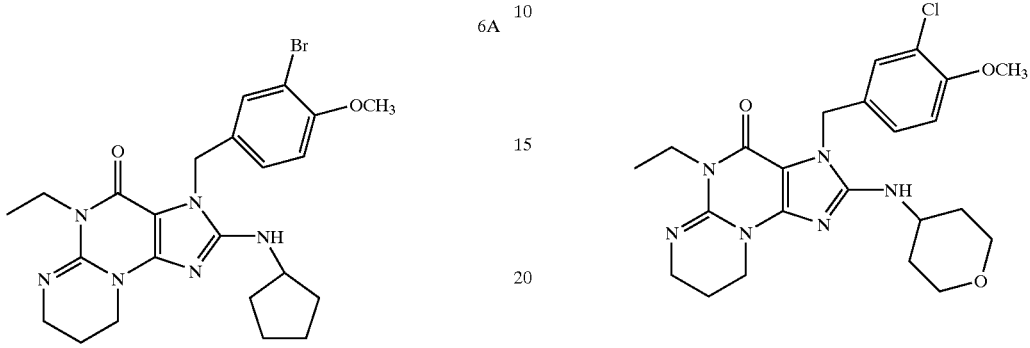

6A $^1$H NMR (300 MHz, CDCl$_3$) δ 7.43 (1H, d, J=2.1 Hz), 7.18 (1H, dd, J=8.4, 2.1 Hz), 6.84 (1H, d, J=8.4 Hz), 5.22 (2H, s), 4.16 (2H, m), 4.08 (2H, q, J=6.9 Hz), 3.99 (2H, m), 3.87 (3H, s), 3.60 (2H, m), 1.94 (4H, m), 1.47 (4H, m), 1.34 (2H, m), 1.20 (3H, t, J=6.9 Hz). MS (ES) m/e 503.1 (M+H)$^+$.

6B

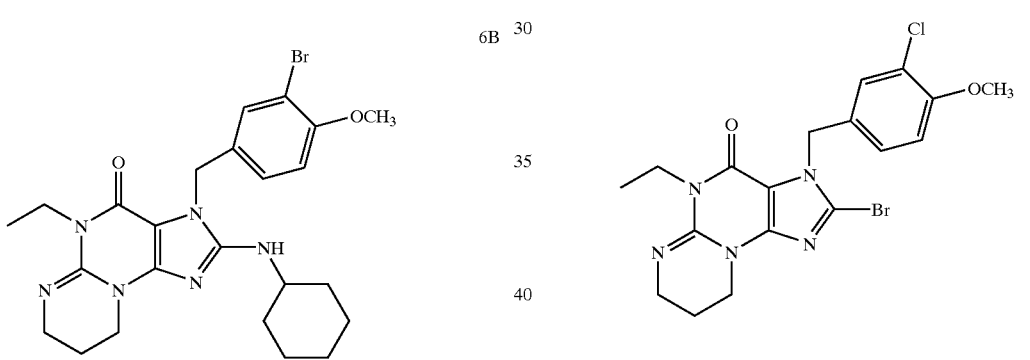

$^1$H NMR (300 MHz, CDCl$_3$) δ 7.43 (1H, d, J=2.1 Hz), 7.18 (1H, dd, J=8.4, 2.1 Hz), 6.84 (1H, d, J=8.4 Hz), 5.23 (2H, s), 4.08 (2H, q, J=6.9 Hz), 3.99 (2H, m), 3.87 (3H, s), 3.70 (1H, m), 3.61 (2H, m), 1.94 (4H, m), 1.59 (3H, m), 1.35 (2H, m), 1.21 (3H, t, J=6.9 Hz), 1.14 (3H, m). MS (ES) m/e 517.1 (M+H)$^+$.

6C

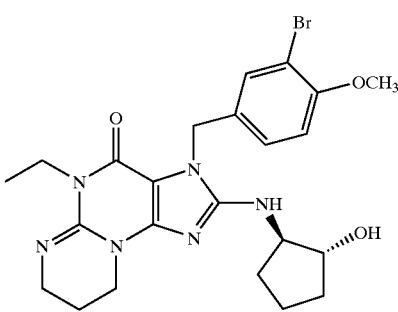

$^1$H NMR (300 MHz, CDCl$_3$) δ 7.46 (1H, d, J=2.1 Hz), 7.21 (1H, dd, J=8.4, 2.1 Hz), 6.83 (1H, d, J=8.4 Hz), 5.27 (m, 2H), 4.08 (2H, q, J=6.9 Hz), 3.95 (2H, m), 3.86 (3H, s), 3.73 (1H, m), 3.59 (2H, m), 2.10 (2H, m), 1.94 (2H, m), 1.68 (3H, m), 1.45 (1H, m), 1.20 (3H, t, J=6.9 Hz). MS (ES) m/e 519.1 (M+H)$^+$.

Example 7

7

[Structure 7]

Step 1

7.1.1

[Structure 7.1.1]

Subjection of Preparation 4 to essentially the same sequence of reactions described in Example 1, Steps 1–3 gave the product. $^1$H NMR (300 MHz, CDCl$_3$) δ 7.41 (1H, d, J=2.1 Hz), 7.31 (1H, dd, J=8.4, 2.1 Hz), 6.87 (1H, d, J=8.4 Hz), 5.41 (2H, s), 4.08 (2H, q, J=6.9 Hz), 3.96 (2H, m), 3.87 (3H, s), 3.58 (2H, m), 1.93 (2H, m), 1.21 (3H, t, J=6.9 Hz). MS (ES) m/e 454.1 (M+H)$^+$.

Step 2

Reaction of the product of Step 1 (7.1.1) with 4-aminotetrahydropyran by the procedure of Example 6, Step 2 gave the product. $^1$H NMR (300 MHz, CDCl$_3$) δ 7.26 (1H, d, J=2.1 Hz), 7.16 (1H, dd, J=8.4, 2.1 Hz), 6.87 (1H, d, J=8.4 Hz), 5.28 (2H, s), 4.5 (1H, br), 4.11 (2H, q, J=6.9 Hz), 4.02 (2H, m), 3.93 (3H, m), 3.88 (3H, s), 3.63 (2H, m), 3.47 (2H, m), 1.98 (4H, m), 1.47 (2H, m), 1.22 (3H, t, J=6.9 Hz). MS (ES) m/e 517.1 (M+H)$^+$.

Reaction of the product of Step 1 with an appropriate amine using essentially the same procedure afforded the following examples:

7A

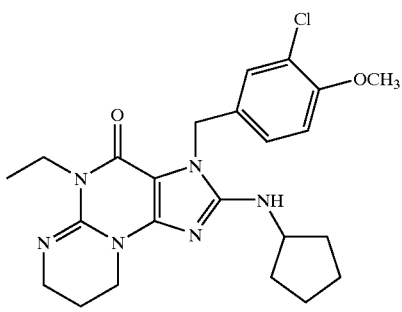

¹H NMR (300 MHz, CDCl₃) 7.26 (1H, d, J=2.1 Hz), 7.18 (1H, dd, J=8.4, 2.1 Hz), 6.87 (1H, d, J=8.4 Hz), 5.32 (2H, s), 4.98 (1H, br), 4.21 (3H, m), 4.11 (2H, m), 3.87 (3H, s), 3.71 (2H, m), 2.08 (2H, m), 1.98 (2H, m), 1.61 (4H, m), 1.48 (2H, m), 1.25 (3H, t, J=6.9 Hz). MS (ES) m/e 457.1 (M+H)⁺.

7B

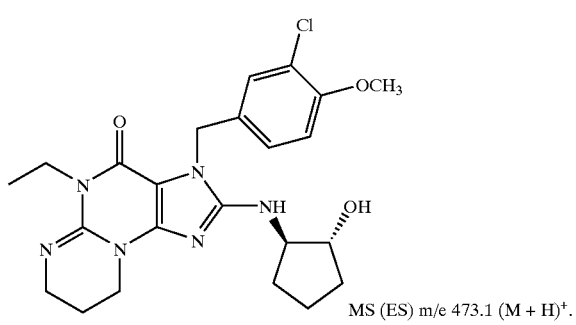

MS (ES) m/e 471.1 (M + H)⁺.

7C

MS (ES) m/e 473.1 (M + H)⁺.

Example 8

8

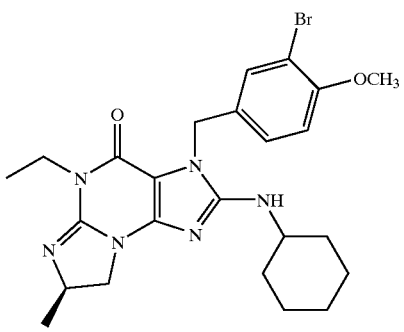

Step 1

8.1.1

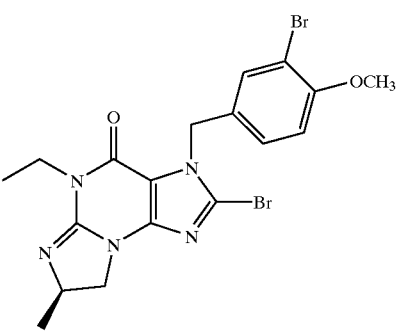

Subjection of Preparation 5 to essentially the same sequence of reactions described in Example 1, Steps 1–3, except that 3-bromo-4-methoxybenzyl bromide (Preparation 8) was used as alkylating agent in Step 3, gave the product. ¹H NMR (300 MHz, CDCl₃) δ 7.55 (1H, d, J=2.1 Hz), 7.31 (1H, dd, J=8.4, 2.1 Hz), 6.81 (1H, d, J=8.4 Hz), 5.36 (2H, m), 4.26 (1H, m), 4.11 (1H, t, J=9.5 Hz), 3.99 (1H, m), 3.83 (3H, s), 3.55 (1H, dd, J=6.9, 8.7 Hz), 1.30 (3H, d, J=6.6 Hz), 1.24 (3H, t, J=7.1 Hz). MS (ES) m/e 498.1 (M+H)⁺.

Step 2

Reaction of the product of Step 1 (8.1.1) with cyclohexylamine by the procedure of Example 2, Step 4 gave the product. ¹H NMR (300 MHz, CDCl₃) δ 7.43 (1H, d, J=2.1 Hz), 7.17 (1H, dd, J=8.4, 2.1 Hz), 6.86 (1H, d, J=8.4 Hz), 5.19 (2H, m), 4.30 (1H, m), 4.27 (1H, t, J=6.6 Hz), 3.99 (2H, m), 3.89 (1H, d, J=8.7 Hz), 3.88 (3H, s), 3.73 (1H, m), 3.61 (1H, dd, J=6.9, 9.6 Hz), 1.92 (2H, m), 1.59 (3H, m), 1.38 (3H, m), 1.34 (3H, d, J=6.6 Hz), 1.27 (3H, t, J=7.1 Hz), 1.15 (3H, m). MS (ES) m/e 517.1 (M+H)⁺.

Reaction of the product of Step 1 with cyclopentylamine by the procedure of Example 2, Step 4 gave the following example.

8A

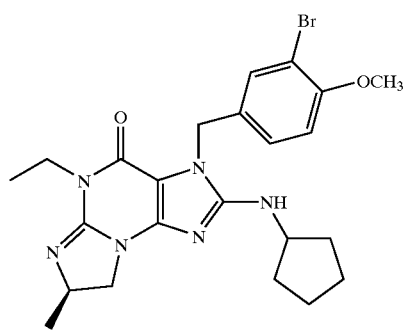

¹H NMR (300 MHz, CDCl₃) δ 7.43 (1H, d, J=1.8 Hz), 7.16 (1H, dd, J=8.4, 1.8 Hz), 6.85 (1H, d, J=8.4 Hz), 5.18 (2H, m), 4.28 (1H, m), 4.13 (2H, m), 3.97 (3H, m), 3.88 (3H, s), 3.61 (1H, dd, J=6.6, 9.3 Hz), 1.97 (2H, m), 1.57 (4H, m), 1.34 (3H, d, J=6.3 Hz), 1.31 (2H, m), 1.26 (3H, t, J=7.1 Hz). MS (ES) m/e 503.1 (M+H)⁺.

Example 9

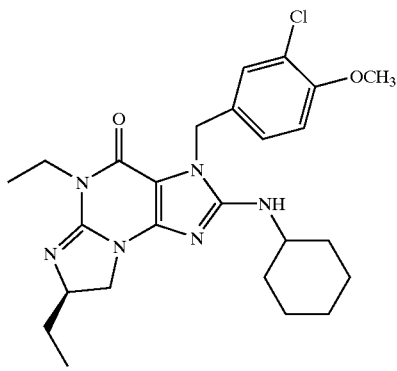

Step 1

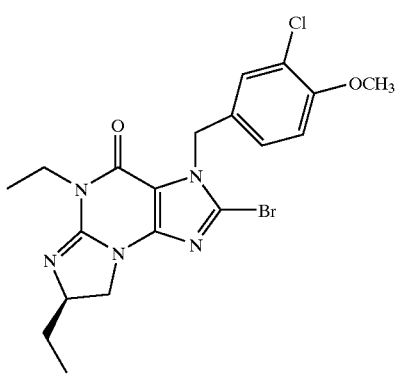

Subjection of Preparation 6 to essentially the same sequence of reactions described in Example 1, Steps 1–3 gave the product. $^1$H NMR (300 MHz, CDCl$_3$) δ 7.42 (1H, d, J=2.1 Hz), 7.31 (1H, dd, J=8.7, 2.1 Hz), 6.88 (2H, d, J=8.7 Hz), 5.40 (2H, s), 3.95–4.15 (4H, m), 3.88 (3H, s), 3.68 (1H, dd, J=6.6, 9.0 Hz), 1.75 (1H, m), 1.58 (1H, m), 1.27 (3H, t, J=7.1 Hz), 0.95 (3H, t, J=7.5 Hz). MS (ES) m/e 468.1 (M+H)$^+$ Step 2

Reaction of the product of Step 1 (9.1.1) with cyclohexylamine by the procedure of Example 2, Step 4 gave the product. $^1$H NMR (300 MHz, CDCl$_3$) δ 7.26 (1H, d, J=2.1 Hz), 7.13 (1H, dd, J=8.7, 2.1 Hz), 6.89 (1H, d, J=8.7 Hz), 5.19 (2H, s), 3.91–4.13 (5H, m), 3.89 (3H, s), 3.72 (2H, m), 1.91 (3H, m), 1.78 (1H, m), 1.55–1.62 (4H, m), 1.37 (2H, m), 1.26 (3H, t, J=7.1 Hz), 1.10 (2H, m), 0.97 (3H, t, J=7.4 Hz). MS (ES) m/e 485.1 (M+H)$^+$.

Example 10

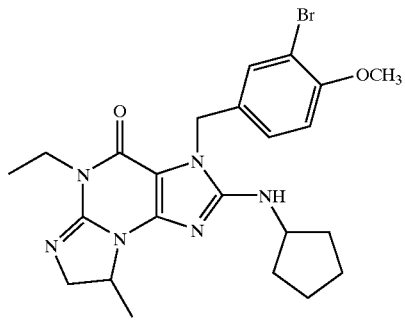

Step 1

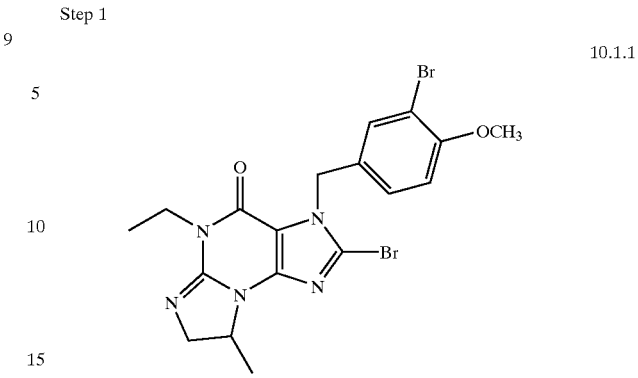

Subjection of Preparation 7 to essentially the same sequence of reactions described in Example 1, Steps 1–3, except that 3-bromo-4-methoxybenzyl bromide (Preparation 8) was used as alkylating agent in Step 3, gave the product. $^1$H NMR (300 MHz, CDCl$_3$) δ 7.57 (1H, m), 7.32 (1H, m), 6.81 (1H, m), 5.35 (2H, m), 4.50 (2H, m), 4.06 (1H, m), 3.98 (2H, m), 3.82 (3H, s), 3.48 (1H, m), 1.46 (2H, d, J=6.3 Hz), 1.22 (3H, t, J=7.1 Hz). MS (ES) m/e 498.1 (M+H)$^+$.

Step 2

Reaction of the product of Step 1 (10.1.1) with cyclopentylamine by the procedure of Example 2, Step 4 gave the product. $^1$H NMR (300 MHz, CDCl$_3$) δ 7.43 (1H, d, J=1.8 Hz), 7.18 (1H, dd, J=8.4, 1.8 Hz), 6.85 (1H, d, J=8.4 Hz), 5.21 (1H, d, J=15.9 Hz), 5.15 (1H, d, J=15.9 Hz), 4.57 (1H, m), 4.06–4.16 (3H, m), 3.99 (2H, q, J=6.9 Hz), 3.87 (3H, s), 3.53 (1H, dd, J=12.9, 6.0 Hz), 1.96 (2H, m), 1.58 (4H, m), 1.52 (3H, d, J=6.3 Hz), 1.35 (2H, m), 1.26 (3H, t, J=6.9 Hz). MS (ES) m/e 503.1 (M+H)$^+$.

Example 11

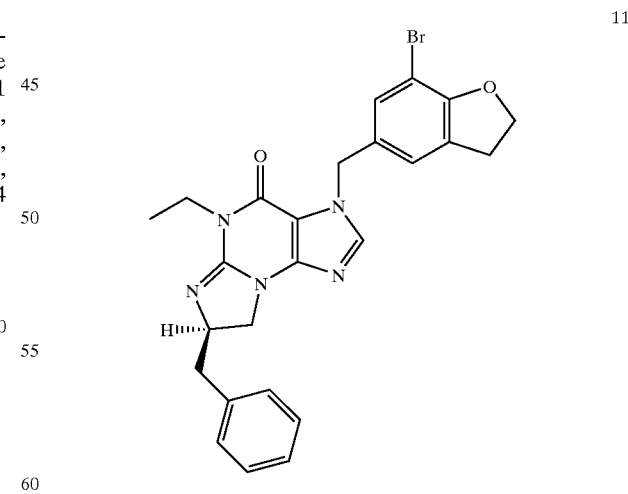

Reaction of 1.1.1 with Preparation 11 by essentially the same procedure of Example 1, Step 3 afforded the product. $^1$H NMR (300 MHz, CDCl$_3$) δ 7.39 (1H, s), 7.23–7.29 (6H, m), 7.13 (1H, s), 5.30 (2H, s), 4.67 (2H, m), 4.48 (1H, m), 4.12 (2H, q, J=7.2 Hz), 4.00–4.10 (1H, m), 3.94 (1H, m), 3.82 (1H, m), 3.29 (2H, m), 3.20 (1H, m), 2.73 (1H, m), 1.31 (3H, t, J=7.2 Hz). MS (ES, m/e) 506, 508 (M+1).

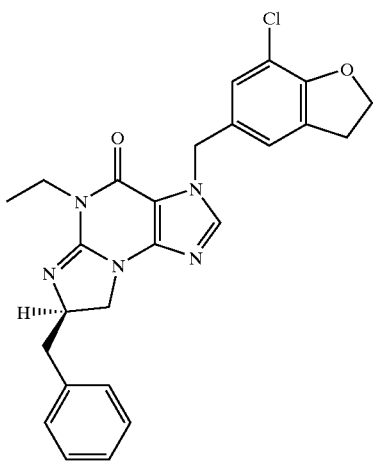

11A

Reaction of 1.1.1 with Preparation 10 by the procedure of Example 1, Step 3 gave Example 11A. $^1$H NMR (300 MHz, CDCl$_3$) δ 7.37 (s, 1H), 7.15–7.35 (m, 5H), 7.07 (s, 2H), 5.28 (s, 2H), 4.64 (m, 2H), 4.45 (m, 1H), 3.75–4.10 (m, 4H), 3.18–3.28 (m, 3H), 2.70 (m, 1H), 1.29 (m, 3H). MS (ES, m/e): 462 (M+1).

Example 12

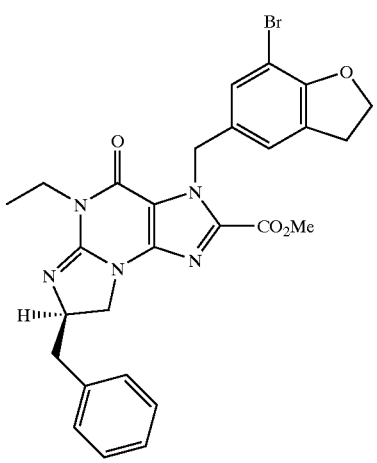

12

To a solution of Example 11 (100 mg, 0.20 mmol) in THF (10 ml) at −78° C. was added 2M LDA in THF (0.2 ml, 0.4 mmol). The mixture was stirred for 25 min, then methyl chloroformate (60 mg, 0.4 mmol) was added. The mixture was stirred in the cold for 25 min, quenched with sat'd NaHCO$_3$, cooling was removed and the product was extracted with EtOAc. The organic layer was dried (Na$_2$SO$_4$), filtered and evaporated. Subjection of the residue to flash chromatography (85:15 EtOAc/hexanes) gave the product (35 mg, 31%). $^1$H NMR (300 MHz, CDCl$_3$) δ 7.18–7.33 (7H, m), 7.18 (1H, s), 5.92 (2H, s), 4.64 (2H, m), 4.55 (1H, m), 4.20–3.83 (7H, m), 3.30–3.20 (m, 3H), 2.70 (1H, m), 1.32 (3H, m). MS (ES, m/e): 564, 566 (M+1).

Using Example 11A and essentially the same procedure, Example 12A was prepared.

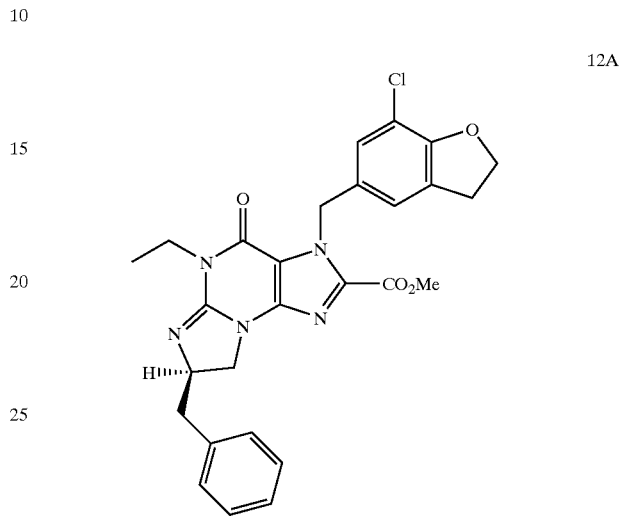

12A $^1$H NMR (CDCl$_3$, 300 MHz): δ 7.20–7.30 (5H, m), 7.18 (1H, s), 7.14 (1H, s), 5.93 (2H, s), 4.65 (2H, t), 4.55 (1H, m), 3.85–4.20 (7H, m), 3.20–3.30 (3H, m), 2.74 (1H, m), 1.33 (3H, m). MS (ES, m/e): 520 (M+1).

Example 13

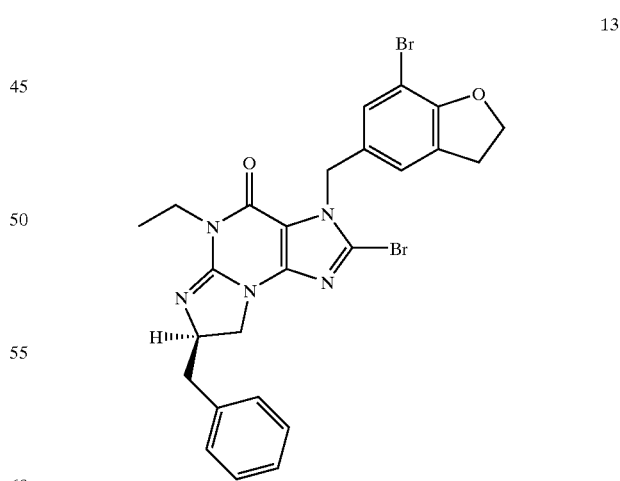

13

Reaction of 1.2.1 with Preparation 11 by the procedure of Example 1, Step 3 gave the product. $^1$H NMR (300 MHz, CDCl$_3$) δ 7.38–7.18 (7H, m), 5.36 (2H, s), 4.65 (2H, m), 4.48 (1H, m), 4.17–3.77 (4H, m), 3.28–3.18 (3H, m), 2.70 (1H, m), 1.30 (3H, m). MS (ES, m/e): 586 (M+1).

Similarly prepared was Example 13A by use of Preparation 12.

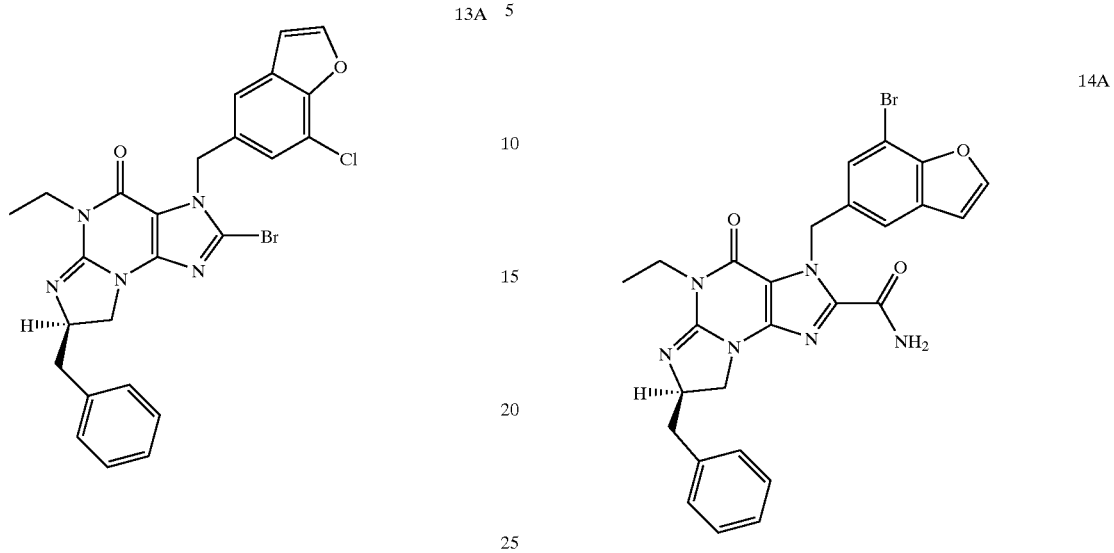

13A

¹H NMR (300 MHz, CDCl₃) δ 7.69 (1H, m), 7.53 (1H, s), 7.36 (1H, s), 7.33–7.20 (5H, m), 6.80 (1H, m), 5.54 (2H, s), 4.50 (1H, m), 4.08 (2H, m), 3.93 (1H, m), 3.82 (1H, m), 3.21 (1H, m), 2.73 (1H, m), 1.31 (3H, m). MS (ES, m/e): 538, 540 (M+1).

Example 14

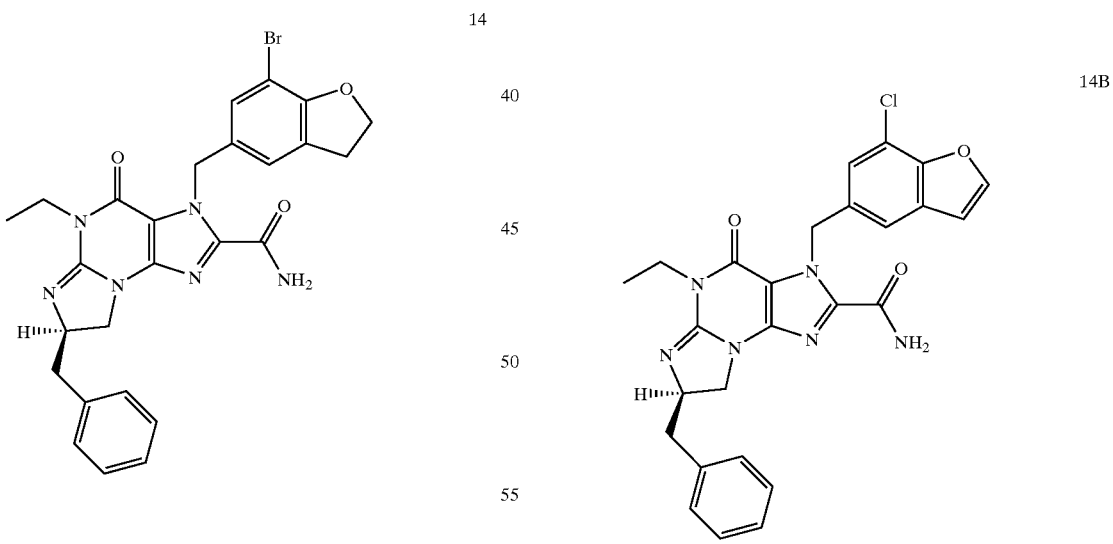

14

Example 12 (50 mg, 0.089 mmol) was dissolved in 7N NH₃ in MeOH (5 ml) and stirred for 48 h. The volatiles were evaporated and the residue purified by PTLC (EtOAc) to give the product (39 mg, 80%). ¹H NMR (300 MHz, CDCl₃) δ 7.42–7.18 (7H, m), 5.95 (2H, s), 5.80 (1H, b), 4.62 (2H, m), 4.52 (1H, m), 4.07 (2H, m), 3.90 (1H, m) 3.75 (1H, m), 3.20–3.30 (3H, m), 2.72 (1H, m), 1.31 (3H, m). MS (ES, m/e): 549, 551 (M+1).

Examples 14A and 14B were prepared by use of Preparations 13 and 12, respectively, and essentially the same sequence of reactions.

14A

¹H NMR (300 MHz, CDCl₃) δ 7.71 (1H, m), 7.65 (2H, m), 7.38–7.18 (5H, m), 6.79 (1H, m), 6.13 (2H, s), 5.80 (1H, b), 4.73 (1H, m), 4.10 (2H, m), 3.91 (1H, m), 3.75 (1H, m), 3.23 (1H, m), 2.72 (1H, m), 1.31 (3H, m). MS (ES, m/e): 547,549 (M+1).

14B

¹H NMR (300 MHz, CDCl₃) δ 7.67 (1H, s), 7.64 (1H, m), 7.48 (1H, s), 7.38–7.18 (5H, m), 6.76 (1H, m), 6.13 (2H, s), 5.87 (1H, b), 4.52 (1H, m), 4.00–4.18 (2H, m), 3.90 (1H, m), 3.75 (1H, m), 3.23 (1H, m), 2.70 (1H, m), 1.32 (3H, m). MS (ES, m/e): 503 (M+1).

Example 15

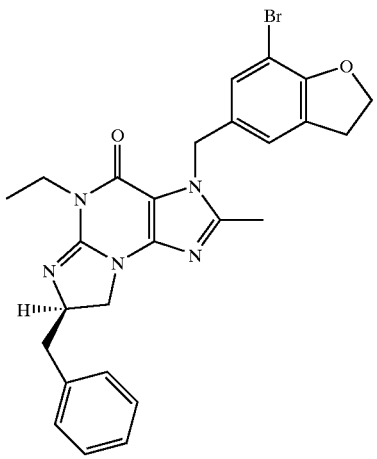

15

Step 1

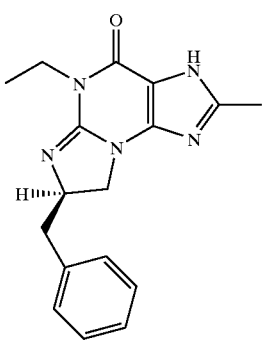

15.1.1

A flask containing the product of Example 1, Step 2 (1.2.1) (175 mg, 0.46 mmol) and Pd(PPh$_3$)$_2$Cl$_2$ (5 mg, 0.007 mmol) was purged with N$_2$ and charged with THF (15 ml). To the mixture was added 2M Al(CH$_3$)$_3$ in hexanes (0.47 ml, 0.94 mmol), and the reaction mixture was stirred for 7 h. Additional Pd(PPh$_3$)$_2$Cl$_2$ (20 mg, 0.03 mmol) and 2M Al(CH$_3$)$_3$ in hexanes (1 ml, 2.0 mmol) was added, and the reaction mixture was heated at 50° C. for 18 h. The reaction mixture was allowed to cool, poured into water, and extracted with EtOAC. The organic layer was dried (Na$_2$SO$_4$), filtered and evaporated. Subjection of the residue to PTLC (8:92 MeOH/CH$_2$Cl$_2$) gave the product (110 mg, 77%). $^1$H NMR (300 MHz, CDCl$_3$) δ 7.21–7.27 (m, 5H), 4.50 (m, 1H), 4.08 (m, 2H), 3.97 (m, 1H), 3.85 (m, 1H), 3.20 (m, 2H), 2.73 (m, 1H), 2.47 (s, 3H), 1.31 (t, J=7.2 Hz, 3H).

Step 2
Reaction of the product of Step 1 with Preparation 11 by the procedure of Example 1, Step 3 gave the product. $^1$H NMR (300 MHz, CDCl$_3$) δ 7.20–7.35 (m, 5H), 7.10 (s, 1H), 6.99 (s, 1H), 5.35 (s, 2H), 4.65 (t, 2H), 4.45 (m, 1H), 3.80–4.15 (m, 4H), 3.20–3.30 (m, 3H), 2.72 (dd, 1H), 2.37 (s, 3H), 1.31 (t, 3H). MS (ES, m/e): 520, 522 (M+1).

Example 16

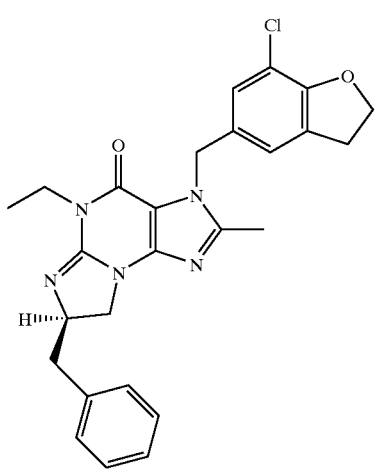

16

Reaction of Example 15, Step 1 (15.1.1) with Preparation 10 by the procedure of Example 1, Step 3 gave the product. $^1$H NMR (300 MHz, CDCl$_3$) δ 7.20–7.33 (m, 5H), 6.94 (s, 1H), 5.34 (s, 2H), 4.65 (t, 2H), 4.45 (m, 1H), 3.80–4.10 (m, 4H), 3.20–3.28 (m, 3H), 2.70 (dd, 1H), 2.36 (s, 3H), 1.31 (t, 3H). MS (ES, m/e): 476 (M+1).

Example 17

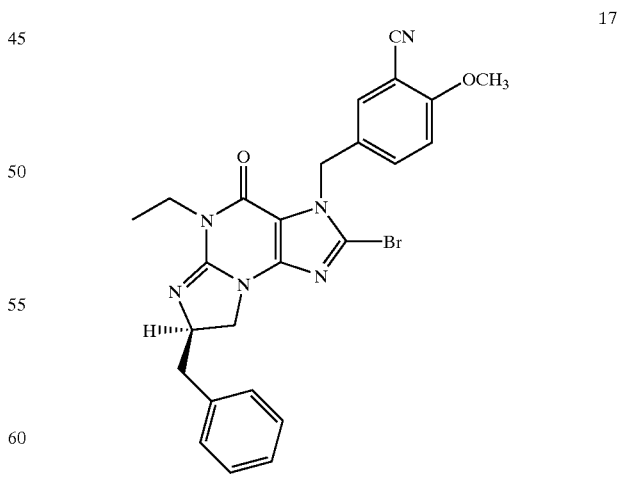

17

The product of Example 1, Step 2 (1.2.1) was alkylated with 3-cyano-4-methoxybenzyl bromide as described in Example 1, Step 3. ¹H NMR (CDCl₃, 300 MHz) δ 7.62 (1H, dd, J=2.2, 8.8 Hz), 7.56 (1H, d, J=2.2 Hz), 7.32–7.18 (5H, m), 6.94 (1H, d, J=8.8 Hz), 5.40 (2H, s), 4.47 (1H, m), 4.02 (2H, m), 3.92 (1H, m), 3.91 (3H, s), 3.79 (1H, dd, J=9.9, 6.5 Hz), 3.20 (1H, dd, J=13.5, 4.5 Hz), 2.70 (1H, dd, J=13.5, 8.8 Hz), 1.29 (3H, t, J=7.2 Hz). MS (ES) m/e 519 (M+H)⁺.

Example 18

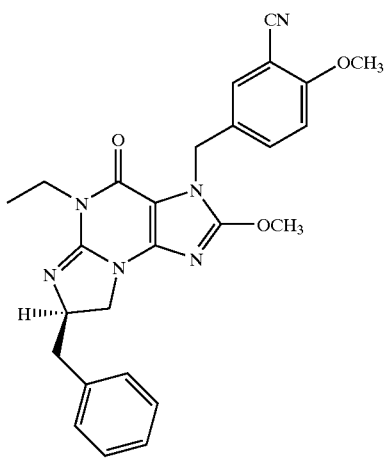

18

The product of Example 17 was reacted with excess NaOMe in MeOH/DMF to afford the product. ¹H NMR (CDCl₃, 300 MHz) δ 7.63 (1H, dd, J=2.2, 8.8 Hz), 7.52 (1H, d, J=2.2 Hz), 7.30–7.16 (5H, m), 6.90 (1H, d, J=8.8 Hz), 5.11 (2H, s), 4.45 (1H, m), 4.07 (3H, s), 3.99 (2H, m), 3.87 (3H, s), 3.86 (1H, t, J=9.3 Hz), 3.71 (1H, dd, J=6.5, 9.8 Hz), 3.21 (1H, dd, J=4.9, 13.2 Hz), 2.65 (1H, dd, J=9.3, 13.2 Hz), 1.27 (3H, t, J=6.9 Hz). MS (ES) m/e 471 (M+H)⁺.

Example 19

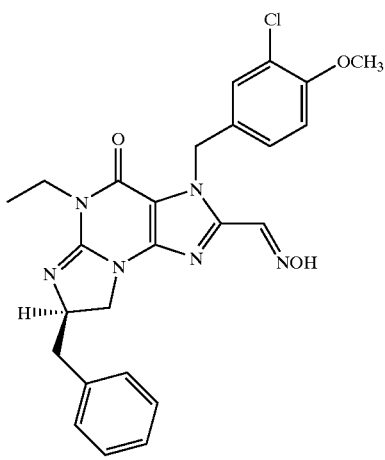

19

Step 1

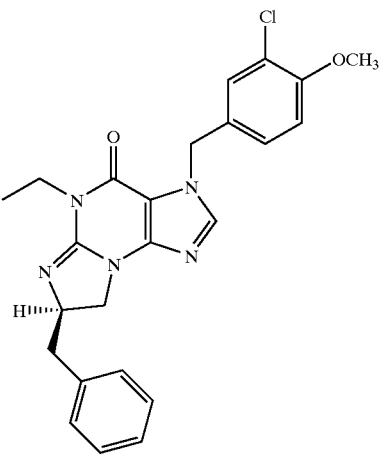

19.1.1

The product of Example 1, Step 1 (1.1.1) was alkylated with Preparation 9 using essentially the procedure of Example 1, Step 3 to afford the product. MS m/e 450 (M+H).

Step 2

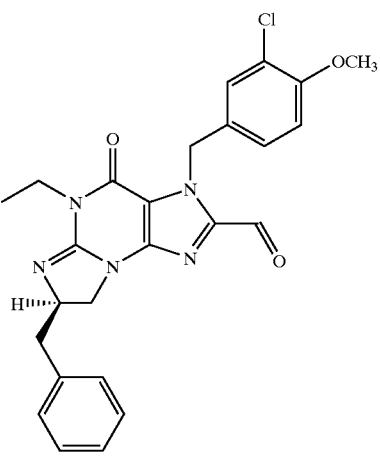

19.2.1

To a solution of 19.1.1 (200 mg, 0.44 mmol) in dry THF (4 ml) under N₂ at −78° C., was added a solution of LDA (2 M in THF, 0.29 ml). After stirring for 30 min, DMF (0.067 ml, 0.89 mmol) was added. The reaction mixture was stirred for 30 min at −78° C. and warmed to RT. After quenching with saturated NH₄Cl, the mixture was extracted with EtOAc (×3). The combined organic layers were washed with brine, dried (Na₂SO₄), filtered and concentrated. PTLC (5:95 MeOH/CH₂Cl₂) of the residue gave the product (45 mg, 21%). ¹HNMR (300 MHz, CDCl₃) δ 9.81 (1H, s), 7.22–7.43 (7H, m), 6.85 (1H, d, J=8.7 Hz), 5.86 (2H, s), 4.08 (2H, m), 3.97 (1H, m), 3.86 (3H, s), 3.82 (1H, m), 3.25 (1H, m), 2.72 (1H, m), 1.32 (3H, t, J=6.9 Hz).

Step 3

19.2.1 (45 mg, 0.09 mmol) was dissolved in THF (1 ml) and NH₂OH.HCl (10 mg, 0.14 mmol) was added, followed by aqueous NaOH (1N, 0.3 ml). After stirring at room temperature for 2 h, the mixture was diluted with CH₂Cl₂, dried (Na₂SO₄) and concentrated. PTLC (5:95 MeOH/CH₂Cl₂) gave the product (26.9 mg, 58%). ¹HNMR (300 MHz, CDCl₃) δ 8.14 (1H, s), 7.13–7.28 (7H, m), 6.77 (1H, d, J=8.4 Hz,), 5.74 (2H, s), 4.48 (1H m), 3.90–4.03 (3H, m), 3.82 (m, 1H), 3.80 (s, 3H), 3.19 (1H, dd, J=13.5, 4.2 Hz), 2.70 (1H, dd, J=13.5, 9.3 Hz), 1.25 (3H, s, J=6.9 Hz). MS (ES) m/e 493.1 (M+H)+.

The following examples were prepared by adapting procedures described in earlier examples, or by methods known to those skilled in the art.

17

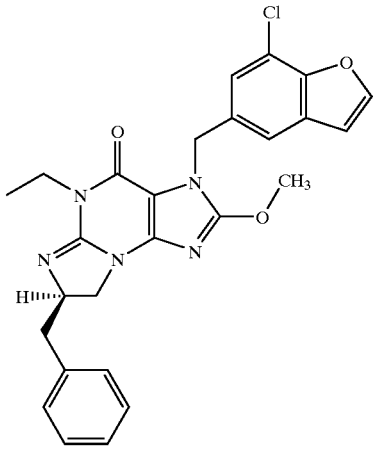

$^1$H NMR (300 MHz, CDCl$_3$) δ 7.67 (1H, m), 7.56 (1H, s), 7.34 (1H, s), 7.33–7.20 (5H, m), 6.79 (1H, m), 5.27 (2H, s), 4.50 (1H, m), 4.18–4.00 (2H, m), 4.10 (3H, s), 3.92 (1H, m), 3.76 (1H, m), 3.23 (1H, m), 2.73 (1H, m), 1.31 (3H, m). MS (ES, m/e): 490 (M+1).

18

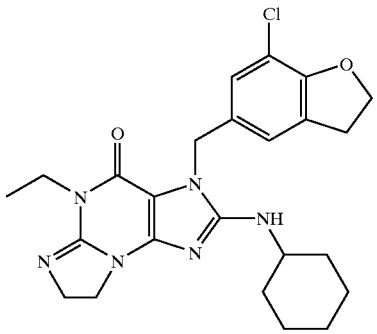

$^1$H NMR (400 MHz, CDCl$_3$) δ 6.99 (2H, d, J=4 Hz), 5.16 (2H, s), 4.66 (2H, t), 4.09–3.92 (7H, m), 3.72 (1H, m), 3.24 (2H, t), 1.92 (2H, m), 1.57 (2H, m), 1.38–1.06 (9H, m). HRMS: Calcd for C$_{24}$H$_{30}$ClN$_6$O$_2$: 469.2119, Found: 469.2116.

19

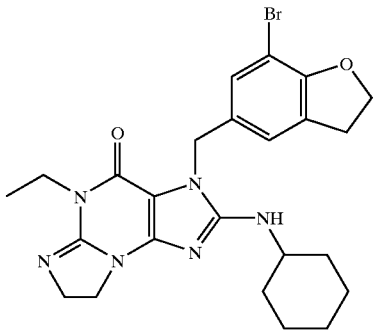

$^1$H NMR (400 MHz, CDCl$_3$) δ 7.14 (1H, s), 7.02 (1H, s), 5.16 (2H, s), 4.65 (2H, m), 4.09–3.93 (7H, m), 3.72 (1H, m), 3.26 (2H, m), 1.91 (2H, m), 1.58 (2H, m), 1.38–1.07 (9H, m). HRMS: Calcd for C$_{24}$H$_{30}$BrN$_6$O$_2$: 513.1614, Found: 513.1608.

20

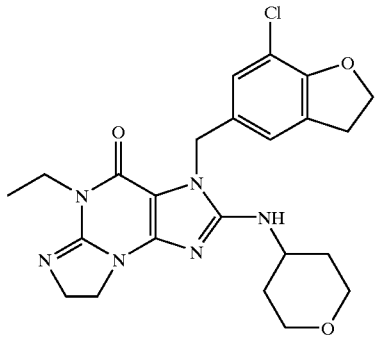

$^1$H NMR (400 MHz, CDCl$_3$) δ 6.98 (2H, s), 5.18 (2H, s), 4.67 (2H, m), 4.07–3.87 (10H, m), 3.51 (3H, m), 3.25 (2H, m), 1.94 (2H, m), 1.39 (2H, m), 1.25 (3H, m). HRMS: Calcd for C$_{23}$H$_{28}$ClN$_6$O$_3$: 471.1911, Found: 471.1912.

21

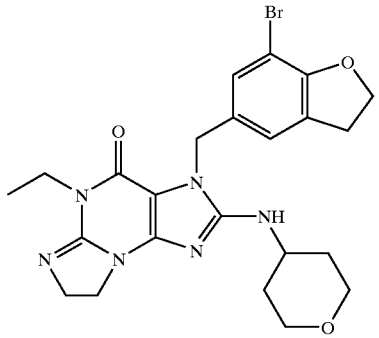

$^1$H NMR (400 MHz, CDCl$_3$) δ 7.13 (1H, s), 7.02 (1H, s), 5.18 (2H, s), 4.66 (2H, m), 4.06–3.88 (10H, m), 3.48 (2H, m), 3.27 (2H, m), 1.94 (2H, m), 1.37 (2H, m), 1.27 (3H, m). HRMS: Calcd for C$_{23}$H$_{28}$BrN$_6$O$_3$: 515.1406, Found: 515.1398.

22

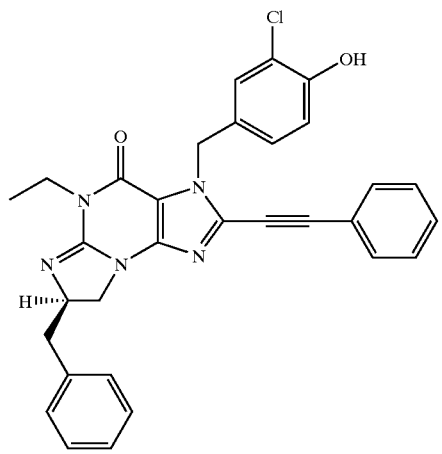

$^1$H NMR (300 MHz, CDCl$_3$) δ 7.73–7.16 (12H, m), 7.02–6.93 (1H, m), 6.48–6.43 (1H, b), 5.50 (2H, s), 4.61–4.43 (1H, m), 4.21–3.82 (4H, m), 3.31–3.17 (1H, m), 2.72–2.66 (1H, m), 1.38–1.23 (3H, m). LC-MS calculated for $C_{31}H_{26}ClN_5O_2$ [MH$^+$]=536; Observed: 536.

23

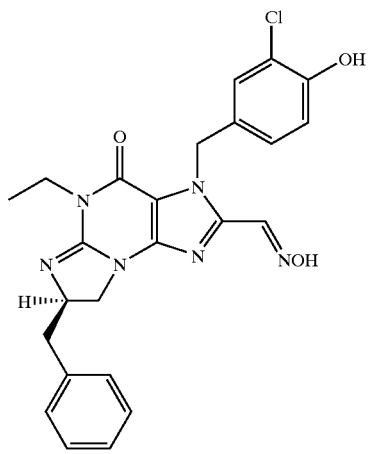

$^1$H NMR (300 MHz, CDCl$_3$) δ 8.13 (s, 1H), 7.21–7.30 (6H, m), 7.12 (1H, m), 6.93 (1H, d, J=8.1 Hz), 5.73 (2H, s), 4.51 (1H, m), 3.91–4.07 (3H, m), 3.84 (1H, m), 3.23 (1H, dd, J=13.5, 4.2 Hz), 2.72 (1H, m), 1.29 (3H, t, J=6.9 Hz).

24

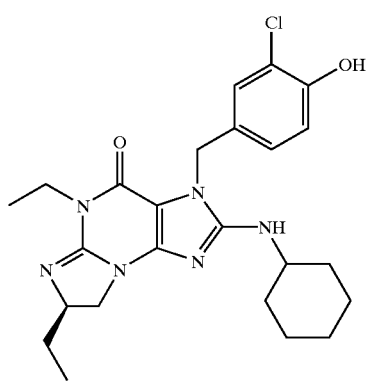

$^1$H NMR (300 MHz, CDCl$_3$) δ 7.15 (1H, d, J=1.8 Hz), 6.99 (1H, dd, J=8.4, 1.8 Hz), 6.87 (1H, d, J=8.4 Hz), 5.12 (2H, s), 4.20 (1H, d, J=8.1 Hz), 4.00 (2H, q, J=6.9 Hz), 3.94 (2H, m), 3.70 (2H, m), 1.87 (2H, m), 1.73 (1H, m), 1.54 (4H, m), 1.31 (2H, m), 1.22 (3H, t, J=6.9 Hz), 1.09 (3H, m), 0.93 (3H, t, J=7.5 Hz). MS (ES) m/e 471.1 (M+H)$^+$.

25

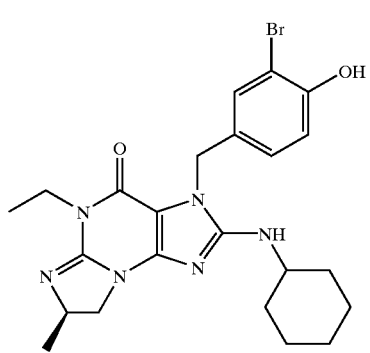

$^1$H NMR (300 MHz, CDCl$_3$) δ 7.31 (1H, d, J=1.8 Hz), 6.99 (1H, dd, J=8.4, 1.8 Hz), 6.86 (1H, d, J=8.4 Hz), 5.12 (2H, m), 4.27 (1H, m), 4.17 (1H, m), 3.92 (2H, q, J=6.9 Hz), 3.61 (2H, m), 1.86 (2H, m), 1.57 (2H, m), 1.31 (3H, d, J=6.3 Hz), 1.26 (2H, m), 1.21 (3H, t, J=6.9 Hz), 1.09 (4H, m). MS (ES) m/e 503.1 (M+H)$^+$.

26

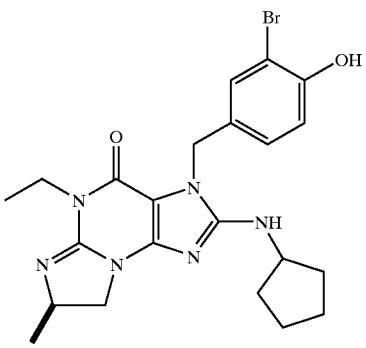

$^1$H NMR (300 MHz, CDCl$_3$) δ 7.29 (1H, d, J=1.8 Hz), 6.98 (1H, dd, J=8.4, 1.8 Hz), 6.84 (1H, d, J=8.4 Hz), 5.09 (2H, m), 4.08–4.21 (3H, m), 3.89 (2H, q, J=6.9 Hz), 3.58 (1H, dd, J=6.3, 8.7 Hz), 1.92 (2H, m), 1.33 (2H, m), 1.29 (3H, d, J=6.0 Hz), 1.19 (3H, t, J=6.9 Hz). MS (ES) m/e 489.1 (M+H)$^+$.

27

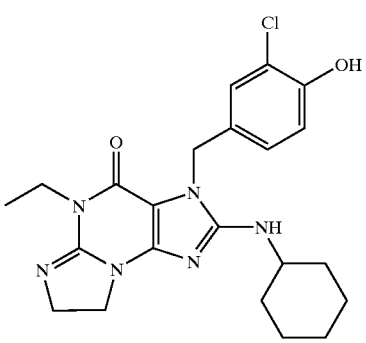

$^1$H NMR (400 MHz, CDCl$_3$) δ 7.19 (1H, s), 7.03 (1H, d, J=8 Hz), 6.97 (1H, d, J=8 Hz), 5.18 (2H, s), 4.09–3.98 (6H, m), 3.89 (1H, d, J=7 Hz), 3.72 (1H, m), 1.91 (2H, d, J=12 Hz), 1.58 (2H, m), 1.39 (2H, m), 1.25 (3H, m), 1.09 (4H, m). HRMS: Calcd for $C_{22}H_{28}ClN_6O_2$: 443.1962, Found: 443.1960.

28

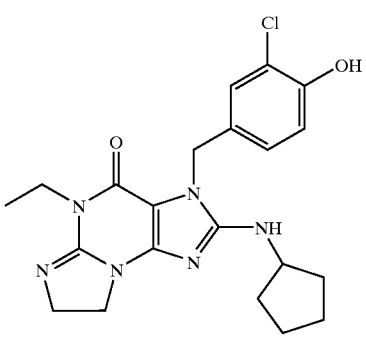

$^1$H NMR (400 MHz, CDCl$_3$) δ 7.18 (1H, s), 7.03 (1H, d, J=8 Hz), 6.96 (1H, d, J=8 Hz), 5.17 (2H, s), 4.17 (1H, m), 4.06 (2H, m), 3.99 (4H, m), 3.84 (1H, m), 1.96 (2H, m), 1.57 (4H, m), 1.25 (5H, m). HRMS: Calcd for $C_{21}H_{26}ClN_6O_2$: 429.1806, Found: 429.1813.

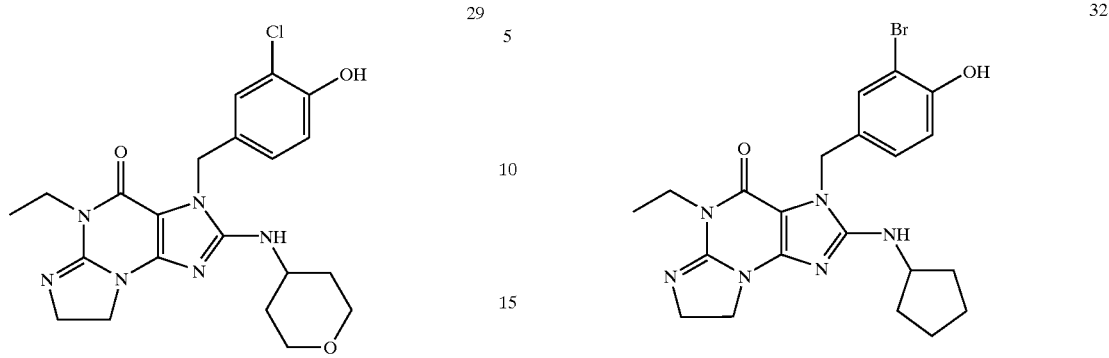

29

$^1$H NMR (CD$_3$OD, 400 MHz) δ 7.12 (1H, s), 6.91 (1H, d, J=8 Hz), 6.70 (1H, d, J=8 Hz), 5.12 (2H, s), 4.09 (2H, m), 3.91 (8H, m), 3.47 (2H, m), 1.88 (2H, m), 1.59 (2H, m), 1.20 (3H, m). HRMS: Calcd for $C_{21}H_{26}ClN_6O_3$: 445.1755, Found: 445.1748.

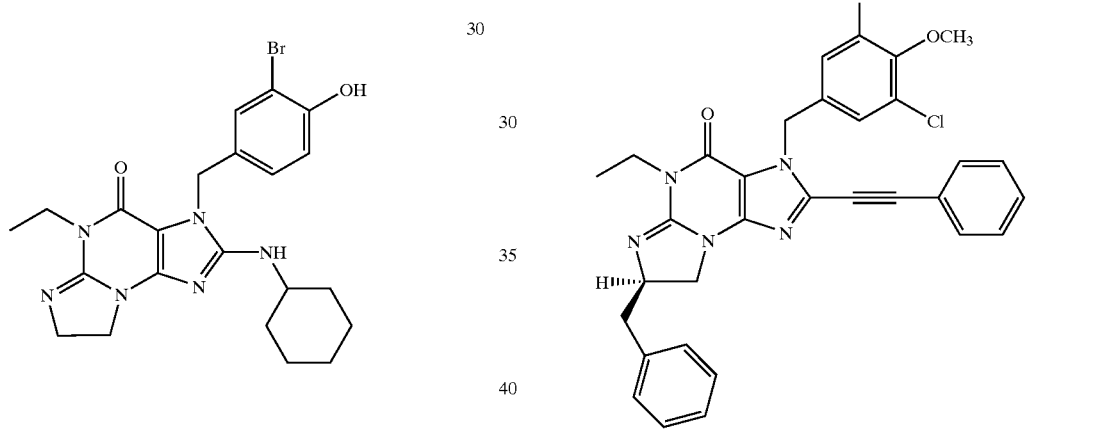

30

$^1$H NMR (CDCl$_3$, 400 MHz) δ 7.34 (1H, s), 7.05 (1H, d, J=8 Hz), 6.96 (1H, d, J=8 Hz), 5.17 (2H, s), 4.12 (2H, m), 4.00 (5H, m), 3.72 (1H, m), 1.91 (2H, m), 1.58 (2H, m), 1.37–1.08 (9H, m). HRMS: Calcd for $C_{22}H_{28}BrN_6O_2$: 487.1457, Found: 487.1452.

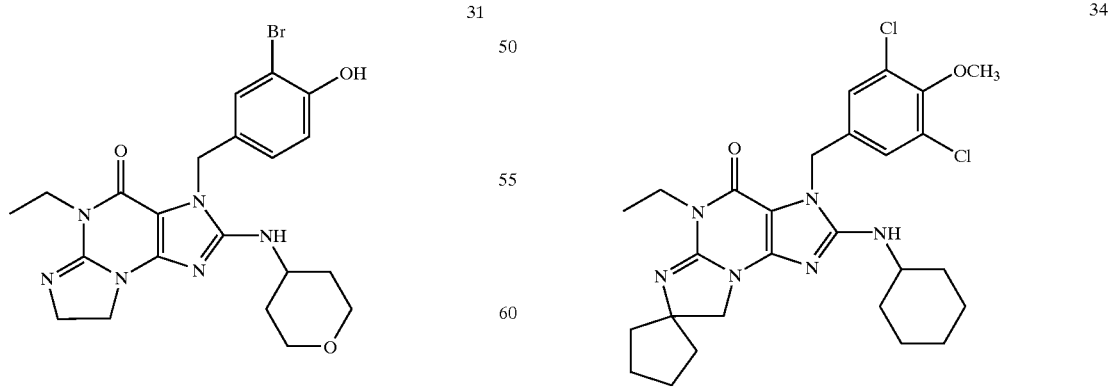

31

$^1$H NMR (CD$_3$OD, 400 MHz) δ 7.33 (1H, s), 6.98 (1H, d, J=8 Hz), 6.72 (1H, d, J=8 Hz), 5.13 (2H, s), 4.06 (2H, m), 3.88 (7H, m), 3.47 (2H, m), 1.89 (2H, m), 1.60 (2H, m), 1.20 (3H, m). HRMS: Calcd for $C_{21}H_{26}BrN_6O_3$: 489.1250, Found: 489.1245

32

$^1$H NMR (400 MHz, CD$_3$OD) δ 7.32 (1H, s), 6.97 (1H, d, J=8 Hz), 6.72 (1H, d, J=8 Hz), 5.13 (2H, s), 4.20 (1H, m), 4.07 (2H, m), 3.89 (4H, m), 1.96 (2H, m), 1.70–1.49 (6H, m), 1.20 (3H, m). HRMS: Calcd for $C_{21}H_{26}BrN_6O_2$: 473.1301, Found: 473.1307.

33

$^1$H NMR (CDCl$_3$, 300 MHz) δ 7.59 (2H, m), 7.38–7.48 (5H, m), 5.51 (2H, s), 4.05 (2H, m), 3.87 (5H, m), 1.8–2.0 (4H, m), 1.6–1.75 (4H, m), 1.29 (3H, m). MS (ES, m/e): 548 (M+1).

34

$^1$H NMR (CDCl$_3$, 300 MHz) δ 7.13 (2H, s), 5.18 (2H, s), 3.98 (2H, q), 3.86 (3H, s), 3.84 (2H, s), 3.75 (1H, m), 1.0–2.0 (21H, m). MS (ES, m/e): 545 (M+1).

35

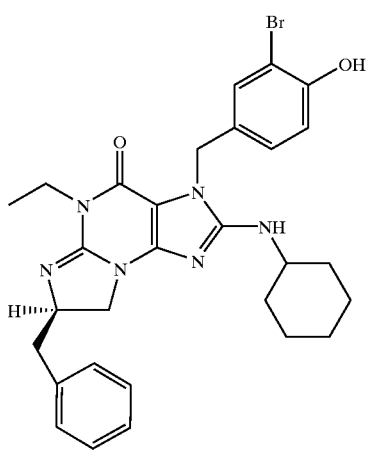

89

¹H NMR (CDCl₃) δ 7.36–7.15 (6H, m), 7.03–6.97 (1H, dd), 6.91–6.85 (1H, dd), 5.18 (2H, s), 4.58–4.43 (1H, m), 4.12–3.83 (4H, m), 3.85–3.74 (1H, m), 3.72–3.60 (1H, m), 3.32–3.21 (1H, dd), 2.76–2.63 (1H, dd), 1.93–1.81 (2H, b), 1.63–1.48 (3H, b), 1.41–0.97 (5H, m), 1.31–1.22 (3H, t). MS calculated for $C_{29}H_{33}BrN_6O_2$ [MH+]=578; Observed: 578.

36

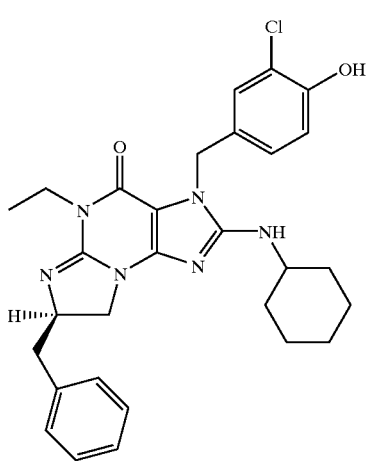

¹H NMR (CDCl₃) δ 7.40–7.13 (7H, m), 6.97 (2H, s), 5.17 (2H, s), 4.62–4.45 (1H, m), 4.18–3.58 (6H, m), 3.37–3.23 (1H, m), 2.83–2.68 (1H, dd), 1.93–1.80 (2H, d), 1.66–1.47 (3H, b), 1.31–1.22 (3H, t), 1.40–1.00 (5H, m). MS calculated for $C_{29}H_{33}ClN_6O_2$ [MH+]=533; Observed: 533.

37

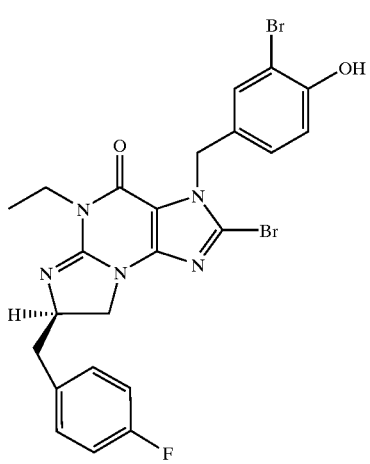

¹H NMR (CDCl₃) δ 7.39–7.37 (1H, d), 7.23–7.12 (3H, m), 7.00–6.91 (3H, m), 5.37 (2H, s), 4.52–4.39 (1H, m), 4.13–3.87 (3H, m), 3.83–3.74 (1H, dd), 3.18–3.07 (1H, dd), 2.78–2.66 (1H, dd), 1.34–1.23 (3H, m). MS calculated for $C_{23}H_{20}BrClFN_5O_2$ [MH+]=578; Observed: 578.

38

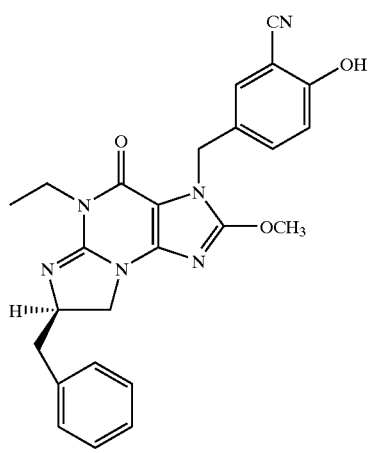

¹H NMR (CDCl₃, 300 MHz) δ 7.32–7.14 (7H, m), 6.68 (1H, d, J=8.8 Hz), 5.05 (1H, br), 4.94 (2H, s), 4.46 (1H, m), 4.04 (3H, s), 4.01–3.82 (3H, ser.m.), 3.72 (1H, m), 3.19 (1H, dd, J=3.8, 13.2 Hz), 2.65 (1H, dd, J=9.3, 13.2 Hz), 1.21 (3H, t, J=6.8 Hz).

39

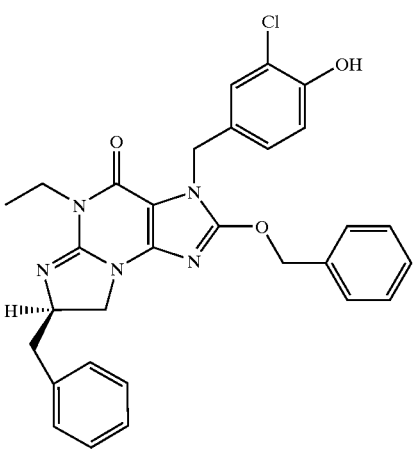

¹H NMR (CDCl₃, 300 MHz) δ 7.39 (5H, s), 7.34–7.14 (7H, m), 6.88 (1H, d, J=8.8 Hz), 5.43 (2H, s), 5.11 (2H, s), 4.50 (1H, m), 4.03 (2H, m), 3.92 (1H, t, J=9.8 Hz), 3.77 (1H, dd, J=7.2, 9.8 Hz), 3.25 (1H, dd, J=4.4, 13.7 Hz), 2.69 (1H, dd, J=9.3, 13.7 Hz), 1.28 (3H, t, J=6.8 Hz), MS (ES) m/e 542 (M+H)⁺.

Example 40

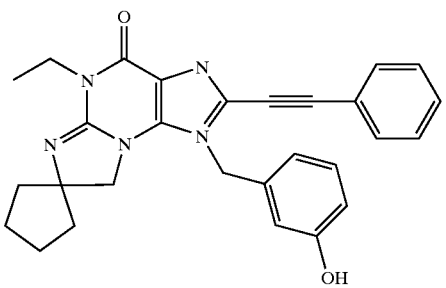

-continued

Step 1

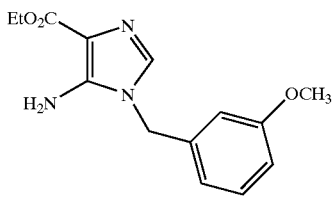

40.1.1

A mixture of ethyl aminocyanoacetate (10 g, 78 mmol) and triethyl orthoformate (11.5 g, 78 mmol) was refluxed in acetonitrile (150 ml) for 1 h. The reaction mixture was cooled to RT and 3-methoxybenzylamine (10 g, 73 mmol) was added, followed by diisopropylethylamine (10 ml). The reaction mixture was refluxed for 2 h, allowed to cool, and concentrated. The residue was dissolved in 1N HCl (200 ml) and washed with $CH_2Cl_2$ (2×100 ml). To the aqueous layer was added $NaHCO_3$ until the pH was 8. The aqueous layer was extracted with ethyl acetate and the organic extract was dried ($Na_2SO_4$), filtered and evaporated. Recrystallization of the residue (EtOAc) gave the product (8.5 g, 47%). $^1$H NMR (300 MHz, $CDCl_3$) δ 7.30 (1H, m), 7.14 (1H, s), 6.89 (1H, m), 6.73 (1H, m), 6.67 (1H, s), 4.96 (2H, s), 4.70 (2H, s), 3.34 (2H, m), 3.78 (3H, s), 1.39 (3H, m).

Step 2

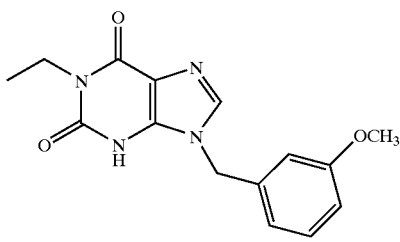

40.2.1

A mixture of 40.1.1 (8.0 g, 31 mmol), ethylisocyanate (8.7 g, 122 mmol), triethylamine (12.3 g, 122 mmol) and toluene (80 ml) was heated at 100° C. in a sealed tube overnight. The solvent was concentrated to about 40 ml and the residue was cooled in ice. The precipitate was collected, washed with ether and dried. The precipitate was dissolved in methanol (120 ml) and sodium methoxide (6.5 g, 122 mmol) was added. The reaction mixture was refluxed for 3 h. Methanol was removed and the residue was dissolved in water (100 ml). The solution was acidified to pH 5 and the resultant white precipitate was collected, washed with water and dried under vacuum to give the product (8.7 g, 94%). $^1$H NMR (300 MHz, $CD_3OD$) δ 8.03 (1H, s), 7.16 (1H, m), 6.67–6.80 (3H, m), 5.14 (2H, s), 3.88 (2H, m), 3.65 (3H, s), 1.08 (3H, m).

Step 3

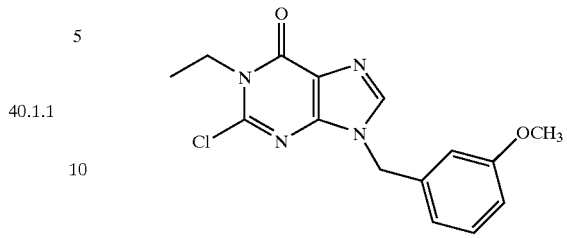

40.3.1

40.2.1 (7.7 g, 27 mmole) in $POCl_3$ (100 ml) was refluxed for 5 h. Excess phosphorus oxychloride was removed via vacuum and the residue was dissolved in ethyl acetate (200 ml). The organic solution was washed with saturated $NHCO_3$ and dried over $Na_2SO_4$. The product was subjected to flash chromatography (1:5 EtOAc/hexanes) to give the product (4.3 g, 53%). $^1$H NMR (300 MHz, $CDCl_3$) δ 7.71 (1H, s), 7.29 (1H, m), 6.9–6.8 (3H, m), 5.24 (2H, s), 4.21 (2H, m), 3.80 (3H, s), 1.40 (3H, m).

Step 4

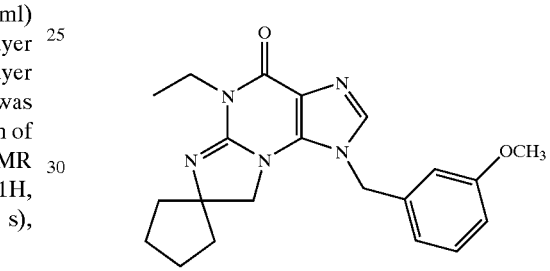

40.4.1

A mixture of 40.3.1 (100 mg, 0.31 mmol), 1-amino-1-cyclopentanemethanol (109 mg, 0.94 mmol) and diisopropylethylamine (160 mg, 12.4 mmol) in 1 ml NMP (1 ml) was heated at 110° C. overnight. Water (5 ml) was added and the reaction was cooled in ice. The resultant white precipitate was collected by filtration, washed with water and dried under vacuum. To the precipitate in $CH_2Cl_2$ (15 ml) was added methanesulfonyl chloride (102 mg, 0.94 mmol) and triethylamine (156 mg, 1.55 mmol). The mixture was stirred at RT overnight. $CH_2Cl_2$ (40 ml) was added and the whole was washed with water, dried ($Na_2SO_4$), filtered and evaporated. The residue was subjected to PTLC (90:10 $CH_2Cl_2$/MeOH) to give the product. $^1$H NMR (300 MHz, $CDCl_3$) δ 7.38–7.24 (2H, m), 6.90 (1H, m), 6.60 (2H, m), 5.22 (2H, s), 4.04 (2H, m), 3.78 (3H, s), 3.67 (2H, s), 1.9–1.7 (4H, m), 1.6–1.4 (4H, m), 1.24 (3H, m). MS (ES, m/e) 380 (M+1).

Step 5

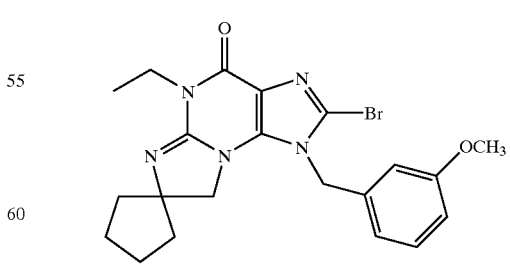

40.5.1

40.4.1 (104 mg, 0.27 mmol) was dissolved in $CH_2Cl_2$ (10 ml) and N-bromosuccinimide (73.5 mg, 0.41 mmol) was added. The reaction mixture was stirred at RT for 0.5 h. The solvent was removed and the residue was subjected to flash chromatography (gradient: CH₂Cl₂ to 95:5 CH₂Cl₂/MeOH) to give the product. ¹H NMR (300 MHz, CDCl₃) δ 7.28 (1H, m), 6.85 (1H, m), 6.55–6.58 (2H, m), 5.25 (2H, s), 3.97 (2H, m), 3.76 (3H, s), 3.65 (2H, s), 1.9–1.7 (4H, m), 1.6–1.4 (4H, m), 1.20 (3H, m). MS (ES, m/e): 458 (M+1).

Step 6

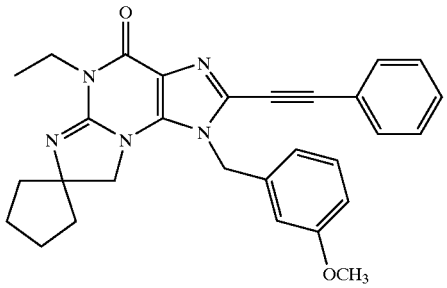

40.6.1

A nitrogen-purged flask was charged with a mixture of 40.5.1 (110 mg, 0.24 mmole), trans-dichloro-bis(triphenylphosphine) palladium (50 mg, 0.071 mmol) and copper(I) iodide (4.5 mg, 0.02 mmol). N,N-Dimethylformamide (2 ml), phenylacetylene (117 mg, 0.72 mmol) and triethylamine (24 mg, 0.24 mmol) was added. The reaction was stirred at RT overnight. The solvent was removed and the residue was partitioned between CH₂Cl₂ (50 ml) and saturated NaHCO₃ solution (25 ml). The organic layer was washed with water, dried (Na₂SO₄), filtered and evaporated. The residue was subjected to PTLC (95:5 CH₂Cl₂/MeOH) to give the product. ¹H NMR (300 MHz, CDCl₃) δ 7.4–7.2 (6H, m), 6.85 (1H, m), 6.6–6.7 (2H, m), 5.38 (2H, s), 3.98 (2H, m), 3.75 (3H, s), 3.68 (2H, s), 1.7–1.9 (4H, m), 1.4–1.6 (4H, m), 1.22 (3H, m). MS (ES, m/e) 480 (M+1).

Step 7

To a solution of 40.6.1 (50 mg, 0.10 mmol) in CH₂Cl₂ (10 ml) was added boron tribromide (0.1 ml). The white cloudy suspension was stirred at RT for 2.5 h. Saturated NaHCO₃ solution (20 ml) was added and the product was extracted with CH₂Cl₂ (50 ml), dried (Na₂SO₄), filtered and evaporated. The product was obtained after PTLC (90:10 CH₂Cl₂/MeOH). ¹H NMR (300 MHz, CDCl₃) 7.4–7.1 (6H, m), 6.75 (1H, m), 6.55 (1H, m), 6.47 (1H, s), 5.31 (2H, s), 3.89 (2H, m), 3.64 (2H, s), 1.6–1.8 (4H, m), 1.5–1.3 (4H, m), 1.15 (3H, m). MS (ES, m/e): 466 (M+1).

Using appropriate starting materials and synthetic steps similar to those outlined in Example 40, the following compounds were prepared:

41

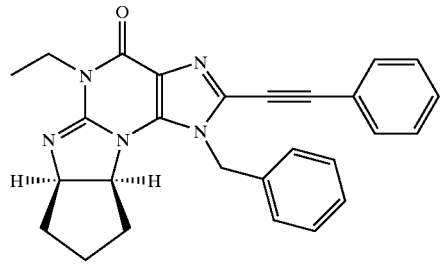

¹H NMR (300 MHz, CDCl₃) δ 7.44–7.26 (8H, m), 7.10 (2H, d, J=6.6 Hz), 5.70 (1H, d, J=17.1 Hz), 5.21 (1H, d, J=17.1 Hz), 4.63 (1H, m), 4.44 (1H, m), 4.04 (1H, m), 2.05–1.59 (6H, m), 1.30 (2H, m), 1.26 (3H, t, J=6.9 Hz). MS (ES) m/e 436.1 (M+H)⁺.

42

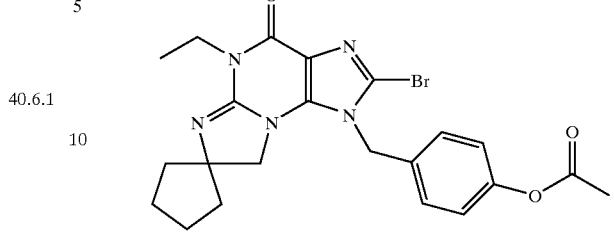

¹H NMR (300 MHz, CDCl₃) δ 7.14 (2H, d, J=9.0 Hz), 7.06 (2H, d, J=9.0 Hz), 5.29 (2H, s), 4.00 (2H, q, J=6.9 Hz), 3.65 (2H, s), 2.29 (3H, s), 1.79 (4H, m), 1.49 (4H, m), 1.23 (3H, t, J=6.9 Hz). MS (ES) m/e 486.1 (M+H)⁺.

43

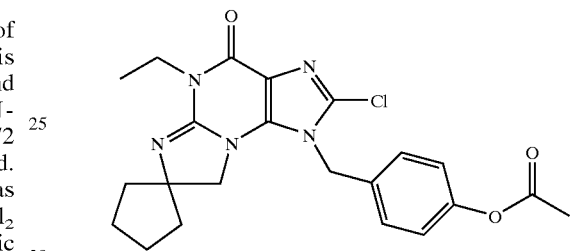

¹H NMR (300 MHz, CDCl₃) δ 7.15 (2H, d, J=8.5 Hz), 7.07 (2H, d, J=8.5 Hz), 5.28 (2H, s), 4.02 (2H, q, J=6.9 Hz), 3.65 (2H, s), 2.29 (3H, s), 1.82 (4H, m), 1.50 (4H, m), 1.24 (3H, t, J=6.9 Hz). MS (ES) m/e 486.1 (M+H)⁺.

44

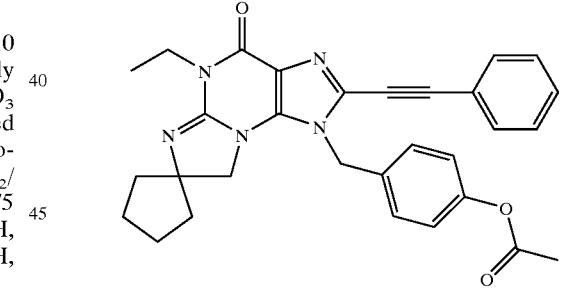

¹H NMR (300 MHz, CDCl₃) δ 7.46–7.27 (m, 5H), 7.16 (4H, m), 5.42 (2H, s), 4.03 (2H, q, J=6.9 Hz), 3.66 (2H, s), 2.30 (3H, s), 1.82 (4H, m), 1.50 (4H, m), 1.25 (3H, t, J=6.9 Hz). MS (ES) m/e 508.1 (M+H)⁺.

45

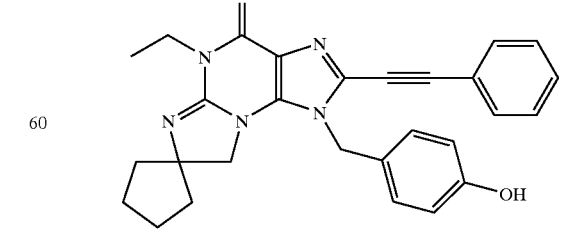

¹H NMR (300 MHz, CDCl₃) δ 7.39 (2H, m), 7.24 (3H, m), 6.88 (2H, d, J=8.5 Hz), 6.75 (2H, d, J=8.5 Hz), 5.26 (2H, s), 3.89 (2H, q, J=6.9 Hz), 3.64 (2H, s), 1.72 (4H, m), 1.41 (4H, m), 1.14 (3H, t, J=6.9 Hz). MS (ES) m/e 466.1 (M+H)$^+$.

Pharmaceutically Acceptable Dosage Forms

The compounds of the present invention may be administered to humans or other mammals by a variety of routes, including oral dosage forms and injections (intravenous, intramuscular, intraperitoneal, subcutaneous, and the like). Numerous other dosage forms containing the compounds of the present invention can be readily formulated by one skilled in the art, utilizing the suitable pharmaceutical excipients (or carriers) as defined below. For considerations of patient compliance, oral dosage forms are generally most preferred.

The rate of systemic delivery can be satisfactorily controlled by one skilled in the art, by manipulating any one or more of the following:

(a) the active ingredient proper;

(b) the pharmaceutically acceptable excipient(s), so long as the variants do not interfere in the activity of the particular active ingredient selected;

(c) the type of excipient(s), and the concomitant desirable thickness and permeability (swelling properties) of the excipient(s);

(d) the time-dependent conditions of the excipient(s);

(e) the particle size of the granulated active ingredient; and (f) the pH-dependent conditions of the excipient(s).

Pharmaceutically acceptable excipients (or carriers) include flavoring agents, pharmaceutical-grade dyes or pigments, solvents, co-solvents, buffer systems, surfactants, preservatives, sweetener agents, viscosity agents, fillers, lubricants, glidants, disintegrants, binders and resins.

Conventional flavoring agents may be used, such as those described in *Remington's Pharmaceutical Sciences*, 18$^{th}$ Ed., Mack Publishing Co., pp. 1288–1300 (1990), which is incorporated in its entirety by reference herein. The pharmaceutical compositions of the invention generally contain from about 0 to 2% of flavoring agents.

Conventional dyes and/or pigments may also be used, such as those described in the *Handbook of Pharmaceutical Excipients*, by the American Pharmaceutical Association & the Pharmaceutical Society of Great Britain, pp. 81–90 (1986), which is incorporated in its entirety by reference herein. The pharmaceutical compositions of the invention generally contain from about 0 to 2% of dyes and/or pigments.

The pharmaceutical compositions of the invention generally contain from about 0.1 to 99.9% of solvent(s). A preferred solvent is water. Preferred co-solvents include ethanol, glycerin, propylene glycol, polyethylene glycol, and the like. The pharmaceutical compositions of the invention may include from about 0 to 50% of co-solvents.

Preferred buffer systems include acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred buffers are phosphoric, tartaric, citric and acetic acids and salts thereof. The pharmaceutical compositions of the invention generally contain from about 0 to 5% of a buffer.

Preferred surfactants include polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the invention generally contain from about 0 to 2% of surfactants.

Preferred preservatives include phenol, alkyl esters of parahydroxybenzoic acid, o-phenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methyl paraben and propyl paraben. Particularly preferred preservatives are the salts of benzoic acid, cetylpyridinium chloride, methyl paraben and propyl paraben. The pharmaceutical compositions of the invention generally include from about 0 to 2% of preservatives.

Preferred sweeteners include sucrose, glucose, saccharin, sorbitol, mannitol and aspartame. Particularly preferred sweeteners are sucrose and saccharin. Pharmaceutical compositions of the invention generally include from about 0 to 5% of sweeteners.

Preferred viscosity agents include methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred viscosity agents are methylcellulose, carbomer, xanthan gum, guar gum, povidone, sodium carboxymethylcellulose, and magnesium aluminum silicate. Pharmaceutical compositions of the invention generally include from about 0 to 5% of viscosity agents.

Preferred fillers include lactose, mannitol, sorbitol, tribasic calcium phosphate, diabasic calcium phosphate, compressible sugar, starch, calcium sulfate, dextro and microcrystalline cellulose. Pharmaceutical compositions of the invention generally contain from about 0 to 75% of fillers.

Preferred lubricants/glidants include magnesium stearate, stearic acid and talc. Pharmaceutical compositions of the invention generally include from about 0 to 7%, preferably, about 1 to 5% of lubricants/glidants.

Preferred disintegrants include starch, sodium starch glycolate, crospovidone and croscarmelose sodium and microcrystalline cellulose. Pharmaceutical compositions of the invention generally include from about 0 to 20%, preferably, about 4 to 15% of disintegrants.

Preferred binders include acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. Pharmaceutical compositions of the invention generally include from about 0 to 12%, preferably, about 1 to 10% of binders.

Additional agents known to a skilled formulator may be combined with the compounds of the invention to create a single dosage form. Alternatively, additional agents may be separately administered to a mammal as part of a multiple dosage form.

For preparing pharmaceutical compositions containing the inventive compounds, inert, pharmaceutically acceptable excipients or carriers can be either solid or liquid. Solid form preparations include powders, tablets, dispersible granules, capsules, cachets and suppositories. The powders and tablets may be comprised of from about 5 to 95 weight percent of active ingredient. Suitable solid carriers are known in the art, for example, magnesium carbonate, magnesium stearate, talc, sugar and lactose. Tablets, powders, cachets and capsules can be used as solid dosage forms suitable for oral administration. Examples of pharmaceutically acceptable carriers and methods of manufacture for various compositions may be found in *Remington's Pharmaceutical Sciences*, 18$^{th}$ Ed., Mack Publishing Co. (1990), which is incorporated in its entirety by reference herein.

Liquid form preparations include solutions, suspensions and emulsions. Common liquid form preparations include water and water-propylene glycol solutions for parenteral injection or addition of sweeteners and opacifiers for oral solutions, suspensions and emulsions. Liquid form preparations may also include solutions for intranasal administration.

Aerosol preparations suitable for inhalation include solutions and solids in powder form, which may be combined with a pharmaceutically acceptable carrier, such as an inert compressed gas (e.g., nitrogen).

Also included are solid form preparations that may be converted, shortly before use, to liquid form preparations for either oral or parenteral administration. Such liquid forms include solutions, suspensions and emulsions.

The compounds of the invention may also be delivered transdermally. The transdermal compositions can take the form of creams, lotions, aerosols and emulsions and may be included in a transdermal patch of a matrix or reservoir type as is conventional in the art for this purpose.

The preferred mode of administering the compounds of the invention is oral. Preferably, the pharmaceutical preparation is in a unit dosage form. In such a form, the preparation is subdivided into suitable sized unit doses containing appropriate quantities of the active component, for example, an effective amount to achieve the desired purpose.

The quantity of active ingredient (compound) in a unit dose of preparation may be varied or adjusted from about 0.01 to 4,000 mg, preferably, from about 0.02 to 1,000 mg, more preferably, from about 0.3 to 500 mg, and most preferably, from about 0.04 to 250 mg, according to the particular application. A typical recommended daily dosage regimen for oral administration can range from about 0.02 to 2,000 mg/day, in two to four divided doses. For convenience, the total daily dosage may be divided and administered in portions during the day as required. Typically, pharmaceutical compositions of the invention will be administered from about 1 to 5 times per day, or alternatively, as a continuous infusion. Such administration can be used as a chronic or acute therapy. The amount of active ingredient that may be combined with carrier materials to produce a single dosage form will vary depending upon the host treated and the particular mode of administration. A typical preparation will contain from about 5 to 95% of active compound (w/w). Preferably, such preparations will contain from about 20 to 80 wt. % of active compound.

The pharmaceutically acceptable carriers employed in conjunction with the compounds of the present invention are used at a concentration sufficient to provide a practical size to dosage relationship. The pharmaceutically acceptable carriers, in total, may comprise from about 0.1 to 99.9% by weight of the pharmaceutical compositions of the invention, preferably, from about 20 to 80% by weight.

Upon improvement of a patient's condition, a maintenance dose of a compound, composition or combination of the invention may be administered, if applicable. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art. The amount and frequency of the administration of compounds of the invention or their pharmaceutically acceptable salts may be regulated according to the judgment of the attending clinician, based on the factors recited above. As a skilled artisan will appreciate, lower or higher doses than those recited above may be required.

For example, it is often the case that a proper dosage level is based on the weight of the patient. For instance, dosage levels of between about 0.01 and 100 mg/kg of body weight per day, preferably, between about 0.5 and 75 mg/kg of body weight per day, and more preferably, between about 1 and 50 mg/kg of body weight per day, of the inventive compounds, compositions and salts thereof described herein, are therapeutically useful for the treatment of a variety of biological disorders, particularly, male and female sexual dysfunction.

The inventive compounds are understood to provide efficacious treatment of (male) erectile dysfunction, including a reasonable time of onset upon administration, and a reasonable duration after administration. For example, in the treatment of erectile dysfunction, a dosage of the inventive compound may be taken about an hour before a sex act is to be undertaken. Particular dosages will work within about thirty minutes of their administration. Ideal dosages will affect a patient within about fifteen minutes of their administration. While food, diet, pre-existing conditions, alcohol and other systemic conditions could lengthen the time delay for an inventive drug to work after its administration, it is understood that optimum dosages in combination with sexual stimulation will result in an efficacious drug treatment within and for a reasonable amount of time.

The inventive compounds can exist in unsolvated as well as solvated forms, including hydrated forms. In general, the solvated forms, with pharmaceutically-acceptable solvents, such as water, ethanol and the like, are equivalent to the unsolvated forms for purposes of this invention.

The inventive compounds may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention.

The invention comprises a compound having the formula (I.1) or (II.1), a method for making an inventive compound, a method for making a pharmaceutical composition from at least one inventive compound and at least one pharmaceutically acceptable carrier, and a method of using one or more inventive compounds to treat a variety of disorders, symptoms and diseases. Further, the inventive compounds can be used to prepare a medicament for treating a variety of disorders, symptoms and diseases.

The inventive compounds and their pharmaceutically acceptable salt and neutral compositions may be formulated together with a pharmaceutically acceptable carrier. The resulting composition may be administered in vivo to mammals, such as men or women, to treat a variety of disorders, symptoms and diseases. For example, the inventive compounds and compositions may be used to treat diseases of the urogenital system, specifically, male erectile dysfunction (e.g., impotence) and female sexual dysfunction. Male erectile dysfunction may be defined as an inability of the male to sufficiently obtain and/or sustain an erection to have intercourse with his mate. In the treatment of erectile dysfunction, it is believed that the inventive PDE V inhibitors of formulas (I.1) and (II.1) are beneficial therapeutic agents because they elevate cGMP levels in the human body. This action facilitates corpus cavernosum smooth muscle relaxation, which provides an increased flow of blood therein and results in an erection. This makes the inventive compounds especially useful for treating impotence and other types of diseases that are affected by cGMP levels.

Accordingly, another aspect of the invention is a method for treating erectile dysfunction in a mammal in need of such treatment, comprising administering to the mammal at least one compound having the formula (I.1) or (II.1) or a pharmaceutical composition thereof in an amount effective to ameliorate and/or reduce one or more of the symptoms associated with erectile dysfunction sufficiently enough so that the mammal can complete intercourse with another mammal. An inventive compound can be used in the preparation of a medicament for treating erectile dysfunction.

Introduced in 1998 as the first pill to treat impotence, Viagra® today is the most commonly prescribed medication to treat physiologically-caused erectile dysfunction ("ED"). Certain patients, however, can experience undesirable side effects while taking Viagra®. For instance, the use of Viagra® is contraindicated to patients who are using organic nitrates, either regularly or intermittently. *Physicians' Desk Reference®*, 55$^{th}$ Ed, pp. 2534–37 (2001). Combining Viagra® with nitrates can cause a hypotensive episode or suddenly reduce blood pressure to dangerous levels, which may cause a heart attack. Id. Accordingly, men who have a heart condition that requires the use of nitrate drugs should not use Viagra®. Id. It has also been reported that Viagra® can cause a vision side effect by impairing the patient's color discrimination (blue/green), causing a "blue-halo" light visual alteration. Id. This side effect is presumably due to inhibition of the PDE VI isoenzyme (found in a retina). Id.

An advantage of the inventive compounds is that they can be particularly selective for the PDE V isoenzyme in comparison to other types of PDE isoenzymes, such as the PDE VI isoenzyme. It is believed that this increased selectivity will ameliorate side effects associated with the use of Viagra®. In particular, the high selectivity of the inventive compounds should minimize, and may even prevent, the occurrence of a "blue-halo" light visual alteration. It is believed that the increased isoenzyme selectivity in inhibiting PDE V isoenzyme (found in a penis) versus PDE VI isoenzyme (found in a retina) accounts for obviating the "blue-halo" visual side effect.

Furthermore, the inventive compounds do not adversely react with nitrate medication in a rat. It is believed the same lack of adverse interaction will apply to all mammals, including humans. An adverse reaction with nitrate medication may be dangerous and fatal. Adverse reactions include any reaction that could jeopardize or otherwise diminish the body's physiological functions. More specifically, in the case of combination therapy for a patient, comprising administering to the patient a nitrate donating agent combined with a PDE V inhibitor agent, an adverse nitrate reaction would be one in which the patient's blood pressure drops significantly more than with either agent administered alone.

This feature opens up a method of erectile dysfunction treatment to many patients who suffer from both an erectile dysfunction and a cardiovascular or other disease(s) that is treated with a nitrate donating medicament. Patients suffering from two or more different ailments that require dual (or multiple) treatments may have been born with one or both ailments, or later developed one or both ailments due to genetics or some other type of injury or disease, such as nerve damage, spinal cord injury, diabetes, and the like. Accordingly, it is another embodiment of this invention to treat a patient suffering from both (1) an erectile dysfunction and (2) at least one condition that can be treated with a nitrate donor medication, the inventive treatment comprising, a combination therapy comprising, an administration to a mammal of at least one inventive compound or a pharmaceutical composition thereof, and at least one nitrate donating compound or a pharmaceutical composition thereof. The patient suffering from both erectile dysfunction and a need for a nitrate donating medicament can be treated for both conditions sequentially, concurrently and/or simultaneously. The combination therapy can be taken separately in any form, preferably in oral or patch doses, or can be formulated together for a single, combined dosage.

The compounds of the present invention may be employed alone or in combination with other agents, particularly, other types of PDE inhibitors (especially cGMP PDE V inhibitors), prostanoids, α-adrenergic receptor, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, renin inhibitors, serotonin 5-HT$_{2c}$ receptor agonists, nociceptin receptor agonists, rho kinase inhibitors, potassium channel modulators and inhibitors of multidrug resistance protein 5.

Examples of therapeutic agents that may be used in combination with compounds of the invention are the following: PDE V inhibitors, such as sildenafil citrate (Viagra®, Pfizer, Conn., United States), Vardenafil™ (Bayer, Germany) and IC-351 (Cialis™, Lilly-ICOS, Washington and Indiana, United States); prostanoids, such as prostaglandin E$_1$; α-adrenergic agonists, such as phentolamine mesylate; dopamine receptor agonists, such as apomorphine; angiotensin II antagonists, such as losartan, irbesartan, valsartan and candesartan; and ET$_A$ antagonists, such as bosentan and ABT-627.

It is understood that other combinations may be undertaken while remaining within the scope of the invention. While one or more of the inventive compounds may be used in an application of monotherapy to treat erectile dysfunction, they also may be used in combination therapy, in which the inventive compounds are combined with one or more other pharmaceutical compounds that are useful for treating erectile dysfunction and/or other types of disorders, symptoms and diseases.

As discussed above, due to their cGMP-PDE V inhibitory activities, the inventive compounds are useful for treating urological (or urogenital) disorders, in particular, female and male sexual dysfunctions. Other physiological disorders, symptoms and diseases can also benefit from cGMP-PDE V inhibition. For example, the inventive compounds, salts and derivatives thereof may be used to treat cardiovascular and cerebrovascular diseases. Other types of disorders, symptoms and diseases can also be treated with the use of the inventive compounds. Particular indications include angina pectoris, hypertension (e.g., pulmonary hypertension, etc.), restenosis post angioplasty, endarterectomy, stent introduction, peripheral vascular diseases, cerebral stroke, respiratory tract disorders, such as reversible airway obstruction, chronic asthma and bronchitis, allergic disorders associated with atopy, such as urticaria, eczema, and rinitis, ischemic heart diseases, impaired glucose tolerance, diabetes and complications related to diabetes, such as neuropathy, insulin resistance syndrome and hyperglycemia, polycystic ovarian syndrome, glomerular diseases, renal insufficiency, nephritis, tubular interstitial disease, autoimmune diseases, glaucoma, intestinal motility disorders, cachexia, cancer, cognitive impairment and oesophageal disorders, such as nutcracker oesophagus.

An advantageous aspect of the invention is to administer the compounds of the invention to treat or prevent pulmonary hypertension in a mammal. Pulmonary hypertension is an acute or chronic pathophysiological condition induced by primary and secondary factors that increase vascular resistance. The compounds of the invention can inhibit cGMP hydrolysis in lung tissue, which results in relatively specific vasodilation of a constricted pulmonary vasculature. The inventive compounds can treat primary and secondary pulmonary hypertension, acute and chronic pulmonary hypertension, and pulmonary vascular tone. The inventive compounds can be used alone or in combination with agents that increase production of cGMP levels in lung tissue to treat pulmonary hypertension in a mammal. The inventive compounds can be co-administered with other agents, such as nitric oxide donors (e.g., nitroso, nitrosyl, nitric oxide-releasing, and other nitrogen-containing compounds, such as arginine and glyceryl trinitrate), guanylyl cyclase stimulators, atrial natriuretic peptides (e.g. ANP, BNP, CNP, DNP, etc.), endothelin antagonists (e.g., $ET_A$, $ET_B$, $ET_A/ET_B$, etc.) and prostacyclin analogues.

Another aspect of the invention is a method for treating premature ejaculation in a mammal by administering an inventive compound. U.S. Pat. No. 6,403,597 and U.S. Patent Application Publication No. 20020091129, each of which is incorporated herein in its entirety, teach the treatment of premature ejaculation with specific PDE V inhibitors. In the same way, the compounds of the formula (I.1) or (II.1) are useful for treating premature ejaculation in a mammal. Thus, the inventive compounds can be administered to a patient for treatment of male erectile dysfunction, male premature ejaculation or a combination thereof, and also for a patient that has, is or will be treated with a nitrate donating medicament.

Still another aspect of this invention is to provide a kit comprising separate containers in a single package, wherein the inventive pharmaceutical compounds, compositions and/ or salts thereof are used in combination with pharmaceutically acceptable carriers to treat disorders, symptoms and diseases where cGMP-PDE V inhibition plays a role.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:
1. A compound having the formula (I.1) or (II.1):

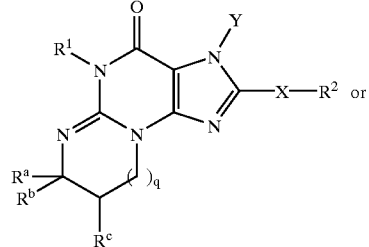

(I.1)

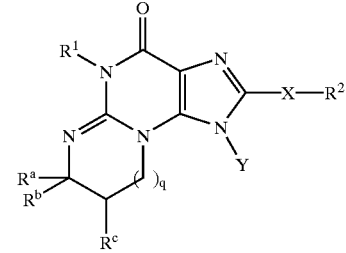

(II.1)

or a pharmaceutically acceptable salt thereof
where,
q=0 or 1;
$R^1$ is H, cycloalkyl, alkyl, $R^{23}$-alkyl- or $R^{26}$;
$R^a$, $R^b$ and $R^c$ are, independently of one another, each H, alkyl, cyoloalkyl, aryl, $R^{22}$-aryl- or $R^{24}$-alkyl-; or
$R^a$ and $R^b$, together with the carbon to which they are both attached, form a 4- to 7-membered ring, and $R^c$ is H or alkyl; or
$R^a$ and $R^c$, together with the respective carbons to which they are attached, form a 4- to 7-membered ring, and $R^b$ is H or alkyl;
(i) X is a bond;
Y is aryl-alkyl or $R^{22}$-aryl-alkyl-; and
$R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;
(ii) X is a bond;
Y is aryl-alkyl or $R^{22}$-aryl-alkyl-; and
$R^2$ is H, halo, —CONHR$^6$, —CONR$^6$R$^7$, —CO$_2$R$^6$, monohaloalkyl, polyhaloalkyl, azido, cyano, —C=N—OR$^6$, cycloalkyl, cycloalkylalkyl, $R^{26}$, aminosulfonyl, alkyl or $R^{23}$-alkyl-;
(iii) X is —O— or —S—;
Y is aryl-alkyl or $R^{22}$-aryl-alkyl-; and
$R^2$ is $R^{26}$, cycloalkyl cycloalkylalkyl, heterocycloalkyl, cycloalkenyl or $R^{26}$-alkyl-;
(iv) X is —O— or —S—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{28}$-alkyl-;
(v) X is —SO— or —SO$_2$—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{28}$-alkyl-;
(vi) X is —NR$^8$—;
Y is aryl-alkyl or $R^{22}$-aryl-alkyl-; and
$R^2$ is $(R^{29})_p$-alkyl-, cycloalkyl, $(R^{30})_p$-cycloalkyl-, cycloalkenyl, $(R^{30})_p$-cycloalkenyl-, heterocycloalkyl or $(R^{30})_p$-heterocycloalkyl-:
(vii) X is —NR$^8$—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{31}$-alkyl-; or

103

(viii) X is —C≡C—;
Y is aryl-alkyl or $R^{22}$-aryl-alkyl; and
$R^2$ is alkyl, $R^{26}$, cycloalkyl, cycloalkylalkyl or $R^{23}$-alkyl-;
where,
$R^6$ is H or $R^7$;
$R^7$ is alkyl, cycloalkyl or cycloalkylalkyl;
$R^8$ is heterocycloalkyl or $R^6$;
$R^{21}$ is 1–6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cyoloalkyl, cycloalkylalkyl, amino, alkylamino, acylamino, carboxyl, —C(O)O$R^{34}$, carboxamido, —OCF$_3$ and acyloxy;
$R^{22}$ is 1–6 substituents each independently selected from the group consisting of alkyl and $R^{21}$;
$R^{23}$ is cycloalkoxy aryloxy, alkylthio, arylthio, cycloalkyl or $R^{28}$;
$R^{24}$ is cycloalkyl or $R^{26}$;
$R^{25}$ is hydroxy, alkoxy, amino, monoalkylamino, dialkylamino or $R^{26}$;
$R^{26}$ is aryl, $R^{22}$-aryl-, heteroaryl or $R^{22}$-heteroaryl-;
$R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;
$R^{28}$ is cycloalkylamino, heterocycloalkylamino or $R^{25}$;
$R^{29}$ is alkoxy, cycloalkylamino, heterocycloalkylamino or $R^{26}$;
$R^{30}$ is halo, hydroxy, alkoxy, amino, aminosulfonyl, cyano, monohaloalkyl, polyhaloalkyl, thiol, alkylthio, alkyl, cyoloalkyl, cycloalkylalkyl or acyloxy;
$R^{31}$ is cycloalkyl or $R^{28}$;
$R^{34}$ is alkyl, aryl, aralkyl and heteroaryl; and
p is 1 to 4.

2. The compound or pharmaceutically acceptable salt according to claim 1, where $R^1$ is aryl, $R^{22}$-aryl-, alkyl or $R^{23}$-alkyl-, where $R^{22}$ and $R^{23}$ are each independently defined in claim 1.

3. The compound or pharmaceutically acceptable salt according to claim 1, where in sections (i) through (viii), respectively, $R^2$ is (i) $R^{27}$-alkyl-, (ii) $R^{23}$-alkyl-, (iii) $R^{28}$-alkyl-, (iv) alkyl or $R^{28}$-alkyl-, (v) alkyl or $R^{28}$-alkyl-, (vi) $(R^{29})_p$-alkyl-, (vii) alkyl or $R^{31}$-alkyl- or (viii) alkyl or $R^{23}$-alkyl-, where $R^{23}$, $R^{27}$, $R^{28}$, $R^{29}$, $R^{31}$ and p are each independently defined in claim 1.

4. The compound or pharmaceutically acceptable salt according to claim 1, which is

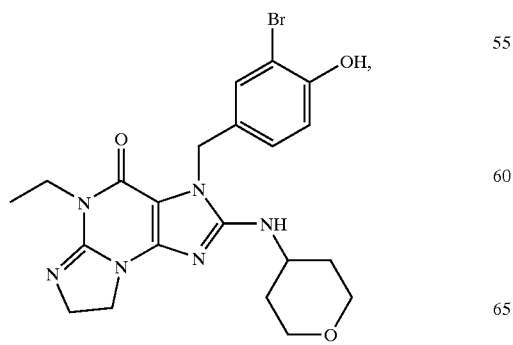

104

-continued

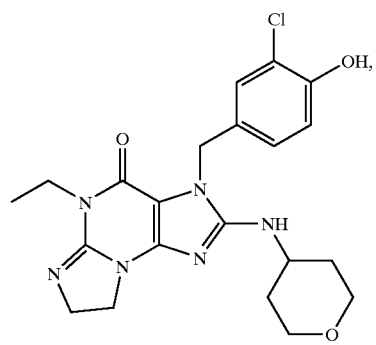

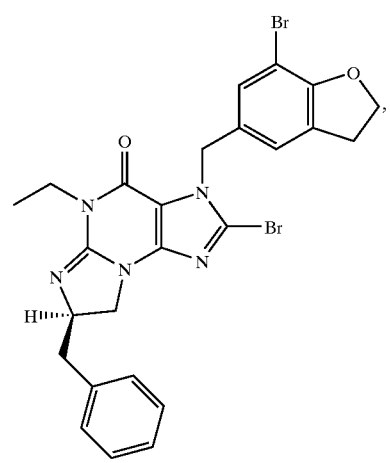

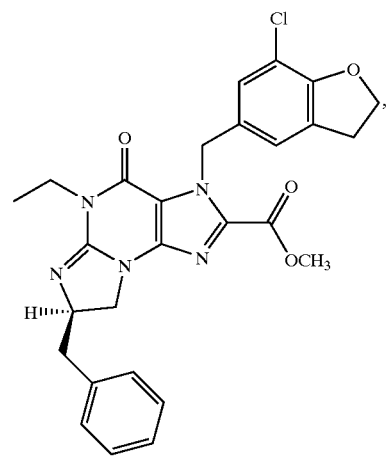

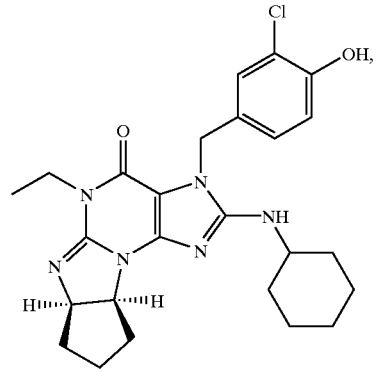

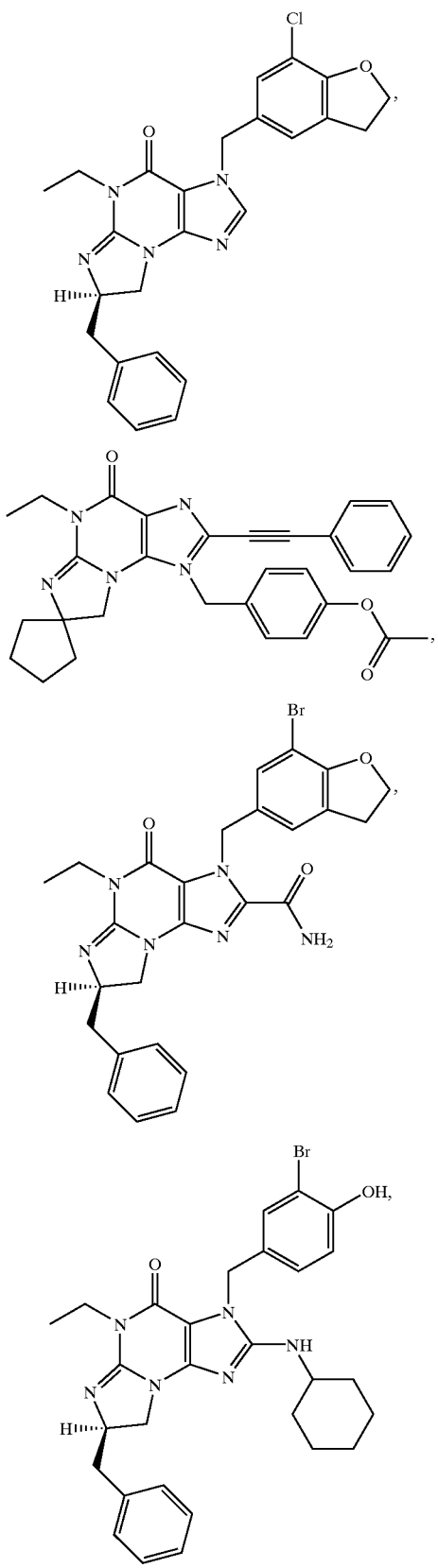
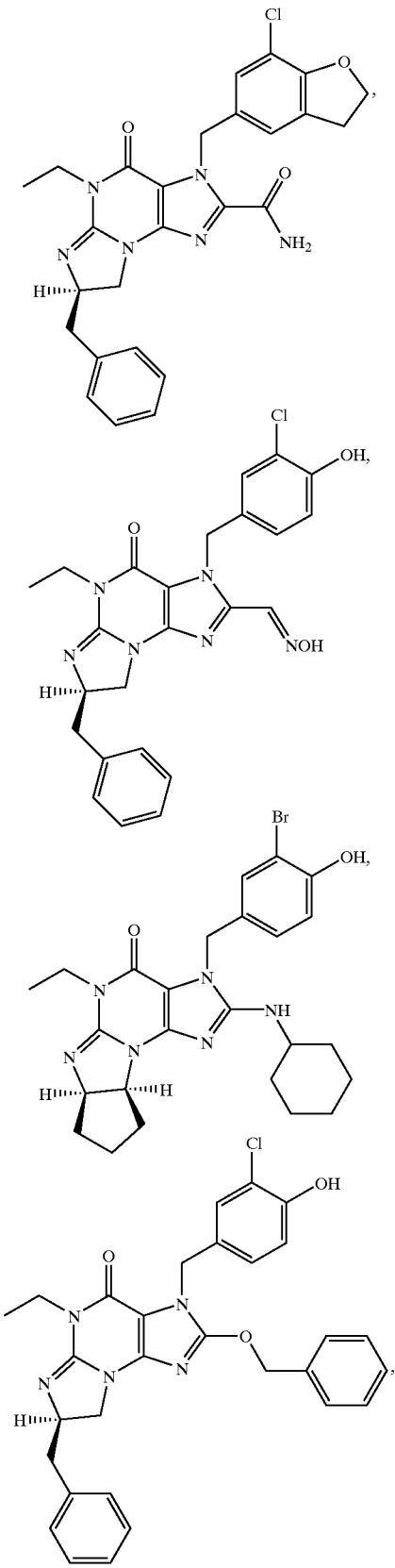

107
-continued
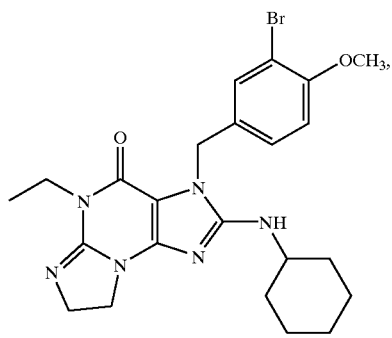
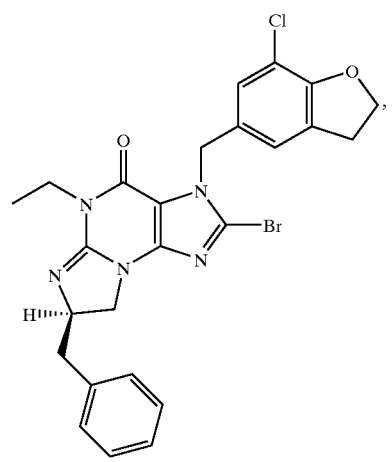
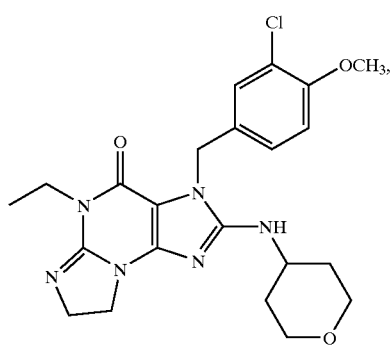
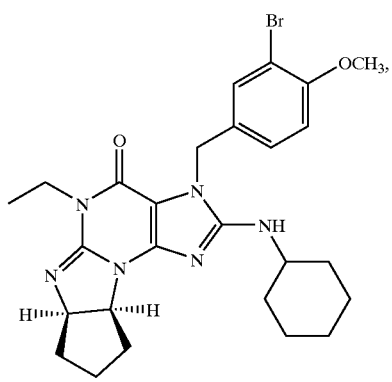
108
-continued
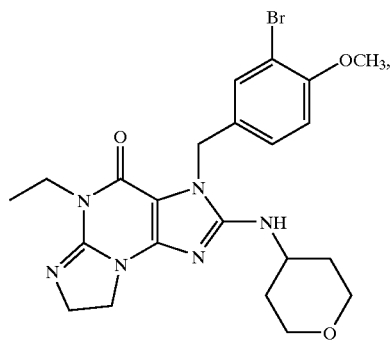
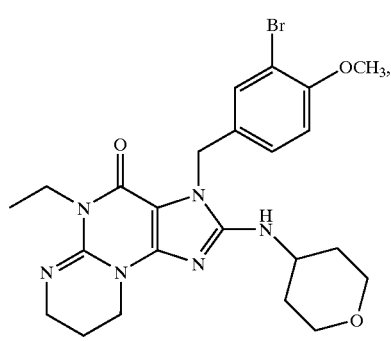
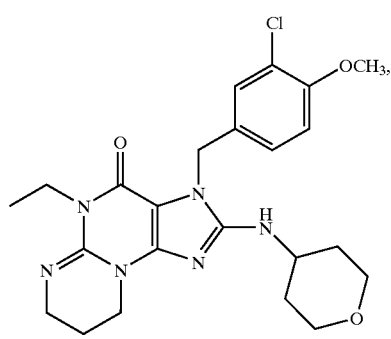
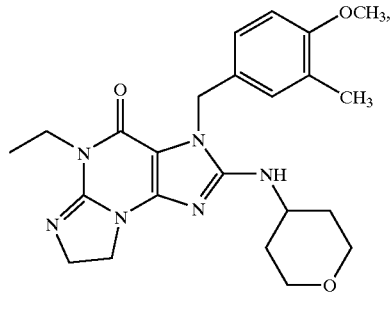
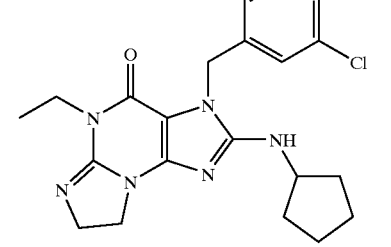

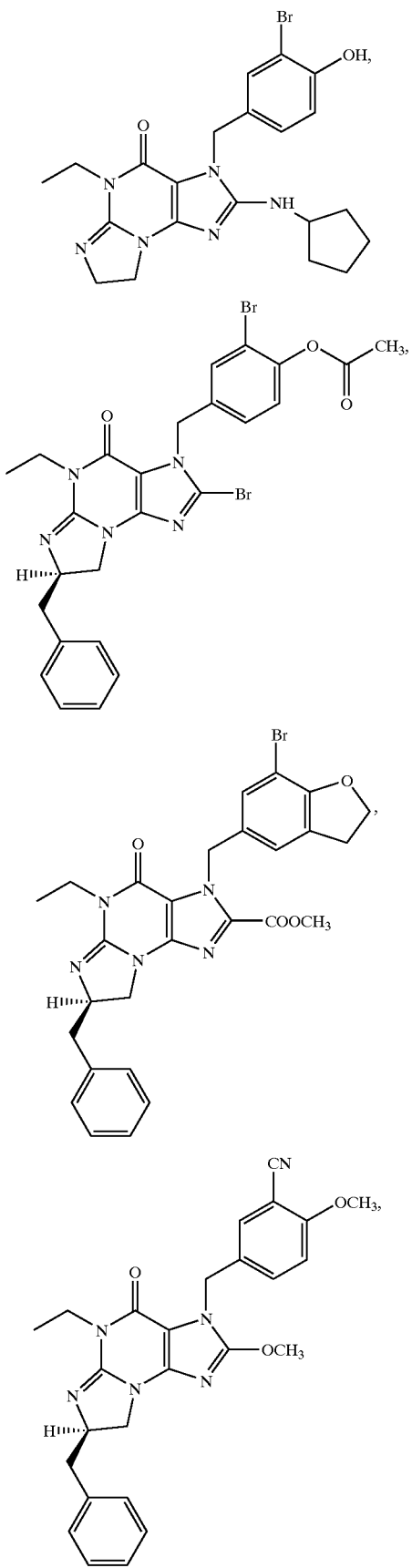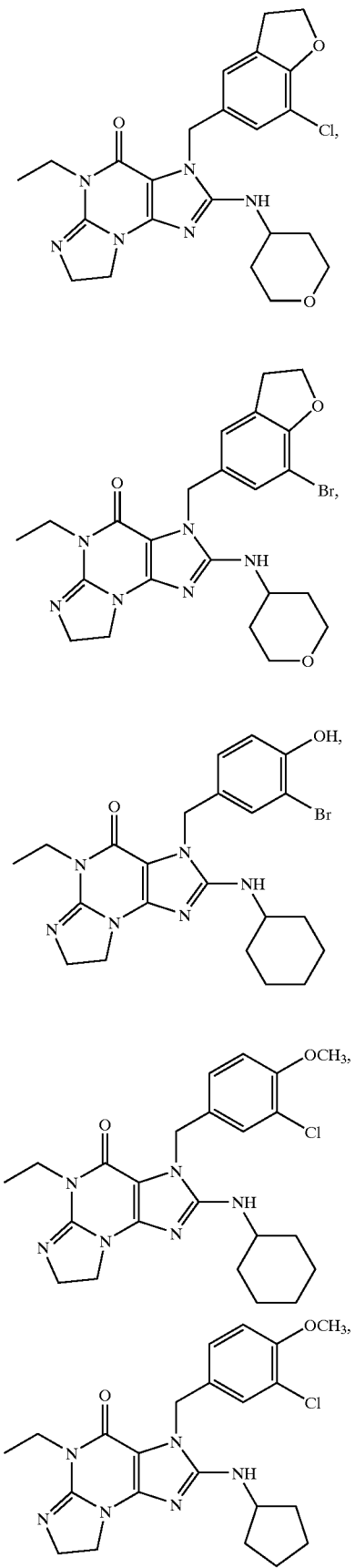

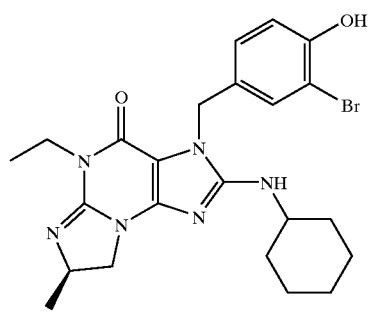
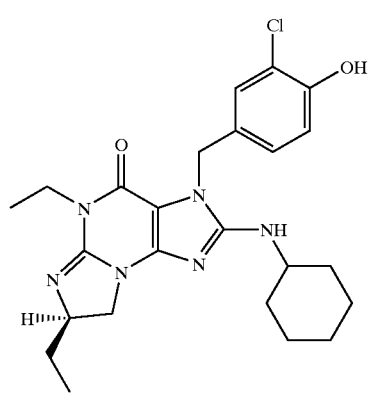
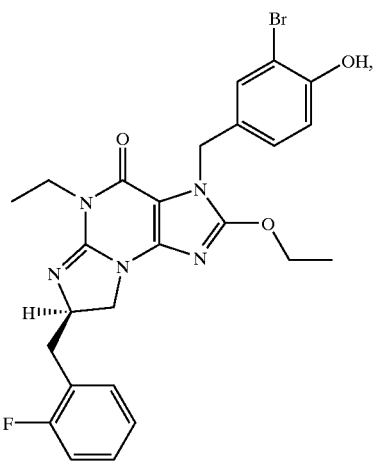
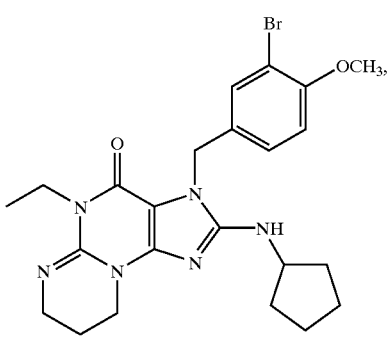
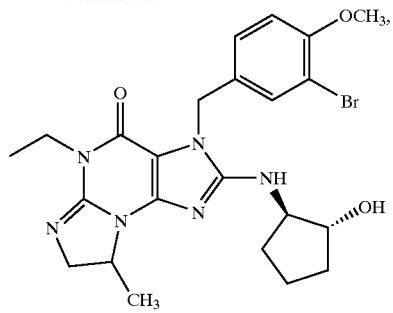
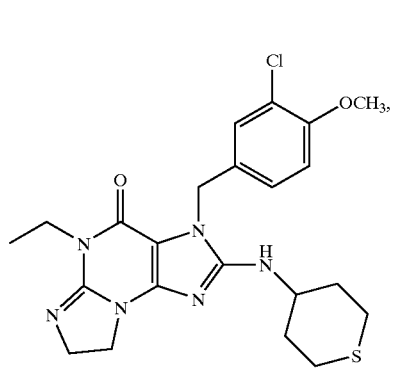
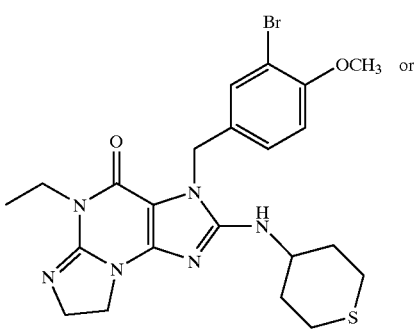
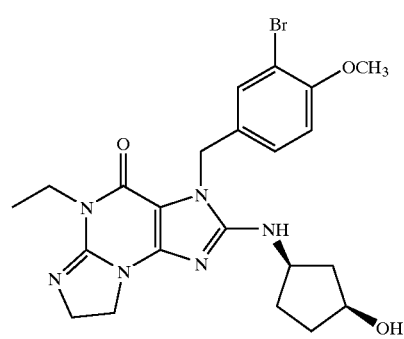
5. The compound or pharmaceutically acceptable salt according to claim 1, which is

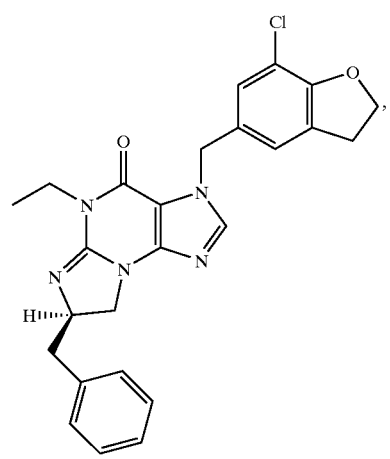
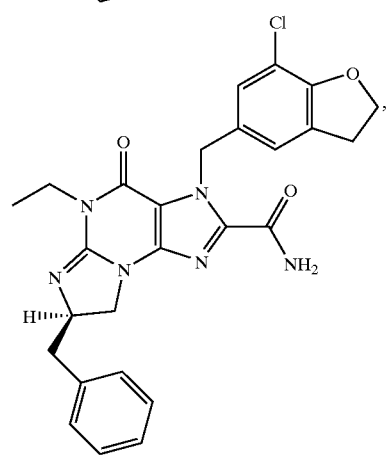
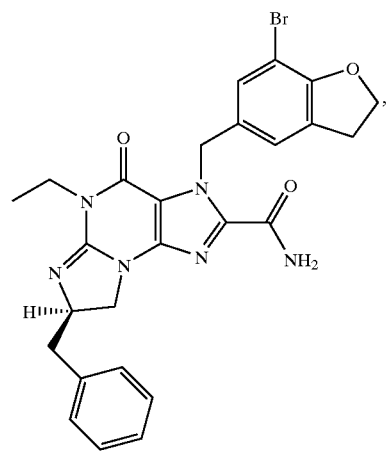
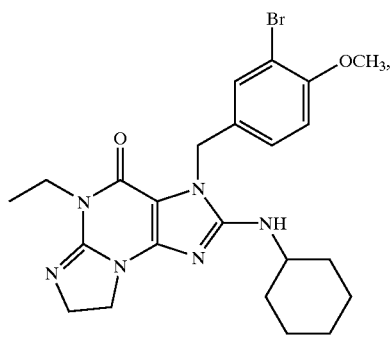
-continued
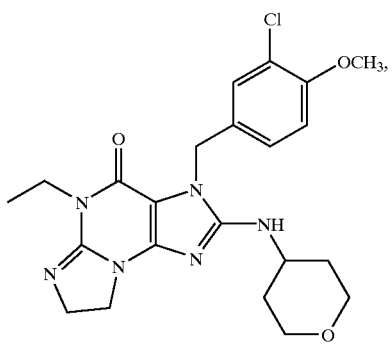
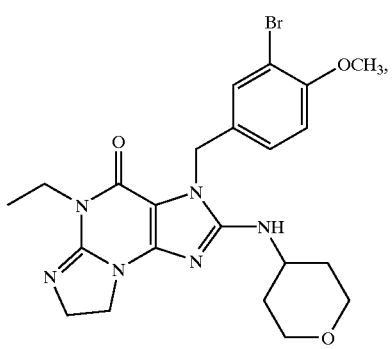
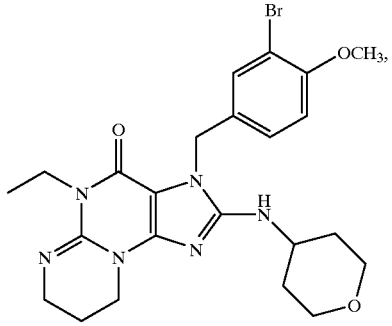
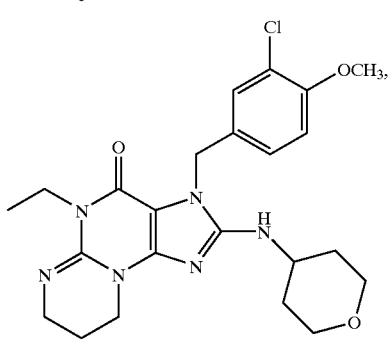
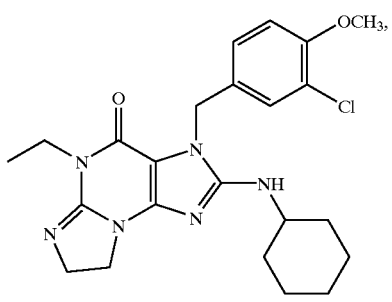

-continued

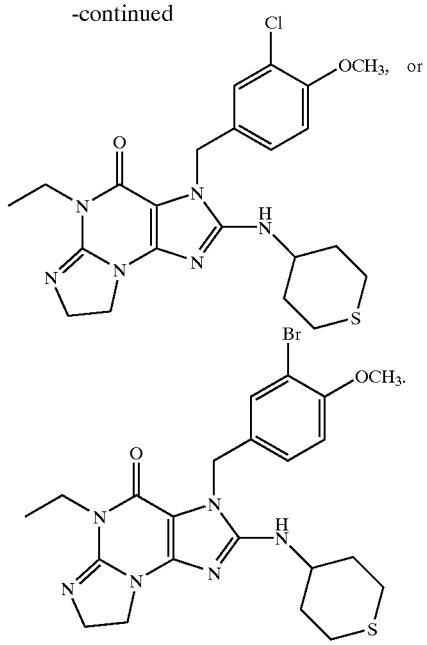

6. The compound or pharmaceutically acceptable salt according to claim 1, which is

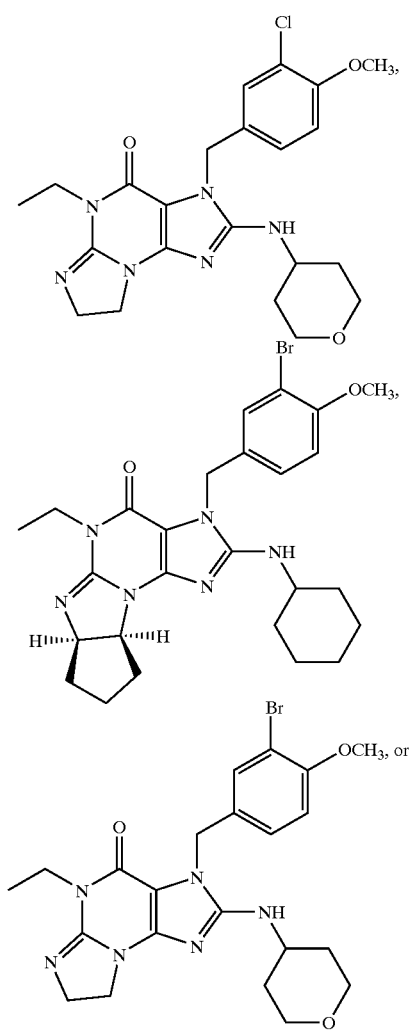

-continued

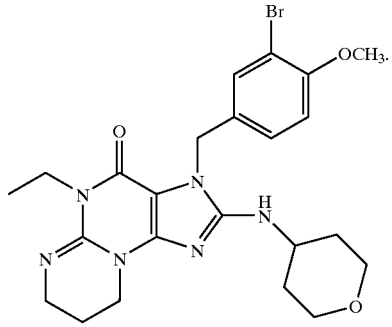

7. The compound or pharmaceutically acceptable salt according to claim 1, which is

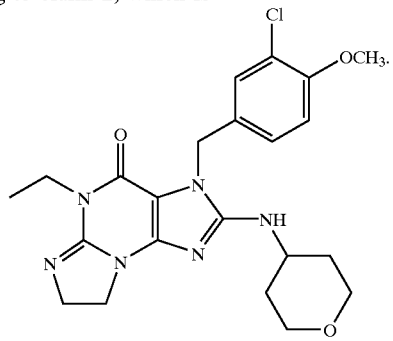

8. The compound or pharmaceutically acceptable salt according to claim 1, which is

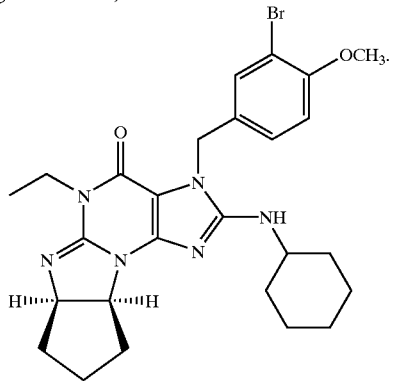

9. The compound or pharmaceutically acceptable salt according to claim 1, which is

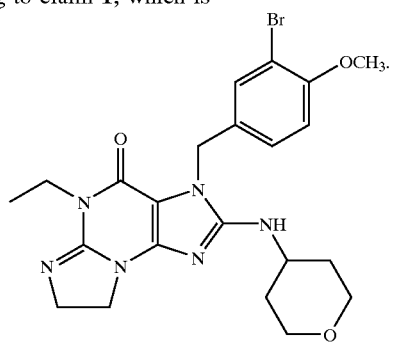

10. The compound or pharmaceutically acceptable salt according to claim 1, which is

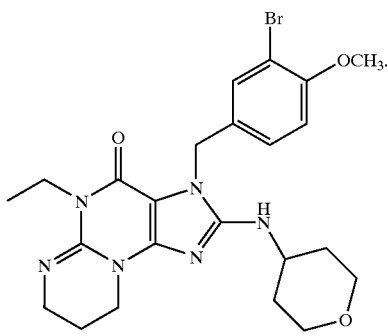

11. The compound or pharmaceutically acceptable salt according to claim 1, where the compound has the formula (I.1):

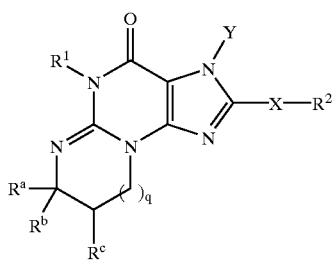

where the substituents are defined in claim 1.

12. The compound or pharmaceutically acceptable salt according to claim 1, where X is —NH—, and $R^2$ is:

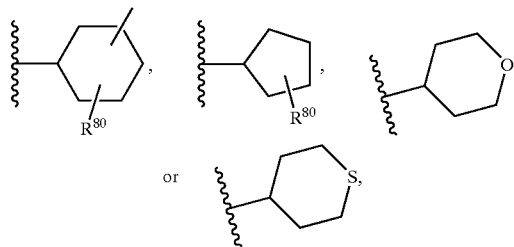

where $R^{80}$ is H or hydroxy.

13. The compound or pharmaceutically acceptable salt according to claim 1, where X is —O—, Y is defined in section (ii) of claim 1, and $R^2$ is alkyl or aralkyl.

14. The compound or pharmaceutically acceptable salt according to claim 1, where X is —C≡C—, and $R^2$ is alkyl or $R^{25}$, where $R^{26}$ is defined in claim 1.

15. The compound or pharmaceutically acceptable salt according to claim 1, where X is a bond, Y is defined in section (ii) of claim 1, and $R^2$ is halo, —CONHR$^6$, —CONR$^6$R$^7$, —CO$_2$R$^6$ or —C=N—OR$^6$, where R$^6$ and R$^7$ are each independently defined in claim 1.

16. The compound or pharmaceutically acceptable salt according to claim 1, where;
   (a) $R^a$ is alkyl or $R^{24}$-alkyl-, and $R^b$ and $R^c$ are each H, where $R^{24}$ is defined in claim 1; or
   (b) $R^a$ and $R^b$, together with the carbon to which they are both attached, form a 5- or 6-membered ring, and $R^c$ is H; or
   (c) $R^a$ and $R^c$, together with the respective carbons to which they are attached, form a 5-membered ring, and $R^b$ is H; or
   (d) $R^a$, $R^b$ and $R^c$ are each H.

17. The compound or pharmaceutically acceptable salt according to claim 1, where X is —NR$^8$—, Y is defined in section (i) of claim 1, and $R^2$ is a group defined by the formula (III.1):

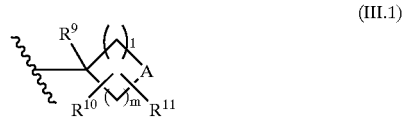

where,
  $R^8$ is H or alkyl;
  $R^8$, $R^{10}$ and $R^{11}$, independently of one another, are selected from the group consisting of H, cycloalkyl, heterocycloalkyl, carboxyl, carboxamido, alkoxycarbonyl, aryloxycarbonyl, oximino, alkyl, $R^{32}$-alkyl- and $R^{26}$, where
  $R^{32}$ is cycloalkyl, heterocycloalkyl, carboxamido, alkoxycarbonyl, aryloxycarbonyl, hydroxy, alkoxy, amino, monoalkylamino, dialkylamino or $R^{26}$, and
  $R^{26}$ is defined in claim 1; or
  $R^9$ and $R^{10}$, together with the carbon, carbons and/or heteroatom of the ring to which they are attached, form a linearly-fused or bridged bicyclic ring of 7 to 12 members, and $R^{11}$ is defined above; or
  $R^{10}$ and $R^{11}$ are, independently of one another, selected from the group consisting of hydroxy, alkoxy, aryloxy, acyloxy, —C(O)OR$^{34}$, where $R^{34}$ is defined in claim 1, amino, alkylamino, dialkylamino, acylamino and alkylsulfonylamino, and $R^9$ is defined above; or
  $R^{10}$ and $R^{11}$, together with the carbon, carbons and/or heteroatom of the ring to which they are attached, form a linearly-fused, spiro-fused or bridged bicyclic ring of 7 to 12 members, and $R^9$ is defined above;
  l and m are, independently of one another, each 1 to 3; and
  A is —O—, —S—, —C(R$^4$R$^{16}$)—, —SO—, —SO$_2$— or —NR$^{12}$—, where
    $R^4$ and $R^{16}$ are, independently of one another, each selected from the group consisting of H, cycloalkyl heterocycloalkyl, carboxyl, carboxamido, alkoxycarbonyl, aryloxycarbonyl, oximino, alkyl, $R^{32}$-alkyl- and $R^{26}$, where $R^{32}$ is defined above and $R^{26}$ is defined in claim 1; and
    $R^{12}$ is heterocycloalkyl, $R^7$, $R^{26}$, —COR$^{13}$, —SO$_2$R$^{14}$, —CO$_2$R$^{14}$, —CONR$^{13}$R$^{15}$ or —SO$_2$NR$^{13}$R$^{15}$, where
      $R^7$ is defined in claim 1;
      $R^{14}$ is alkyl, alkenyl, cycloalkyl, cycloalkylalkyl, heterocycloalkyl or $R^{26}$, where $R^{26}$ is defined in claim 1; and
      $R^{13}$ and $R^{15}$ are, independently of one another, each selected from the group consisting of H and $R^{14}$; or
      $R^{13}$ and $R^{15}$, together with the nitrogen to which they are both attached, form a 4- to 8-membered ring.

18. The compound or pharmaceutically acceptable salt according to claim 17, where $R^9$, $R^{10}$ and $R^{11}$ are each H.

19. The compound or pharmaceutically acceptable salt according to claim 1, where $R^a$ is $R^{24}$-alkyl-, and $R^b$ and $R^c$ are each H, where $R^{24}$ is defined in claim 1.

20. The compound or pharmaceutically acceptable salt according to claim 1, where the compound has a PDE V IC$_{50}$ of between <0 nM and about 5 nM.

21. The compound or pharmaceutically acceptable salt according to claim 1, where the compound has a ratio of PDE VI IC$_{50}$/PDE V IC$_{50}$ of >about 140.

22. The compound or pharmaceutically acceptable salt according to claim 1, where the compound has a PDE V $IC_{50}$ of between >0 nM and about 5 nM and a ratio of PDE VI $IC_{50}$/PDE V $IC_{50}$ of > about 140.

23. A pharmaceutical composition comprising the compound or pharmaceutically acceptable salt according to claim 1 and a pharmaceutically acceptable excipient or carrier.

24. A method for treating a physiological disorder, symptom or disease in a patient in need of the treatment, comprising administering to the patient an effective amount of at least one of the compound or pharmaceutically acceptable salt according to claim 1, wherein the physiological disorder, symptom or disease is male erectile dysfunction.

25. A method for elevating a cGMP level in a patient, comprising administering to the patient an effective amount of at least one of the compound or pharmaceutically acceptable salt according to claim 1.

26. A method for treating an erectile dysfunction in a patient in need of the treatment, comprising administering to the patient a combination therapy, comprising an effective amount of at least one of the compound or pharmaceutically acceptable salt according to claim 1 and at least one compound selected from the group consisting of: a prostanoid, α-adrenergic receptor, dopamine receptor agonist, melanocortin receptor agonist, endothelin receptor antagonist, endothelin converting enzyme inhibitor, angiotensin II receptor antagonist, angiotensin converting enzyme inhibitor, neutral metalloendopeptidase inhibitor, renin inhibitor, serotonin 5-$HT_{2c}$ receptor agonist, nociceptin receptor agonist, rho kinase inhibitor, potassium channel modulator and multidrug resistance protein 5 inhibitor.

\* \* \* \* \*